United States Patent
Späth et al.

(10) Patent No.: US 11,987,557 B2
(45) Date of Patent: May 21, 2024

(54) PHENALENE-1-ONE-CONTAINING PHOTOSENSITIZER COMPOSITION, PHENALENE-1-ONE COMPOUND AND THE USE THEREOF

(71) Applicant: TriOptoTec GmbH, Regensburg (DE)

(72) Inventors: Andreas Späth, Regensburg (DE); Anja Eichner, Regensburg (DE)

(73) Assignee: TRIOPTOTEC GMBH, Regensburg (DE)

( * ) Notice: Subject to any disclaimer, the term of this patent is extended or adjusted under 35 U.S.C. 154(b) by 0 days.

(21) Appl. No.: 17/500,593

(22) Filed: Oct. 13, 2021

(65) Prior Publication Data

US 2022/0064114 A1 Mar. 3, 2022

Related U.S. Application Data

(62) Division of application No. 16/494,836, filed as application No. PCT/EP2018/056653 on Mar. 16, 2018, now Pat. No. 11,186,545.

(30) Foreign Application Priority Data

Mar. 17, 2017 (EP) .................................... 17161718

(51) Int. Cl.
| | | |
|---|---|---|
| *C07D 213/30* | (2006.01) | |
| *C07C 49/755* | (2006.01) | |
| *C07C 69/56* | (2006.01) | |
| *C07C 69/76* | (2006.01) | |
| *C07C 211/62* | (2006.01) | |
| *C07C 233/18* | (2006.01) | |
| *C07C 233/20* | (2006.01) | |
| *C07C 309/14* | (2006.01) | |
| *C07C 317/22* | (2006.01) | |
| *C07D 303/14* | (2006.01) | |
| *C07D 303/18* | (2006.01) | |
| *C07D 309/14* | (2006.01) | |
| *C07F 7/02* | (2006.01) | |
| *C07F 7/18* | (2006.01) | |

(52) U.S. Cl.
CPC .......... *C07D 213/30* (2013.01); *C07C 49/755* (2013.01); *C07C 69/56* (2013.01); *C07C 69/76* (2013.01); *C07C 211/62* (2013.01); *C07C 233/18* (2013.01); *C07C 233/20* (2013.01); *C07C 317/22* (2013.01); *C07D 303/18* (2013.01); *C07D 309/14* (2013.01); *C07F 7/025* (2013.01); *C07F 7/1804* (2013.01)

(58) Field of Classification Search
CPC .. C07D 213/30; C07D 303/18; C07D 309/14; C07D 303/22; C07D 303/12; C07C 49/755; C07C 69/56; C07C 69/76; C07C 211/62; C07C 233/18; C07C 233/20; C07C 317/22; C07C 2601/14; C07C 2603/28; C07C 49/737; C07C 69/54; C07C 217/08; C07C 217/10; C07C 217/12; C07C 225/18; C07C 233/31; C07C 233/38; C07C 271/16; C07C 271/20; C07C 69/94; C07C 225/14; C07C 317/24; C07F 7/025; C07F 7/1804; C07F 7/045; C07F 7/0834; C07F 7/04; C08K 5/0041; C08K 5/3432; C08K 5/37
See application file for complete search history.

(56) References Cited

U.S. PATENT DOCUMENTS

| | | | |
|---|---|---|---|
| 3,865,879 | A | 2/1975 | Eiglmeier |
| 4,464,511 | A | 8/1984 | Naarmann et al. |
| 4,468,509 | A | 8/1984 | Naarmann et al. |
| 5,830,526 | A | 11/1998 | Wilson et al. |
| 9,302,004 | B2 | 4/2016 | Bäumler et al. |
| 2014/0039184 | A1 | 2/2014 | Bäumler et al. |

FOREIGN PATENT DOCUMENTS

| | | |
|---|---|---|
| EP | 0 069 292 A1 | 1/1983 |
| EP | 0 104 388 A2 | 4/1984 |
| JP | A-S55-090506 A | 7/1980 |
| JP | A-S60-006757 A | 1/1985 |
| SU | 509212 A3 | 3/1976 |
| WO | WO 00/78854 A1 | 12/2000 |
| WO | WO 2012/113860 A2 | 8/2012 |

OTHER PUBLICATIONS

International Search Report and Written Opinion dated May 22, 2018 in corresponding PCT International Application No. PCT/EP2018/056653 (with English translation).
A.D. Jenkins, et at., "Glossary of Basic Terms in Polymer Science (IUPAC Recommendations 1996)," Pure & Appl. Chem., 68 (12), 1996, pp. 2287-2311.
John M. Boyce, M.D., et al., "Guideline for Hand Hygiene in Health-Care Settings. Recommendations of the Healthcare Infection Control Practices Advisory Committee and the HICPAC/SHEA/APIC/IDSA Hand Hygiene Task Force," Am. J. Infect. Control 30 (8), (2002), pp. 1-46.
Din En 14885 (Jan. 2007), "Chemische Desinfektionsmittel und Antiseptika-Anwendung Europäischer Normen für chemische Desinfektionsmittel und Antiseptika" (with English version).
Prof. Dr. Holger F. Rabenau, et al., ("Leitlinie der Deutschen Vereinigung zur Bekämpfung der Viruskrankheiten (DVV) e.V. und des Robert Koch Instituts (RKI) zur Prüfung von chemischen Desinfektionsmitteln auf Wirksamkeit gegen Viren in der Humanmedizin" Bundesgesundheitsblatt, Gesundheitsforschung, Gesundheitsschutz 51(8), (2008), pp. 937-945. "Guidelines from the German Association for the Control of Viral Diseases (DVV) and the Robert Koch Institute (RKI) for testing chemical disinfectants for effectiveness against viruses in human medicine." (with English version).
Ariane Felgenträger, "Singlet Oxygen Generation in Porphyrin-Doped Polymeric Surface Coating Enables Antimicrobial Effects on *Staphylococcus aureus*," Phys. Chem. Chem. Phys., 16, 2014, pp. 20598-20607, doi:10.1039/c4cp02439g.

(Continued)

Primary Examiner — John M Mauro
(74) Attorney, Agent, or Firm — OSTROLENK FABER LLP

(57) ABSTRACT

A phenalene-1-one compound, a photosensitizer composition including the phenalene-1-one compound, an article including the phenalene-1-one compound and/or photosensitizer composition and the use thereof.

8 Claims, 2 Drawing Sheets

(56) References Cited

OTHER PUBLICATIONS

I. Meirovics, et al., "Enol Ethers of 2-Arylperinaphthindan-1,3-Diones," CA1966, STN Database Accession No. 1966:447525; XP002770280 & I. Meirovics, et al., "Enol Ethers of 2-Arylperinaphthindan-1,3-Diones," Latvijas PSR Zinatnu Akademijas Vestis, Kimijas Serija, CODEN: Lzakam; ISSN: 0002-3248, No. 5, 1965, pp. 579-586.
David A. Frost, et al., "Naturally Occurring Compounds Related to Phenalenone. Part V.[1] Synthetic Approaches to Structures Based on 8,9-Dihydro-8,8,9-trimethyl-phenaleno[1,2-b] Furan-7-One," Journal of the Chemical Society, Perkin Transactions 1, Jan. 1, 1973 (Jan. 1, 1973), pp. 2159-2169, XP055371432.
Wikipedia Bacterial Cell Structure (2021) (accessed online https://en.wikipedia.org/wiki/Bacterial_cell_structure).
Isabelle Tabenski, et al. "The Impact of Cationic Substituents in Phenalen-1-one Photosensitizers on Antimicrobial Photodynamic Efficacy," Photochemical & Photobiological Sciences, 2016, 15(1), pp. 57-68.
CAS Registry No. 5060-99-1 / CAS Registry No. 5525-20-2, Nov. 16, 1984 (2 pages).
Wikipedia—Urethane (2 pages).
Wikipedia—Amide (4 pages).

PHENALENE-1-ONE-CONTAINING PHOTOSENSITIZER COMPOSITION, PHENALENE-1-ONE COMPOUND AND THE USE THEREOF

CROSS-REFERENCE TO RELATED APPLICATIONS

The present patent application is a divisional of prior U.S. patent application Ser. No. 16/494,836, filed Sep. 17, 2019, by Andreas SPÄTH and Anja EICHNER, entitled "PHENALENE-1-ONE-CONTAINING PHOTOSENSITIZER COMPOSITION, PHENALENE-1-ONE COMPOUND AND THE USE THEREOF," which is a 35 U.S.C. §§ 371 national phase conversion of PCT/EP2018/056653, filed Mar. 16, 2018, which claims priority to European Patent Application No. 17161718.6, filed Mar. 17, 2017. The PCT International Application was published in the German language. The contents of each of the patent applications listed above are incorporated in full herein by reference.

TECHNICAL FIELD

The present invention relates to a photosensitizer composition, to a phenalen-1-one compound, to an article as well as to its use.

BACKGROUND OF THE INVENTION

The active or passive penetration, adhesion and proliferation of pathogens in a host is described as an infection. Sources of infectious particles are everywhere. Thus, for example, the human body is colonized by a large number of microorganisms which as a rule are kept under control by the normal metabolism and an intact immune system. However, when, for example, the immune system is weakened, the pathogens can proliferate sharply and, depending on the type of pathogen, may lead to various symptoms of disease. Medicine has specific countermeasures available against many pathogen-related diseases, for example antibiotics against bacteria or antimycotics against fungi or antivirals against viruses. However, more and more often when employing these countermeasures, the occurrence of resistant pathogens has been observed, some of which have also been shown to be resistant to several counter-measures. Because of the occurrence of these resistant or multi-resistant pathogens, the therapy of infectious diseases is becoming increasingly more difficult. The clinical consequence of resistance is evidenced by a failure of treatment, especially in immunosuppressed patients.

New approaches to controlling resistant or multi-resistant pathogens are thus on the one hand research into novel counter-measures, for example antibiotics or antimycotics, and on the other hand research into alternative inactivation strategies.

An alternative method has been shown to be the photodynamic inactivation of microorganisms. Two different photo-oxidative processes play a decisive role in the photodynamic inactivation of microorganisms. The condition for a photo-oxidative inactivation to occur is on the one hand the presence of a sufficient quantity of oxygen and on the other hand the localization of what is known as a photosensitizer, which is excited by light of an appropriate wavelength. The excited photosensitizer can bring about the formation of reactive oxygen species (ROS), wherein on the one hand radicals, for example superoxide anions, hydrogen peroxide or hydroxyl radicals and/or on the other hand excited molecular oxygen, for example singlet oxygen, may be formed.

In both reactions, the photo-oxidation of specific biomolecules which are in the direct vicinity of the reactive oxygen species (ROS) is paramount. In this regard, in particular, the oxidation of lipids and proteins occurs which, for example, are present as components of the cell membrane of microorganisms. In turn, destruction of the cell membrane leads to the inactivation of the relevant microorganisms. A similar elimination process occurs for viruses and fungi.

As an example, all molecules are attacked by singlet oxygen. However, unsaturated fatty acids in the membranes of bacteria are particularly susceptible to damage. Healthy endogenous cells have a cellular defense against attacks from free radicals—through what are known as catalases or superoxide dismutases. Thus, healthy, endogenous cells can counteract damage by reactive oxygen species (ROS), for example radicals or singlet oxygen.

Many photosensitizers are known from the prior art which, for example, originate from the group formed by porphyrins and their derivatives or phthalocyanines and their derivatives or fullerenes and their derivatives or derivatives with a phenothiazinium structure such as methylene blue or toluidine blue, for example, or representatives of the phenoxazinium series such as Nile blue, for example.

WO 00/78854 A1 concerns a method for the preparation of an antimicrobial surface, wherein the method comprises combining one or more polymers with one or more photosensitizers in order to form a surface which has a hardened polymeric composition which comprises one or more polymers and one or more non-covalent and non-ionically bonded photosensitizers, wherein at least one thereof is a xanthene photosensitizer.

The disadvantage in that case is that the photosensitizer leaks out of the polymer matrix, and thus the antimicrobial activity diminishes when stored for lengthy periods.

U.S. Pat. No. 5,830,526 A discloses a substrate onto which a light-activatable dye is bonded alone or in combination with additional conventional antimicrobial and/or antiviral agents. The substrate is impregnated with a light-activatable dye with antimicrobial and/or antiviral properties, wherein a cationic or anionic water-soluble polymer binds the dye to the substrate.

The disadvantage in that case is that the photosensitizer can be released from the substrate, for example by mechanical stress, and thus the antimicrobial activity is reduced.

SUMMARY OF THE INVENTION

The objective of the present invention is to provide a coating containing a photosensitizer which guarantees ease of application, preferably to different types of surfaces, and in particular simultaneously exhibits good antimicrobial activity following illumination with electromagnetic radiation of a suitable wavelength and intensity.

Furthermore, following application to a surface, the photosensitizer-containing coating should preferably ensure an improved adhesion of the photosensitizer, so that hemorrhaging of the photosensitizer is preferably avoided.

Furthermore, preferably, the activity of the photosensitizer, in particular upon lengthy irradiation with electromagnetic radiation of a suitable wavelength and intensity, should be improved.

In this regard, the photosensitizer-containing coating should essentially not inhibit the excitation of the photosensitizer molecules contained in the coating by light of a specific wavelength.

The objective of the present invention is achieved by providing a photosensitizer composition as disclosed herein, comprising
(a) at least one phenalen-1-one compound with the general formula (1):

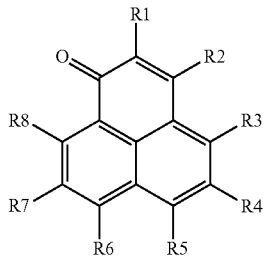

(1)

wherein the residues R1 to R8, which respectively independently of one another may be identical to or different from each other, respectively represent hydrogen, halogen, alkyl containing 1 to 12 C atoms, alkylaryl containing 5 to 20 C atoms, aryl containing 5 to 20 C atoms, *—O-alkyl containing 1 to 12 C atoms, *—O-alkylaryl containing 5 to 20 C atoms, *—O-aryl containing 5 to 20 C atoms, ether containing 2 to 12 C atoms, a residue with the formula *—O—C(=O)—R$^{(Ia)}$, a residue with the formula *—C(=O)—R$^{(Ib)}$, or an organic residue W1 which contains at least one reactive functional group, with the proviso that at least one of the residues R1 to R7, preferably at least one of the residues R1, R2, R5 or R6, more preferably at least one of the residues R1 or R2, is an organic residue W1, wherein the organic residue W1 respectively independently of each other represents a residue with the general formula (2) to (6):

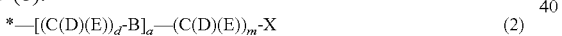 (2)

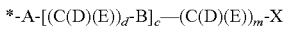 (3)

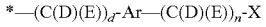 (4)

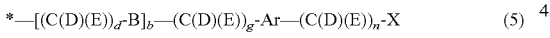 (5)

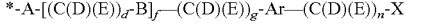 (6)

wherein the residue A respectively independently of each other represents oxygen, sulphur or a residue with the general formula (10a) to (11a), preferably oxygen or a residue with the general formula (10a), more preferably oxygen:

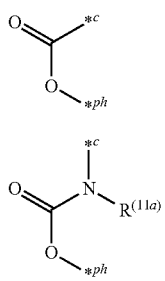

(10a)

(11a)

wherein *$^{ph}$ respectively denotes a linkage from the residue with the general formula (10a) to (11a) to a C atom of the phenalene ring and *$^c$ respectively denotes a linkage from the residue with the general formula (10a) to (11a) to a C atom of the residue (C(D)(E)), and
wherein the residue B respectively independently of each other represents oxygen, sulphur or a residue with the general formula (10) to (14), preferably oxygen or a residue with the general formula (10) to (14):

 (10)

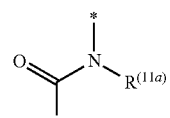 (11)

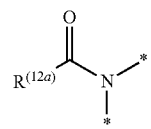 (12)

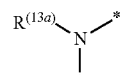 (13)

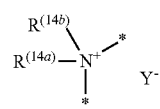 (14)

wherein the residues R$^{(Ia)}$, R$^{(Ib)}$, R$^{(11a)}$, R$^{(12a)}$, R$^{(13a)}$, R$^{(14a)}$ and R$^{(14b)}$ respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group which consists of halogen, amino, hydroxyl, *—O-alkyl which may be linear or branched, containing 1 to 3 carbon atoms, alkyl which may be linear or branched, containing 1 to 3 carbon atoms, hydroxyalkyl which may be linear or branched, containing 1 to 3 carbon atoms and 1 to 3 OH groups, halogenoalkyl which may be linear or branched, containing 1 to 3 carbon atoms and 1 to 3 halogen groups, and combinations thereof, preferably chlorine, bromine, fluorine, methyl, ethyl, n-propyl, iso-propyl, methoxy, ethoxy, and combinations thereof, wherein Y$^-$ is an anion which respectively independently of each other represents fluoride, chloride, bromide, iodide, sulphate, hydrogen sulphate, phosphate, hydrogen phosphate, dihydrogen phosphate, at least one carboxylate anion of a carboxylic acid containing 1 to 15 carbon atoms, at least one sulphonate anion of a sulphonic acid containing 1 to 12 C atoms, or a combination thereof,
wherein the residues D and E respectively independently of each other represent hydrogen, halogen, hydroxyl, alkyl which may be linear or branched, containing 1 to 5 carbon atoms, hydroxyalkyl which may be linear or branched, containing 1 to 5 carbon atoms and 1 to 5 OH groups, halogenoalkyl which may be linear or branched, containing 1 to 5 carbon atoms and 1 to 5 halogen groups, phenyl, benzyl, a residue with the formula *-L-R$^{(II)}$, a residue with the formula *-L-C(=L)-R$^{(III)}$, a residue with the formula *—(CH$_2$)$_q$—X, a residue with the formula *-L-(CH$_2$)$_q$—X, or a residue with the formula *—(CH$_2$)$_s$-L-(CH$_2$)$_t$—X, wherein the residue L respectively independently of each other represents oxygen or sulphur, preferably oxygen, wherein the residues R$^{(II)}$ and R$^{(III)}$ respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, and wherein the indices q, s and t respectively independently of each other represent a whole number from 1 to 5, wherein the indices a, c, g, f and n respectively independently of each other represent a whole number from 0 to 5, preferably from 1 to 4, and wherein the indices b, d and m respectively independently of each other represent a whole number from 1 to 5, preferably from 2 to 4, wherein the residue Ar respectively independently of each other represents a substituted or unsubstituted aromatic compound or a substituted or unsubstituted heteroaromatic compound, and wherein the residue X respectively independently of each other is a reactive functional group denoted by *—N(R$^{(VI)}$)(R$^{(VII)}$), *—OH, *—SH, *—NCO, *—NCS, *—Si(R$^{(VIII)}$)(R$^{(IX)}$)—[O—Si(R$^{(X)}$)(R$^{(XI)}$)]$_p$—Z, or a residue with the general formula (20) to (24):

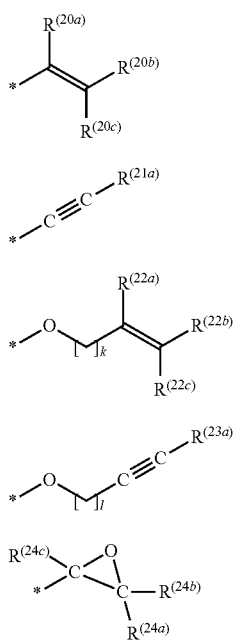

wherein the residues R$^{(20a)}$, R$^{(20b)}$, R$^{(20c)}$, R$^{(21a)}$, R$^{(22a)}$, R$^{(22b)}$, R$^{(22c)}$, R$^{(23a)}$, R$^{(24a)}$, R$^{(24b)}$, and R$^{(24c)}$ respectively independently of each other, represent hydrogen, methyl, ethyl, n-propyl, iso-propyl, n-butyl, sec-butyl, iso-butyl, or n-pentyl, preferably hydrogen, methyl or ethyl, and wherein the indices l and k respectively independently of each other represent a whole number from 0 to 4, wherein the residues R$^{(VI)}$ and R$^{(VII)}$ respectively independently of each other represent hydrogen, alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, wherein the residues R$^{(VIII)}$, R$^{(IX)}$, R$^{(X)}$ and R$^{(XI)}$ respectively independently of each other represent hydrogen, alkyl which may be linear or branched, containing 1 to 5 carbon atoms, *—O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, wherein the residue Z respectively independently of each other represents halogen, hydroxyl, alkoxyl containing 1 to 4 carbon atoms or alkylcarboxyl containing 1 to 4 carbon atoms, preferably halogen or hydroxyl, and wherein the index p respectively independently of each other represents a whole number from 0 to 4, and (b) at least one polymeric component and/or precursor thereof.

Preferred embodiments of the photosensitizer composition in accordance with the invention are provided herein.

The objective of the present invention is also achieved by providing a phenalen-1-one compound as disclosed herein, wherein the phenalen-1-one compound has the general formula (1a):

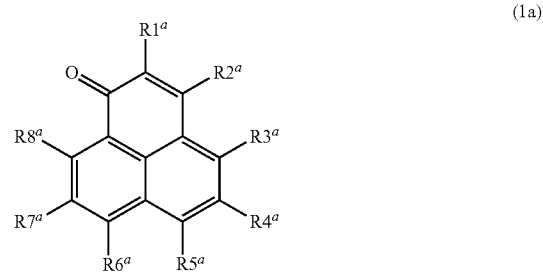

wherein the residues R1$^a$ to R8$^a$, which respectively independently of one another may be identical to or different from each other, respectively represent hydrogen, halogen, alkyl containing 1 to 12 C atoms, alkylaryl containing 5 to 20 C atoms, aryl containing 5 to 20 C atoms, *—O-alkyl containing 1 to 12 C atoms, *—O-alkylaryl containing 5 to 20 C atoms, *—O-aryl containing 5 to 20 C atoms, ether containing 2 to 12 C atoms, a residue with the formula *—O—C(=O)—R$^{(Ia)}$, a residue with the formula *—C(=O)—R$^{(Ib)}$, or an organic residue W1a which contains at least one reactive functional group, with the proviso that at least one of the residues R1$^a$ or R2$^a$, preferably one of the residues R1$^a$ or R2$^a$, is an organic residue W1a, wherein the organic residue W1a respectively independently of each other represents a residue with the general formula (2a) to (6a):

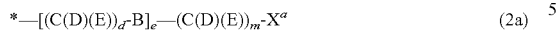   (2a)

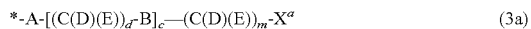   (3a)

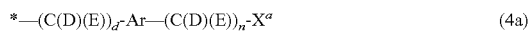   (4a)

   (5a)

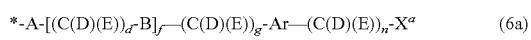   (6a)

wherein the residue A respectively independently of each other represents oxygen, sulphur or a residue with the general formula (10a) to (11a), preferably oxygen or a residue with the general formula (10a), more preferably oxygen:

   (10a)

   (11a)

wherein *$^{ph}$ respectively denotes a linkage from the residue with the general formula (10a) to (11a) to a C atom of the phenalene ring and *$^c$ respectively denotes a linkage from the residue with the general formula (10a) to (11a) to a C atom of the residue (C(D)(E)), wherein the residue B respectively independently of each other represents oxygen, sulphur or a residue with the general formula (10) to (12); preferably oxygen or a residue with the general formula (10) to (12), preferably oxygen or a residue with the general formula (10):

   (10)

   (11)

   (12)

and wherein the residues R$^{(Ia)}$, R$^{(Ib)}$, R$^{(11a)}$ and R$^{(12a)}$ respectively independently of each other represent methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, and wherein the residues D and E respectively independently of each other represent hydrogen, halogen, hydroxyl, alkyl which may be linear or branched, containing 1 to 5 carbon atoms, hydroxyalkyl which may be linear or branched, containing 1 to 5 carbon atoms and 1 to 5 OH groups, phenyl, benzyl, a residue with the formula *-L-R$^{(II)}$, a residue with the formula *-L-C(=L)-R$^{(III)}$, a residue with the formula *—(CH$_2$)$_q$—X$^a$, a residue with the formula *-L-(CH$_2$)$_q$—X$^a$, or a residue with the formula *—(CH$_2$)$_s$-L-(CH$_2$)$_t$—X$^a$, wherein the residue L respectively independently of each other represents oxygen or sulphur, preferably oxygen, wherein the residues R$^{(II)}$ and R$^{(III)}$ respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, the indices q, s and t respectively independently of each other representing a whole number from 1 to 5, wherein the indices c, g, f and n respectively independently of each other represent a whole number from 0 to 5, preferably from 1 to 4, and wherein the indices b, d, e and m respectively independently of each other represent a whole number from 1 to 5, preferably from 2 to 4, wherein the residue Ar respectively independently of each other represents a substituted or unsubstituted aromatic compound or a substituted or unsubstituted heteroaromatic compound which contains no N atoms, and wherein the residue X$^a$ respectively independently of each other is a reactive functional group denoted by *—OH, *—SH, *—NCO, *—NCS, *—Si(R$^{(VIII)}$)(R$^{(IX)}$)—[O—Si(R$^{(X)}$)(R$^{(XI)}$)]$_p$—Z, or a residue with the general formula (20) to (24):

   (20)

   (21)

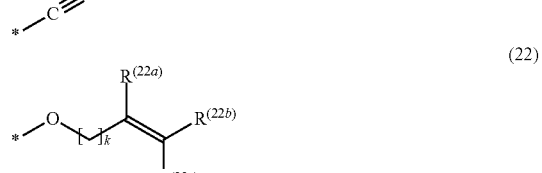   (22)

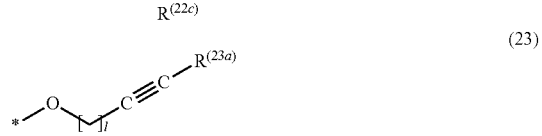   (23)

-continued

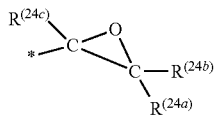
(24)

wherein the residues $R^{(20a)}$, $R^{(20b)}$, $R^{(20c)}$, $R^{(21a)}$, $R^{(22a)}$, $R^{(22b)}$, $R^{(22c)}$, $R^{(23a)}$, $R^{(24a)}$, $R^{(24b)}$, and $R^{(24c)}$ respectively independently of each other, represent hydrogen, methyl, ethyl, n-propyl, iso-propyl, n-butyl, sec-butyl, iso-butyl, or n-pentyl, and wherein the indices l and k respectively independently of each other represent a whole number from 0 to 4, wherein the residues $R^{(VIII)}$, $R^{(IX)}$, $R^{(X)}$ and $R^{(XI)}$ respectively independently of each other represent hydrogen, alkyl which may be linear or branched, containing 1 to 5 carbon atoms, *—O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, wherein the residue Z respectively independently of each other represents halogen, hydroxyl, alkoxyl containing 1 to 4 carbon atoms or alkylcarboxyl containing 1 to 4 carbon atoms, preferably halogen or hydroxyl, and wherein the index p respectively independently of each other represents a whole number from 0 to 4.

Preferred embodiments of the inventive phenalen-1-one compound are provided herein.

The objective of the present invention is furthermore achieved by the provision of an article as disclosed herein, wherein the article comprises at least one hardened polymer composition, wherein the hardened polymer composition comprises (a) at least one phenalen-1-one compound with the general formula (1):

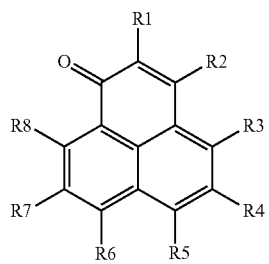
(1)

wherein the residues R1 to R8, which respectively independently of one another may be identical to or different from each other, respectively represent hydrogen, halogen, alkyl containing 1 to 12 C atoms, alkylaryl containing 5 to 20 C atoms, aryl containing 5 to 20 C atoms, *—O-alkyl containing 1 to 12 C atoms, *—O-alkylaryl containing 5 to 20 C atoms, *—O-aryl containing 5 to 20 C atoms, ether containing 2 to 12 C atoms, a residue with the formula *—O—C(=O)—$R^{(Ia)}$, a residue with the formula *—C(=O)—$R^{(Ib)}$, or an organic residue W1 which contains at least one reactive functional group, with the proviso that at least one of the residues R1 to R7, preferably at least one of the residues R1, R2, R5 or R6, more preferably at least one of the residues R1 or R2, is an organic residue W1, wherein the organic residue W1 respectively independently of each other represents a residue with the general formula (2) to (6):

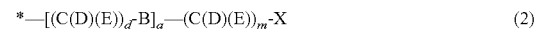
*—[(C(D)(E))$_d$-B]$_a$—(C(D)(E))$_m$-X (2)

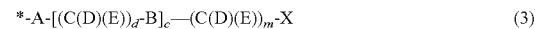
*-A-[(C(D)(E))$_d$-B]$_c$—(C(D)(E))$_m$-X (3)

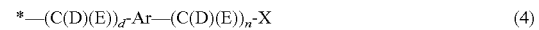
*—(C(D)(E))$_d$-Ar—(C(D)(E))$_n$-X (4)

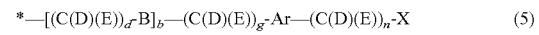
*—[(C(D)(E))$_d$-B]$_b$—(C(D)(E))$_g$-Ar—(C(D)(E))$_n$-X (5)

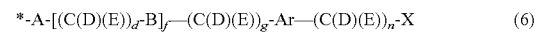
*-A-[(C(D)(E))$_d$-B]$_f$—(C(D)(E))$_g$-Ar—(C(D)(E))$_n$-X (6)

wherein the residue A respectively independently of each other represents oxygen, sulphur or a residue with the general formula (10a) to (11a), preferably oxygen or a residue with the general formula (10a), preferably oxygen:

(10a)

(11a)

wherein *$^{ph}$ respectively denotes a linkage from the residue with the general formula (10a) to (11a) to a C atom of the phenalene ring and *$^c$ respectively denotes a linkage from the residue with the general formula (10a) to (11a) to a C atom of the residue (C(D)(E)), wherein the residue B respectively independently of each other represents oxygen, sulphur or a residue with the general formula (10) to (14), preferably oxygen or a residue with the general formula (10), more preferably oxygen:

(10)

(11)

(12)

(13)

-continued

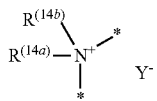
(14)

and wherein the residues $R^{(Ia)}$, $R^{(Ib)}$, $R^{(11a)}$, $R^{(12a)}$, $R^{(13a)}$, $R^{(14a)}$ and $R^{(14b)}$ respectively independently of each other represent methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group which consists of halogen, amino, hydroxyl, alkyl which may be linear or branched, containing 1 to 3 carbon atoms, hydroxyalkyl which may be linear or branched, containing 1 to 3 carbon atoms and 1 to 3 OH groups, halogenoalkyl which may be linear or branched, containing 1 to 3 carbon atoms and 1 to 3 halogen groups, and combinations thereof, preferably chlorine, bromine, fluorine, methyl, ethyl, n-propyl, iso-propyl, methoxy, ethoxy, and combinations thereof, wherein $Y^-$ is an anion which respectively independently of each other represents fluoride, chloride, bromide, iodide, sulphate, hydrogen sulphate, phosphate, hydrogen phosphate, dihydrogen phosphate, at least one carboxylate anion of a carboxylic acid containing 1 to 15 carbon atoms, at least one sulphonate anion of a sulphonic acid containing 1 to 12 C atoms, and wherein the residues D and E respectively independently of each other represent hydrogen, halogen, hydroxyl, alkyl which may be linear or branched, containing 1 to 5 carbon atoms, hydroxyalkyl which may be linear or branched, containing 1 to 5 carbon atoms and 1 to 5 OH groups, phenyl, benzyl, a residue with the formula *-L-$R^{(II)}$, a residue with the formula *-L-C(=L)-$R^{(III)}$, a residue with the formula *—$(CH_2)_q$—X, a residue with the formula *-L-$(CH_2)_q$—X, or a residue with the formula *—$(CH_2)_s$-L-$(CH_2)_t$—X, wherein the residue L respectively independently of each other represents oxygen or sulphur, preferably oxygen, wherein the residues $R^{(II)}$ and $R^{(III)}$ respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, the indices q, s and t respectively independently of each other representing a whole number from 1 to 5, wherein the indices a, c, f, g and n respectively independently of each other represent a whole number from 0 to 5, preferably from 1 to 4, and wherein the indices b, d and m respectively independently of each other represent a whole number from 1 to 5, preferably 2 to 4, wherein the residue Ar respectively independently of each other represents a substituted or unsubstituted aromatic compound or a substituted or unsubstituted heteroaromatic compound, and wherein the residue X respectively independently of each other is a reactive functional group denoted by *—N$(R^{(VI)})(R^{(VII)})$, *—OH, *—SH, *—NCO, *—NCS, *—Si($R^{(VIII)}$)($R^{(IX)}$)—[O—Si($R^{(X)}$)($R^{(XI)}$)$_p$]—Z, or a residue with the general formula (20) to (24):

(20)

(21)

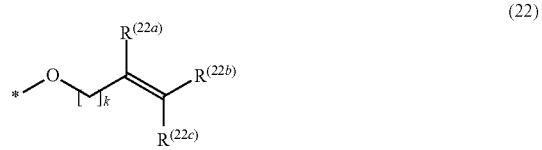
(22)

(23)

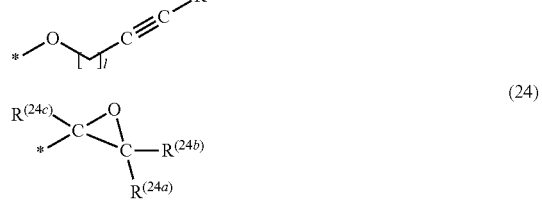
(24)

wherein the residues $R^{(20a)}$, $R^{(20b)}$, $R^{(20c)}$, $R^{(21a)}$, $R^{(22a)}$, $R^{(22b)}$, $R^{(22c)}$, $R^{(23a)}$, $R^{(24a)}$, $R^{(24b)}$, and $R^{(24c)}$ respectively independently of each other, represent hydrogen, methyl, ethyl, n-propyl, iso-propyl, n-butyl, sec-butyl, iso-butyl, or n-pentyl, preferably hydrogen, methyl or ethyl, and wherein the indices l and k respectively independently of each other represent a whole number from 0 to 4, wherein the residues $R^{(VI)}$, $R^{(VII)}$, $R^{(VIII)}$, $R^{(IX)}$, $R^{(X)}$ and $R^{(XI)}$ respectively independently of each other represent hydrogen, alkyl which may be linear or branched, containing 1 to 5 carbon atoms, *—O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, wherein the residue Z respectively independently of each other represents halogen, hydroxyl, alkoxyl containing 1 to 4 carbon atoms or alkylcarboxyl containing 1 to 4 carbon atoms, preferably halogen or hydroxyl, and wherein the index p respectively independently of each other represents a whole number from 0 to 4, and (b) at least one hardened polymeric component, wherein the at least one phenalen-1-one compound with the general formula (1) is covalently and/or electrostatically bonded, preferably covalently, to the at least one hardened polymeric component.

Preferred embodiments of the article in accordance with the invention are defined herein.

The objective of the present invention is also achieved by means of the provision of a use as disclosed herein, wherein a photosensitizer composition as disclosed herein and/or a phenalen-1-one compound as disclosed herein and/or an article as disclosed herein is used for the inactivation, preferably photodynamic inactivation of microorganisms which are preferably selected from the group which consists of viruses, archaea, bacteria, bacterial spores, fungi, fungal spores, protozoa, algae and blood-borne parasites, and/or a biofilm thereof.

Preferred embodiments of the use in accordance with the invention are provided herein.

The term "biofilm" should preferably be understood to mean a matrix formed from extracellular polymeric substances (EPS), which are preferably formed by microorganisms and which are given off by them into their immediate environment adjoining the cells, in which microorganisms, preferably bacteria, algae, fungi, protozoa or combinations thereof, are at least partially disposed or embedded.

The objective of the present invention is also achieved by the provision of a method, for the inactivation, preferably for the photodynamic inactivation, of microorganisms which preferably comprise viruses, archaea, bacteria, bacterial spores, fungi, fungal spores, protozoa, algae, blood-borne parasites or combinations thereof and/or a biofilm thereof, as disclosed herein, wherein the method comprises the following steps:

(A) bringing the microorganisms and/or a biofilm thereof into contact with at least one coating which has been produced by hardening a photosensitizer composition as disclosed herein and/or which contains at least one phenalen-1-one compound as disclosed herein, and/or at least one article as disclosed herein, and (B) irradiating the microorganisms and/or a biofilm thereof and the at least one phenalen-1-one compound contained in the coating and/or the article with electromagnetic radiation of a suitable wavelength and energy density.

The term "hardening" or "setting" should preferably be understood to mean the transition from a liquid or plastic deformable state into a solid state under standard conditions (temperature: 25° C., pressure: 1013 mbar) for a substance or mixture of substances. The process of hardening or setting may preferably be carried out by cooling, i.e. reducing the temperature below the freezing point and/or glass transition temperature of a substance or mixture of substances, physical drying, i.e. by removing at least one liquid component, for example a solvent, and/or by chemical reaction, for example by chain polymerization, polyaddition and/or polycondensation.

The term "polymeric component and/or precursor thereof" should preferably be understood to mean a substance or mixture of substances which comprises at least one, preferably organic, polymer and/or at least one precursor thereof.

The term "polymer" should preferably be understood to mean a substance which is preferably constructed from at least 10 structural units, what are known as constitutional repeating units, which may be identical to or different from each other and which form the at least one organic polymer by means of a chemical reaction, preferably chain polymerization, polyaddition and/or polycondensation. Preferably, a constitutional repeating unit (CRU) is the smallest repeating group of atoms within a polymer.

A "polymer" in the context of the invention may be unbranched or branched.

The term "precursor of a polymeric component" should preferably be understood to mean monomers or mixtures of monomers as well as oligomers and mixtures thereof which can respectively combine to form the corresponding unbranched or branched polymer, preferably by chemical reaction, more preferably by chain polymerization, polyaddition and/or polycondensation.

The term "reactive functional group" should preferably be understood to mean a functional group which can contribute to the formation of the corresponding unbranched or branched 35 polymer by chemical reaction, more preferably by chain polymerization, polyaddition and/or polycondensation.

In the context of the invention, monomers or mixtures of monomers are preferably low molecular weight, reactive molecules or mixtures of reactive molecules which respectively can combine to form the corresponding unbranched or branched polymer by chemical reaction, more preferably by chain polymerization, polyaddition and/or polycondensation and thereby form the constitutional repeating unit of the polymer. Preferably, a reactive molecule, for example a monomer, oligomer and optionally polymer, comprises at least one reactive functional group.

The term "oligomer" should preferably be understood to mean a substance which is preferably built up of 2 to 9 constitutional repeating units which may be identical to or different from each other, and which preferably can combine to form an unbranched or branched polymer by chemical reaction, more preferably by chain polymerization, polyaddition and/or polycondensation.

The term "hardened polymeric component" should preferably be understood to mean a polymeric substance or a mixture of polymeric substances which is or are in a solid state under standard conditions (temperature: 25° C., pressure: 1013 mbar) and which preferably is not plastically deformable.

Regarding the definition of the terms cited above, reference should be made to Jenkins, A. D. et al.: "Glossary of basic terms in polymer science (IUPAC Recommendations 1996)" (Pure Appl. Chem. 68(12), 1996, pages 2287 to 2311, doi:10.1351/pac199668122287).

Preferably, a photosensitizer composition in accordance with the invention is formed after hardening a hardened polymer composition which contains at least one compound with formula (1) used in accordance with the invention and/or contains at least one compound with formula (Ia) in accordance with the invention.

In a preferred embodiment, upon hardening of an inventive photosensitizer composition, the at least one composition used in accordance with the invention with the formula (1) and/or the at least one composition in accordance with the invention with the formula (1a) is covalently and/or electrostatically bonded, preferably covalently, in the hardened polymer composition. More preferably, upon hardening of an inventive photosensitizer composition, the at least one composition used in accordance with the invention with the formula (1) and/or the at least one composition in accordance with the invention with the formula (1a) is covalently and/or electrostatically bonded, preferably covalently, to the at least one hardened polymeric component.

In this manner, leakage of the at least one compound with the formula (1) used in accordance with the invention and/or of the at least one compound with the formula (1a) in accordance with the invention formed from the hardened photosensitizer composition is at least partially, preferably completely prevented.

The compound with the formula (1) in accordance with the invention and the compound with the formula (1a) in accordance with the invention are respectively a 1H-phenalen-1-one derivative which will also be described as such below.

Preferably, a composition used in accordance with the invention with the formula (1) and a composition in accordance with the invention with the formula (1a) respectively comprises no neutral nitrogen atom which can be protonated, for example as an amino residue, methylamino residue or dimethylamino residue, and no positively charged, preferably quaternary, nitrogen atom, for example as a pyridin-1-ium-1-yl residue or trimethylammonio residue, as well as no positively charged, preferably quaternary, phosphorus atom, which is directly bonded to the phenalene ring.

The term "direct" as used here should be understood to mean that the nitrogen atom and/or the phosphorus atom is/are bonded directly to the phenalene ring.

The inventors have observed that when the nitrogen atom and/or phosphorus atom is/are bonded directly to the phenalene ring, the singlet oxygen quantum yield is substantially reduced.

A singlet oxygen quantum yield which is as high as possible is necessary for an antimicrobial activity in photodynamic therapy or in photodynamic cleaning or photodynamic decontamination of surfaces. In the case of a direct disposition of the nitrogen atom and/or phosphorus atom on the phenalene ring, the energy which is absorbed is emitted primarily by fluorescence effects, which leads to a significant reduction in the singlet oxygen quantum yield.

Preferably, a compound used in accordance with the invention with formula (1) and a compound in accordance with the invention with formula (1a) respectively does not have an OH group and/or deprotonated OH group which is respectively directly bonded to the phenalene ring.

The term "direct" as used here should be understood to mean that the OH group and/or the deprotonated OH group is directly bonded to the phenalene ring.

The inventors have observed that a direct disposition of an OH group and/or deprotonated OH group on the phenalene ring leads to a significant deterioration in the photostability of the photosensitizer. A deterioration in the photostability leads to faster discoloration and thus to a more rapid inactivation of the photosensitizer upon irradiation with electromagnetic radiation of a suitable wavelength.

Preferably, the term "photosensitizer" should be understood to mean compounds which absorb electromagnetic radiation, preferably visible light, UV light and/or infrared light, and therefore produce reactive oxygen species (ROS), preferably free radicals and/or singlet oxygen, from triplet oxygen.

In the context of the invention, a photosensitizer preferably has the general formula (1) and/or the general formula (1a).

The term "photodynamic decontamination" should preferably be understood to mean the light-induced inactivation of cells or microorganisms and/or a biofilm thereof on the surfaces of articles.

The term "photodynamic cleaning" should preferably be understood to mean the light-induced reduction of the number of cells or microorganisms and/or a biofilm thereof on the surfaces of articles.

The term "inactivation" in the context of the invention should be understood to mean the reduction in the viability or the destruction of a microorganism, preferably its destruction. A light-induced inactivation may, for example, be determined by a reduction in the number of microorganisms following irradiation of a defined starting quantify of these microorganisms in the presence of at least one compound in accordance with the invention with formula (1a) and/or at least one compound used in accordance with the invention with the formula (1).

Preferably, the reduction in the viability or the destruction of microorganisms of a biofilm, preferably its destruction, can reduce or prevent the release of extracellular polymeric substances which form the matrix of a biofilm. In this manner, preferably, the formation of a biofilm is slowed down or suppressed.

In accordance with the invention, the term "reduction of viability" should be understood to mean that the number of microorganisms, for example in a biofilm, is reduced by at least 90.0%, preferably at least 95.0%, preferably at least 99.9%, more preferably by at least 99.99%, more preferably by at least 99.999%, yet more preferably by at least 99.9999%. Most preferably, the number of microorganisms is reduced by more than 99.9% to 100%, preferably by more than 99.99% to 100%.

Preferably, the reduction in the number of microorganisms is given as the log 10 reduction factor, in accordance with Boyce, J. M. and Pittet, D. ("Guidelines for hand hygiene in healthcare settings. Recommendations of the Healthcare Infection Control Practices Advisory Committee and the HIPAC/SHEA/APIC/IDSA Hand Hygiene Task Force", Am.J.Infect.Control 30 (8), 2002, page 1-46).

In accordance with the invention, the term "$\log_{10}$ reduction factor" means the difference between the logarithm to base ten of the number of microorganisms before and the logarithm to base ten of the number of microorganisms after irradiating these microorganisms with electromagnetic radiation in the presence of at least one compound in accordance with the invention with the formula (1a) and/or at least one compound used in accordance with the invention with the formula (1). As an example, the microorganisms may be contained in a biofilm.

Examples of suitable methods for determining the $\log_{10}$ reduction factors are described in the standard DIN EN 14885:2007-01 "Chemische Desinfektionsmittel and Antiseptika—Anwendung Europaischer Normen für chemische Desinfektionsmittel and Antiseptika" [Chemical disinfectants and antiseptics—the application of European standards for chemical disinfectants and antiseptics] or in Rabenau, H. F. and Schwebke, I. ("Leitlinie der Deutschen Vereinigung zur Bekämpfung der Viruskrankheiten (DVV) e. V. and der Robert Koch-Instituts (RKI) zur Prüfung von chemischen Desinfektionsmitteln auf Wirksamkeit gegen Viren in der Humanmedizin" [Guidelines from the German association for the control of viral diseases (DVV) and the Robert-Koch Institute (RKI) for testing chemical disinfectants for the antiviral activity in human medicine] Bundesgesundheitsblatt, Gesundheitsforschung, Gesundheitsschutz 51(8), (2008), pages 937-945).

Preferably, the $\log_{10}$ reduction factor after irradiating microorganisms and/or a biofilm thereof with electromagnetic radiation in the presence of at least one compound in accordance with the invention with the formula (1a) and/or at least one compound used in accordance with the invention with the formula (1) is at least 1 $\log_{10}$, preferably at least 2 $\log_{10}$, preferably at least 3 $\log_{10}$, more preferably at least 4 $\log_{10}$, more preferably at least 4.5 $\log_{10}$, more preferably at least 5 $\log_{10}$, more preferably at least 6 $\log_{10}$, yet more preferably at least 7 $\log_{10}$.

As an example, a reduction in the number of microorganisms after irradiating these microorganisms and/or a biofilm thereof with electromagnetic radiation in the presence of at least one compound in accordance with the invention with the formula (1a) and/or at least one compound used in accordance with the invention with the formula (1) is approximately 2 powers of ten, with respect to the initial quantity of these microorganisms, namely a $\log_{10}$ reduction factor of 2 $\log_{10}$.

More preferably, the number of microorganisms after irradiating these microorganisms and/or a biofilm thereof with electromagnetic radiation in the presence of at least one compound in accordance with the invention with the formula (1a) and/or at least one compound used in accordance with the invention with the formula (1) is reduced by at least 1 power of ten, more preferably by at least 2 powers of ten, preferably by at least 4 powers of ten, more preferably by at least 5 powers of ten, more preferably by at least 6 powers of ten, yet more preferably by at least 7 powers of ten, respectively with respect to the initial quantity of these microorganisms.

The term "microorganisms" as used in the context of the invention should in particular be understood to mean viruses, archaea, or prokaryotic microorganisms, such as fungi, protozoa, fungal spores, single-celled algae. The microorganisms may in this regard be single-celled or multi-celled, for example as a fungal mycelium.

In accordance with the invention, the term "halogen" should be understood to mean, respectively independently of each other, fluorine, chlorine, bromine or iodine. In accordance with the invention, the term "halide" should be understood to mean, respectively independently of each other, fluoride, chloride, bromide or iodide.

Unless stated otherwise, chiral centres may be in the R- or in the S-configuration. The invention concerns both the optically pure compounds as well as stereoisomeric mixtures such as enantiomeric mixtures and diastereoisomeric mixtures in any proportions.

Preferably, the invention also concerns mesomers and/or tautomers of the compound with the formula (1) and/or with the formula (1a), both the pure compounds and also the isomeric mixtures in any proportions.

Unless stated otherwise, a "*" in a formula designates a linkage between two residues.

An inventive, preferably hardenable, photosensitizer composition comprises:

(a) at least one phenalen-1-one compound for use in accordance with the invention with the general formula (1):

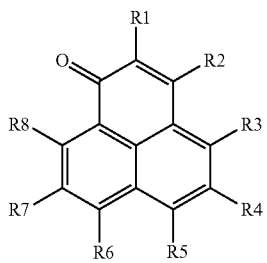

(1)

and (b) at least one polymeric component and/or precursor thereof.

A phenalen-1-one compound for use in accordance with the invention has the general formula (1), wherein the residues R1 to R8, which respectively independently of one another may be identical to or different from each other, respectively represent hydrogen, halogen, alkyl containing 1 to 12 C atoms, preferably 2 to 9 C atoms, alkylaryl containing 5 to 20 C atoms, preferably 6 to 9 C atoms, aryl containing 5 to 20 C atoms, preferably 6 to 9 C atoms, *—O-alkyl containing 1 to 12 C atoms, preferably 2 to 9 C atoms, *—O-alkylaryl containing 5 to 20 C atoms, preferably 6 to 9 C atoms, *—O-aryl containing 5 to 20 C atoms, preferably 6 to 9 C atoms, ether containing 2 to 12 C atoms, a residue with the formula *—O—C(=O)—R$^{(Ia)}$, a residue with the formula *—C(=O)—R$^{(Ib)}$, or an organic residue W1 which contains at least one reactive functional group, with the proviso that at least one of the residues R1 to R7, preferably at least one of the residues R1, R2, R5 or R6, more preferably at least one of the residues R1 or R2, preferably one of the residues R1 or R2, is an organic residue W1, wherein the organic residue W1 respectively independently of each other represents a residue with the general formula (2) to (6):

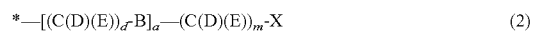 (2)

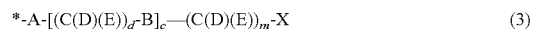 (3)

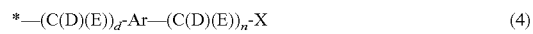 (4)

 (5)

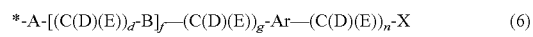 (6)

wherein the residue A respectively independently of each other represents oxygen, sulphur or a residue with the general formula (10a) to (11a), preferably oxygen or a residue with the general formula (10a) to (11a), more preferably oxygen or a residue with the general formula (10a), more preferably oxygen:

(10a)

(11a)

wherein *$^{ph}$ respectively denotes a linkage from the residue with the general formula (10a) to (11a) to a C atom of the phenalene ring and *$^c$ respectively denotes a linkage from the residue with the general formula (10a) to (11a) to a C atom of the residue (C(D)(E)), wherein the residue B respectively independently of each other represents oxygen, sulphur or a residue with the general formula (10) to (14), preferably oxygen or a residue with the general formula (10) to (14), more preferably oxygen or a residue with the general formula (10):

(10)

(11)

-continued

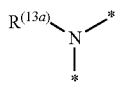
(12)

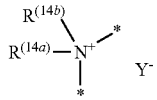
(13)

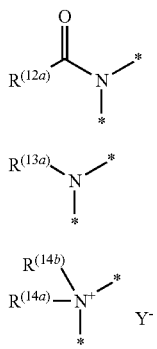
(14)

wherein the residues $R^{(Ia)}$, $R^{(Ib)}$, $R^{(11a)}$, $R^{(12a)}$, $R^{(13a)}$, $R^{(14a)}$ and $R^{(14b)}$, respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group which consists of halogen, amino, hydroxyl, alkyl which may be linear or branched, containing 1 to 3 carbon atoms, hydroxyalkyl which may be linear or branched, containing 1 to 3 carbon atoms and 1 to 3 OH groups, halogenoalkyl which may be linear or branched, containing 1 to 3 carbon atoms and 1 to 3 halogen groups, and combinations thereof, preferably chlorine, bromine, fluorine, methyl, ethyl, n-propyl, iso-propyl, methoxy, ethoxy, and combinations thereof, wherein $Y^-$ is an anion which respectively independently of each other represents fluoride, chloride, bromide, iodide, sulphate, hydrogen sulphate, phosphate, hydrogen phosphate, dihydrogen phosphate, at least one carboxylate anion of a carboxylic acid containing 1 to 15 carbon atoms, at least one sulphonate anion of a sulphonic acid containing 1 to 12 C atoms, or a combination thereof, and wherein the residues D and E respectively independently of each other represent hydrogen, halogen, hydroxyl, alkyl which may be linear or branched, containing 1 to 5 carbon atoms, hydroxyalkyl which may be linear or branched, containing 1 to 5 carbon atoms and 1 to 5 OH groups, phenyl, benzyl, a residue with the formula *-L-$R^{(II)}$, a residue with the formula *-L-C(=L)-$R^{(III)}$, a residue with the formula *—(CH$_2$)$_q$—X, a residue with the formula *-L-(CH$_2$)$_q$—X, or a residue with the formula *—(CH$_2$)$_s$-L-(CH$_2$)$_t$—X, wherein the residue L respectively independently of each other represents oxygen or sulphur, preferably oxygen, wherein the residues $R^{(II)}$ and $R^{(III)}$ respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, the indices q, s and t respectively independently of each other representing a whole number from 1 to 5, wherein the indices a, c, f, g and n respectively independently of each other represent a whole number from 0 to 5, preferably from 1 to 4, and wherein the indices b, d and m respectively independently of each other represent a whole number from 1 to 5, preferably from 2 to 4, wherein the residue Ar respectively independently of each other represents a substituted or unsubstituted aromatic compound or a substituted or unsubstituted heteroaromatic compound, and wherein the residue X respectively independently of each other is a reactive functional group denoted by *—N($R^{(VI)}$)($R^{(VII)}$), *—OH, *—SH, *—NCO, *—NCS, *—Si($R^{(VIII)}$)($R^{(IX)}$)—[O—Si($R^{(X)}$)($R^{(XI)}$)$_p$]—Z, or a residue with the general formula (20) to (24):

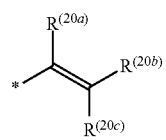
(20)

(21)

(22)

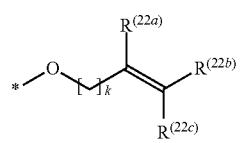
(23)

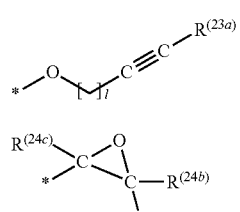
(24)

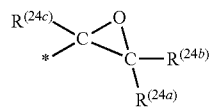

wherein the residues $R^{(20a)}$, $R^{(20b)}$, $R^{(20c)}$, $R^{(21a)}$, $R^{(22a)}$, $R^{(22b)}$, $R^{(22c)}$, $R^{(23a)}$, $R^{(24a)}$, $R^{(24b)}$, and $R^{(24c)}$ respectively independently of each other, represent hydrogen, methyl, ethyl, n-propyl, iso-propyl, n-butyl, sec-butyl, iso-butyl, or n-pentyl, preferably hydrogen, methyl or ethyl, and wherein the indices l and k respectively independently of each other represent a whole number from 0 to 4, wherein the residues $R^{(VI)}$, $R^{(VII)}$, $R^{(VIII)}$, $R^{(IX)}$, $R^{(X)}$ and $R^{(XI)}$ respectively independently of each other represent hydrogen, alkyl which may be linear or branched, containing 1 to 5 carbon atoms, *—O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, wherein the residue Z respectively independently of each other represents halogen, hydroxyl, alkoxyl containing 1 to 4 carbon atoms or alkylcarboxyl containing 1 to 4 carbon atoms, and wherein the index p respectively independently of each other represents a whole number from 0 to 4.

Preferably, at least one of the residues R1 to R7, more preferably at least one of the residues R1, R2, R5 or R6, more preferably at least one of the residues R1 or R2, preferably one of the residues R1 or R2, of the at least one phenalen-1-one compound to be used in accordance with the invention with the general formula (1) respectively independently of each other represents an organic residue W1, wherein the at least one organic residue W1 respectively independently of each other represents a residue with the general formula (2) to (6) and wherein the residue Ar respectively independently of each other represents an unsubstituted or substituted phenyl residue, an unsubstituted or substituted pyridine residue, an unsubstituted or substituted biphenyl residue, an unsubstituted or substituted diphenylpropyl residue or an unsubstituted or substituted bisphenylsulphonyl residue, preferably a residue with the general formula (25a) to (31), more preferably a residue with the general formula (25a) to (28b):

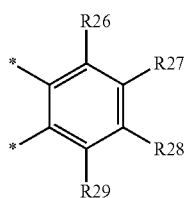
(25a)

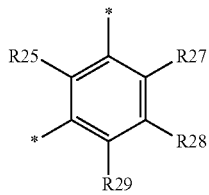
(25b)

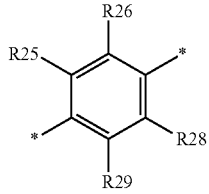
(25c)

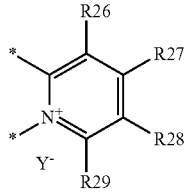
(26a)

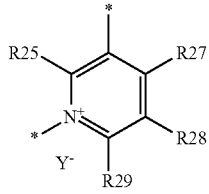
(26b)

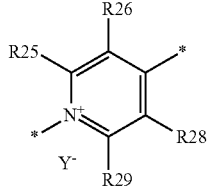
(26c)

-continued

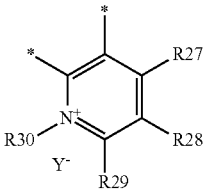
(27a)

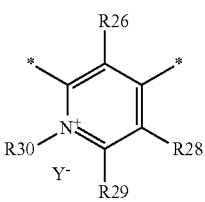
(27b)

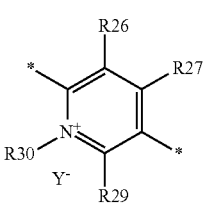
(27c)

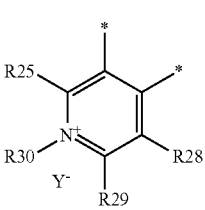
(27d)

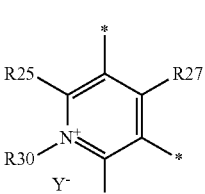
(27e)

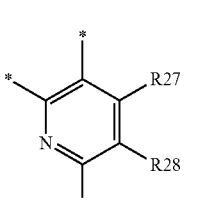
(28a)

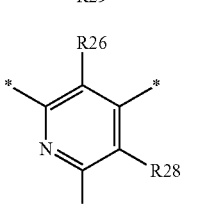
(28b)

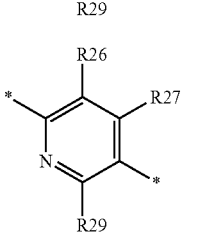
(28c)

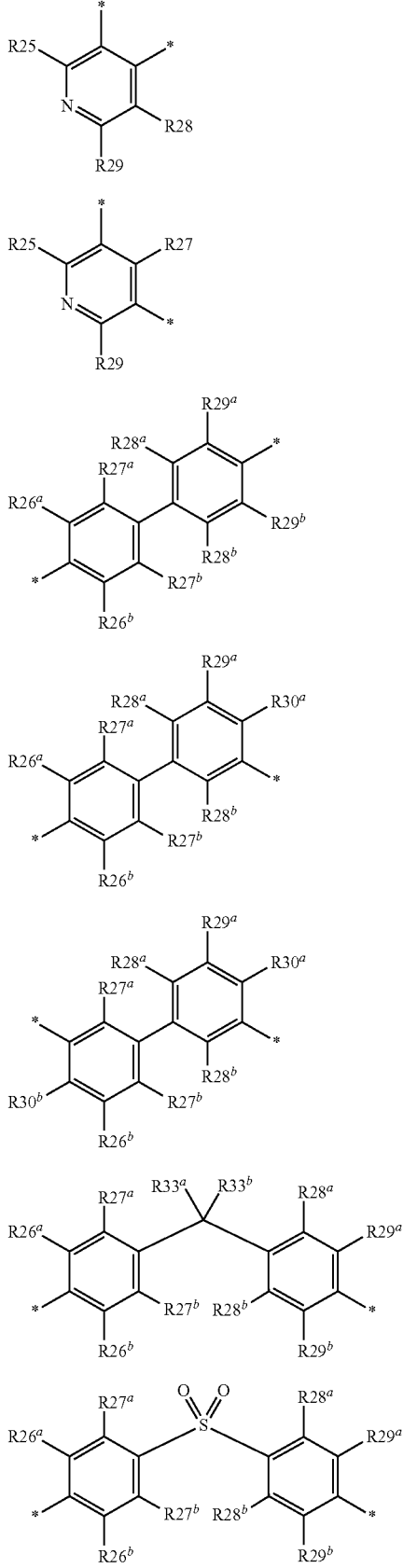

wherein the residues R25, R26, R27, R28, R29, $R26^a$, $R26^b$, $R27^a$, $R27^b$, $R28^a$, $R28^b$, $R29^a$, $R29^b$, $R30^a$ and $R30^b$ respectively independently of each other represent hydrogen, hydroxy, amino, alkyl which may be linear or branched, containing 1 to 5 carbon atoms, *—O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, and wherein the residue R30 respectively independently of each other represents hydrogen or alkyl which may be linear or branched, containing 1 to 5 carbon atoms, and wherein the residues $R33^a$ and $R33^b$ respectively independently of each other represent hydrogen, hydroxy, amino, alkyl which may be linear or branched, containing 1 to 5 carbon atoms, perfluoralkyl which may be linear or branched, containing 1 to 5 carbon atoms, *—O-alkyl which may be linear or branched, containing 1 to 5 carbon atoms, phenyl, benzyl or, when taken together, a cycloalkyl which may be linear or branched, containing 4 to 9 carbon atoms, or a 9H-fluoren-9-ylidene residue, and wherein $Y^-$ is an anion which respectively independently of each other represents fluoride, chloride, bromide, iodide, sulphate, hydrogen sulphate, phosphate, hydrogen phosphate, dihydrogen phosphate, at least one carboxylate anion of a carboxylic acid containing 1 to 15 carbon atoms, at least one sulphonate anion of a sulphonic acid containing 1 to 12 C atoms, or a combination thereof.

Preferably, at least one of the residues R1 to R7, more preferably at least one of the residues R1, R2, R5 or R6, more preferably at least one of the residues R1 or R2, more preferably one of the residues R1 or R2, of the at least one phenalen-1-one compound to be used in accordance with the invention with the general formula (1) respectively independently is an organic residue W1, wherein the at least one organic residue W1 respectively independently of each other represents a residue with the general formula (40) to (67), or (72) to (98e), preferably a residue with the general formula (40) to (67) or (72) or (97):

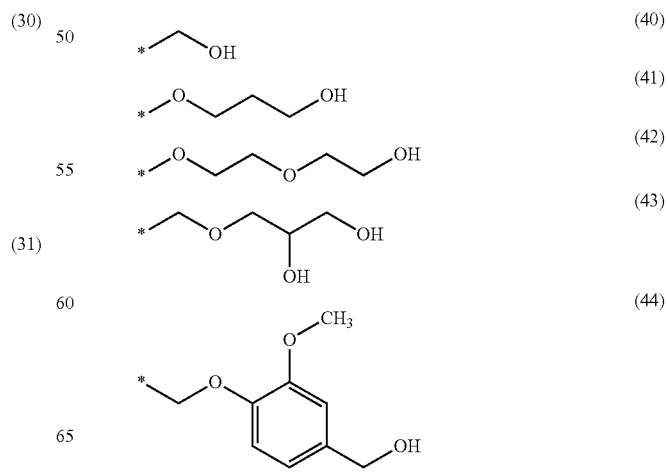

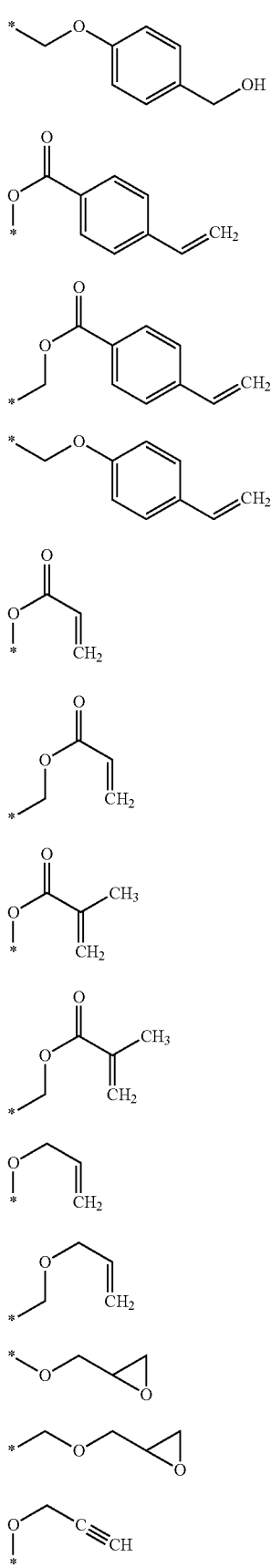
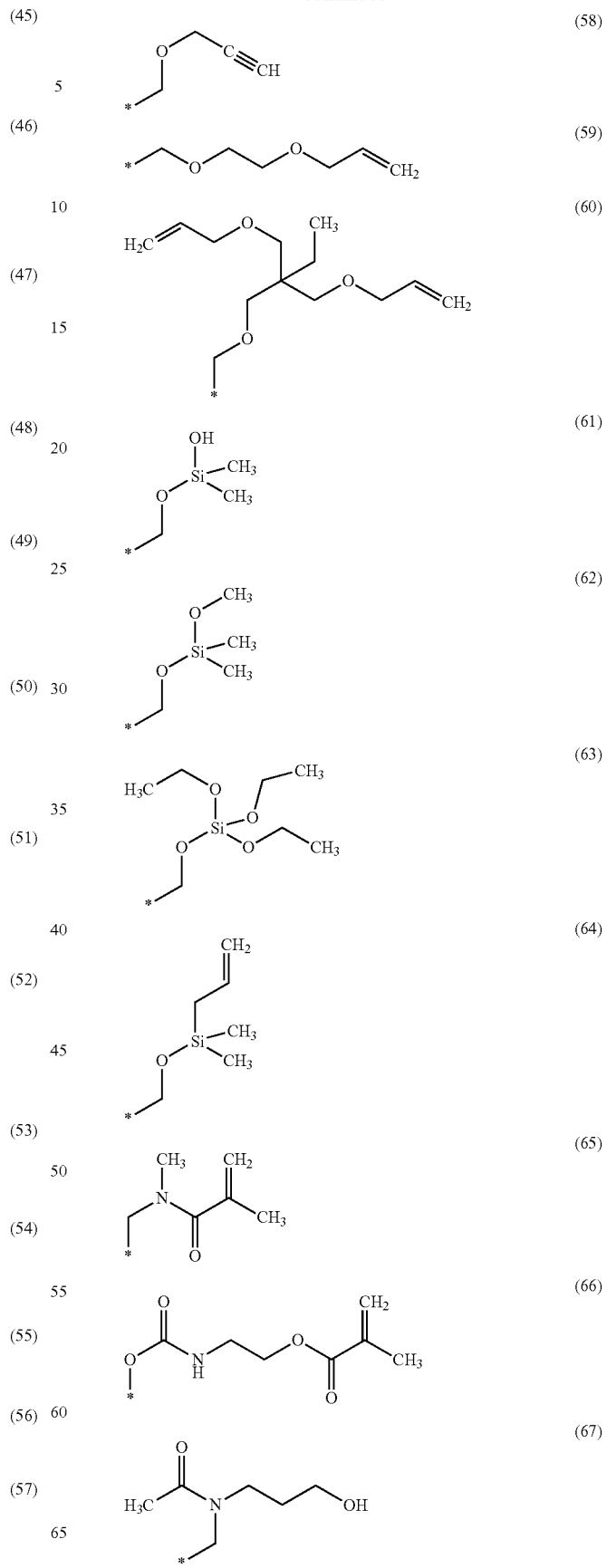

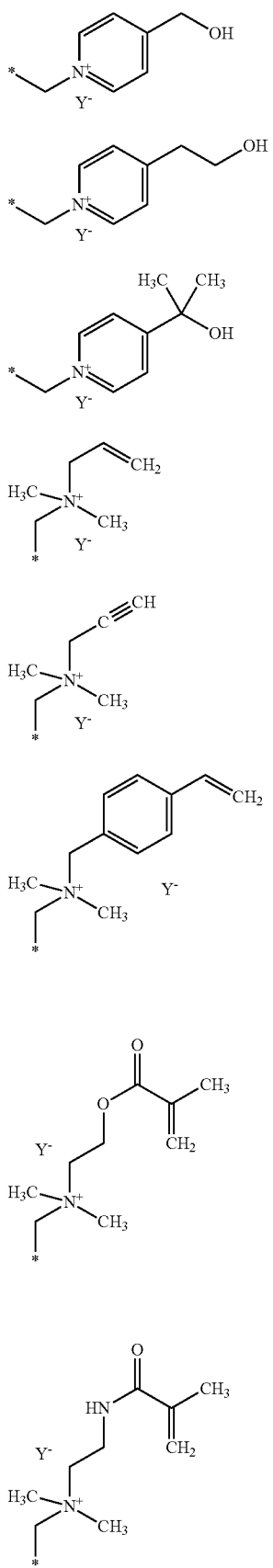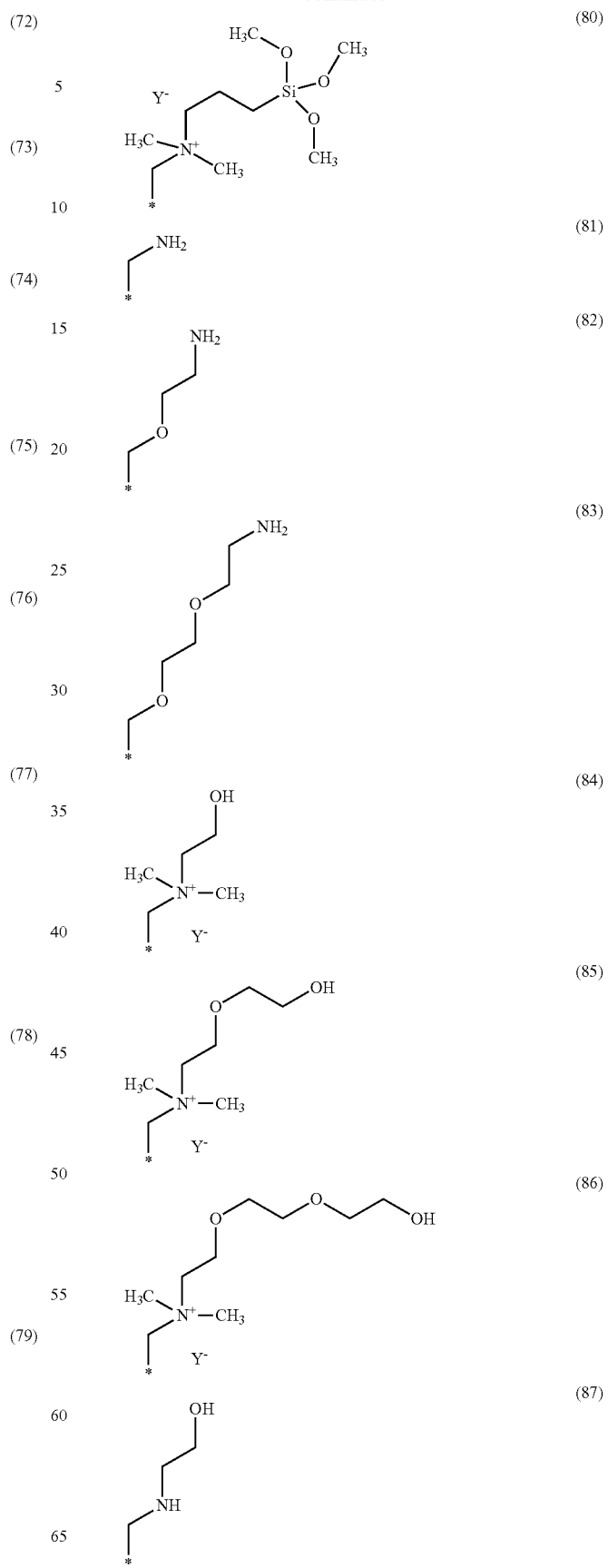

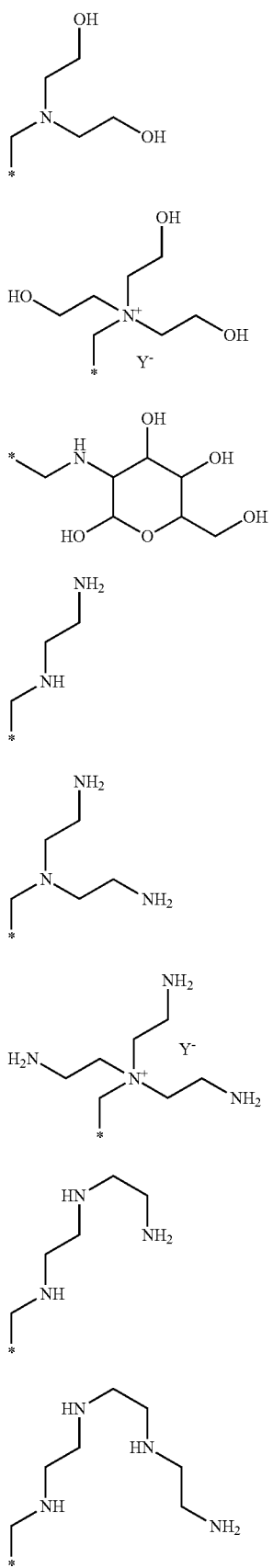
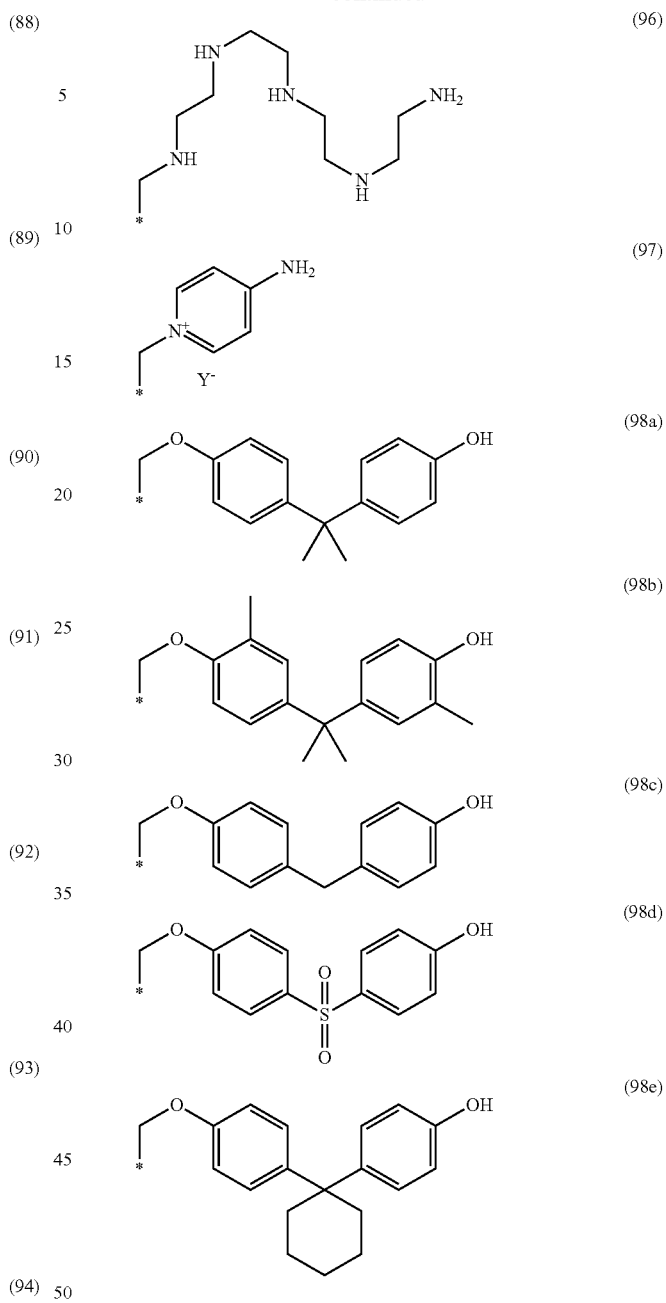

wherein Y⁻ is an anion which respectively independently of each other represents fluoride, chloride, bromide, iodide, sulphate, hydrogen sulphate, phosphate, hydrogen phosphate, dihydrogen phosphate, at least one carboxylate anion of a carboxylic acid containing 1 to 15 carbon atoms, at least one sulphonate anion of a sulphonic acid containing 1 to 12 C atoms, or a combination thereof.

More preferably, the at least one phenalen-1-one compound for use in accordance with the invention with the general formula (1) is respectively independently selected from the group which consists of compounds with formula (100) to (127), (132) to (166) and combinations thereof, preferably from compounds with formula (100) to (127), (132) to (161) and combinations thereof:

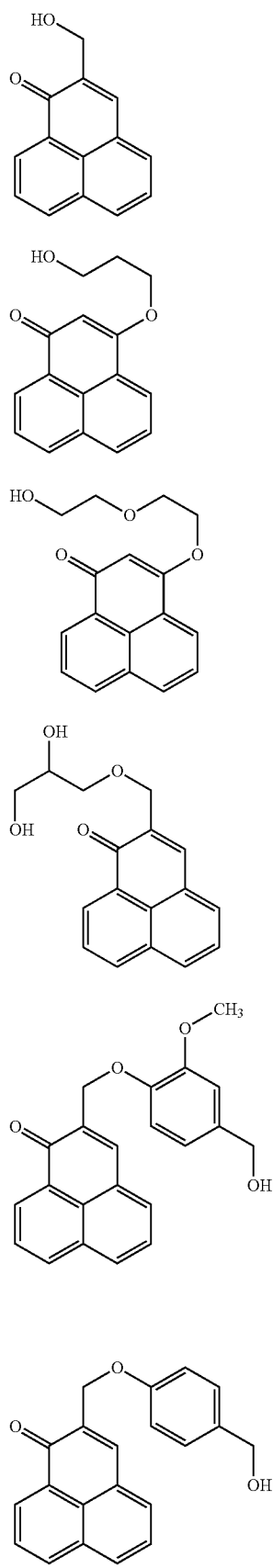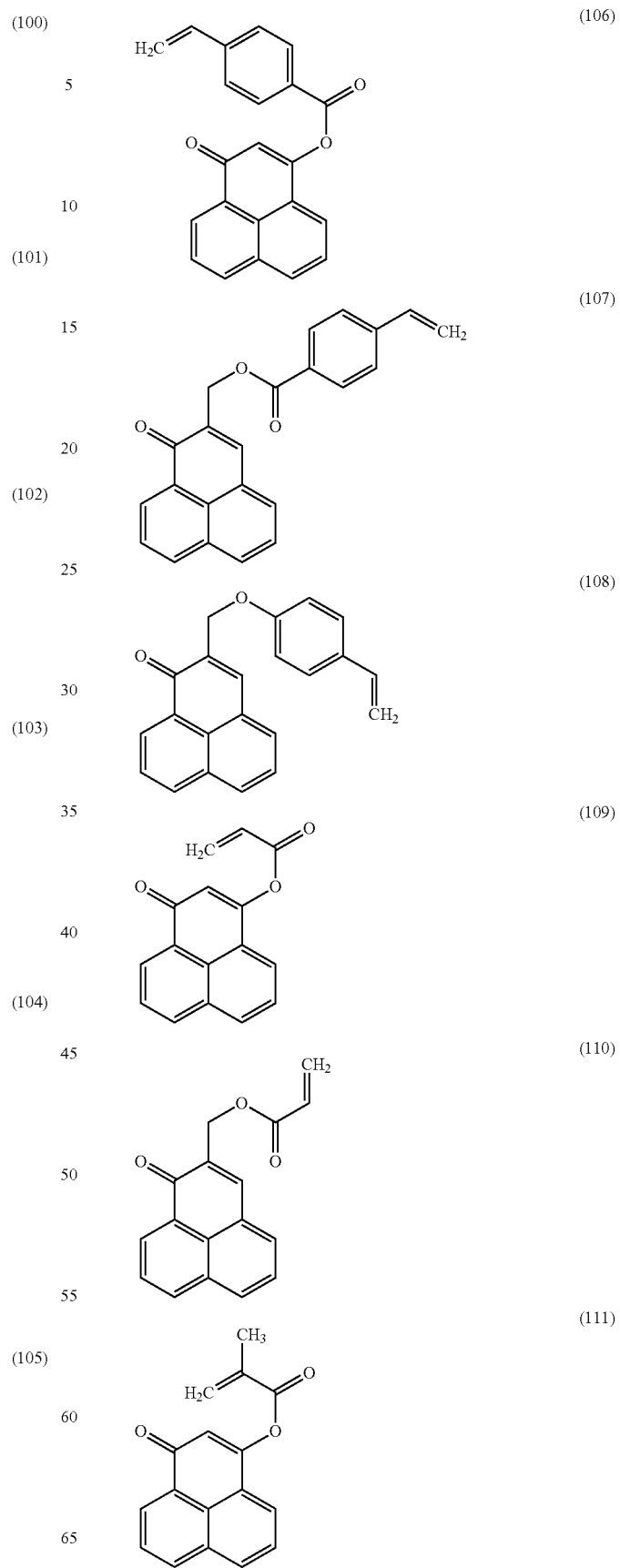

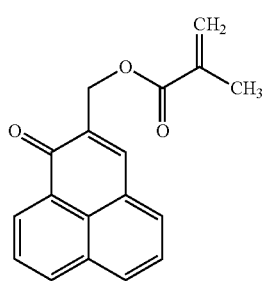
(112)
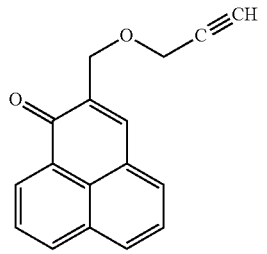
(118)
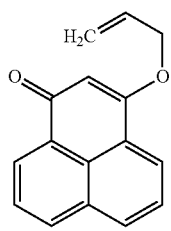
(113)
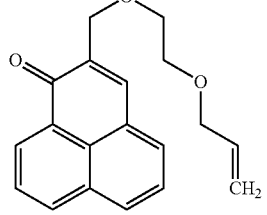
(119)
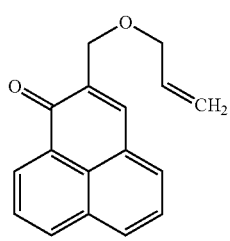
(114)
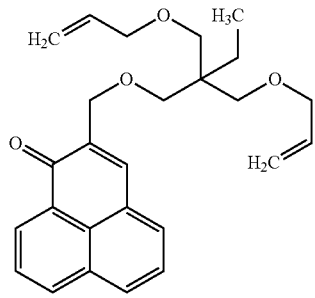
(120)
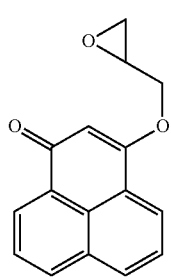
(115)
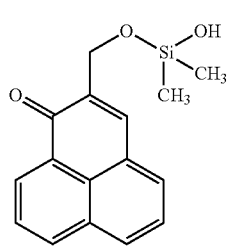
(121)
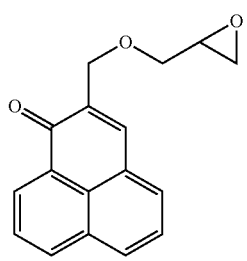
(116)
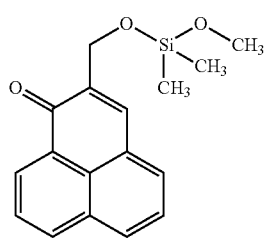
(122)
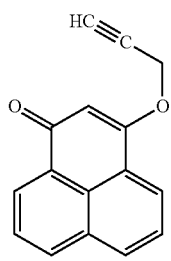
(117)
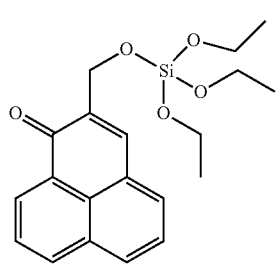
(123)

(124) 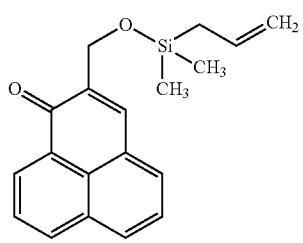
(125) 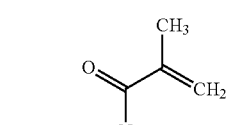
(126) 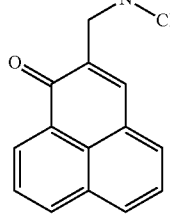
(127) 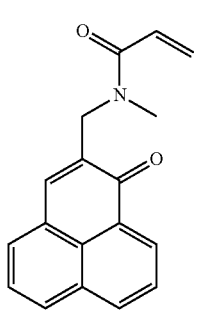
(132) 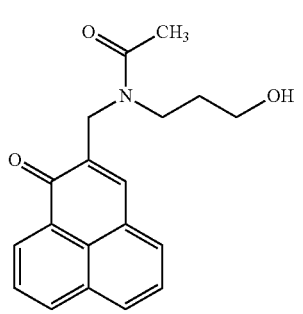
(133) 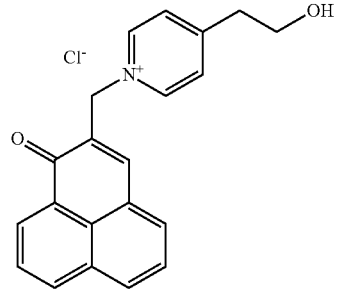
(134) 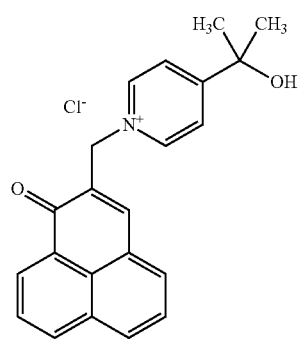
(135) 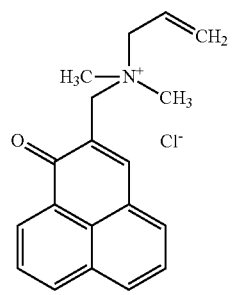
(136) 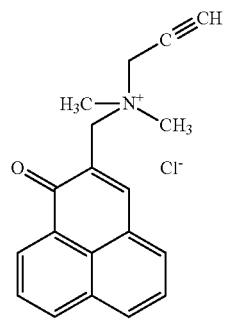
(137) 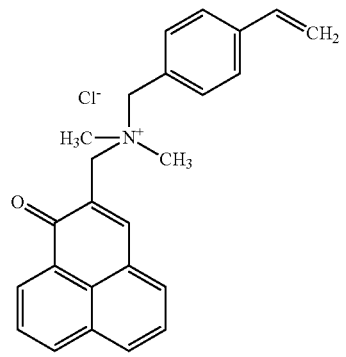

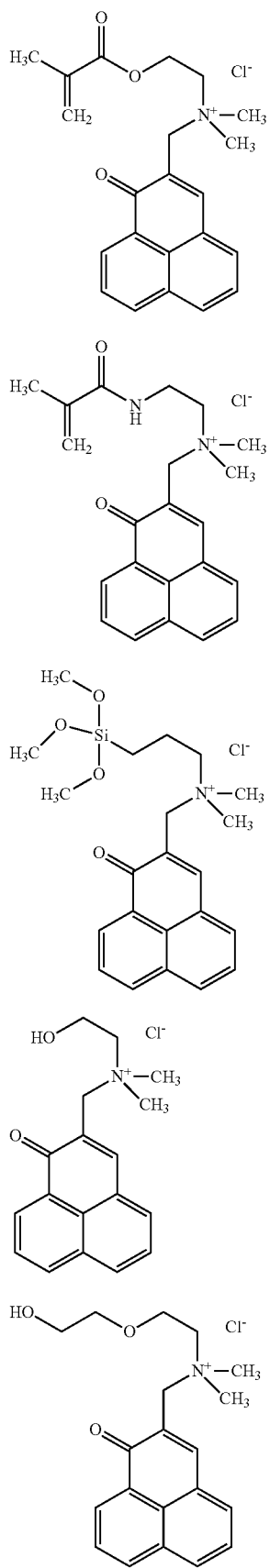
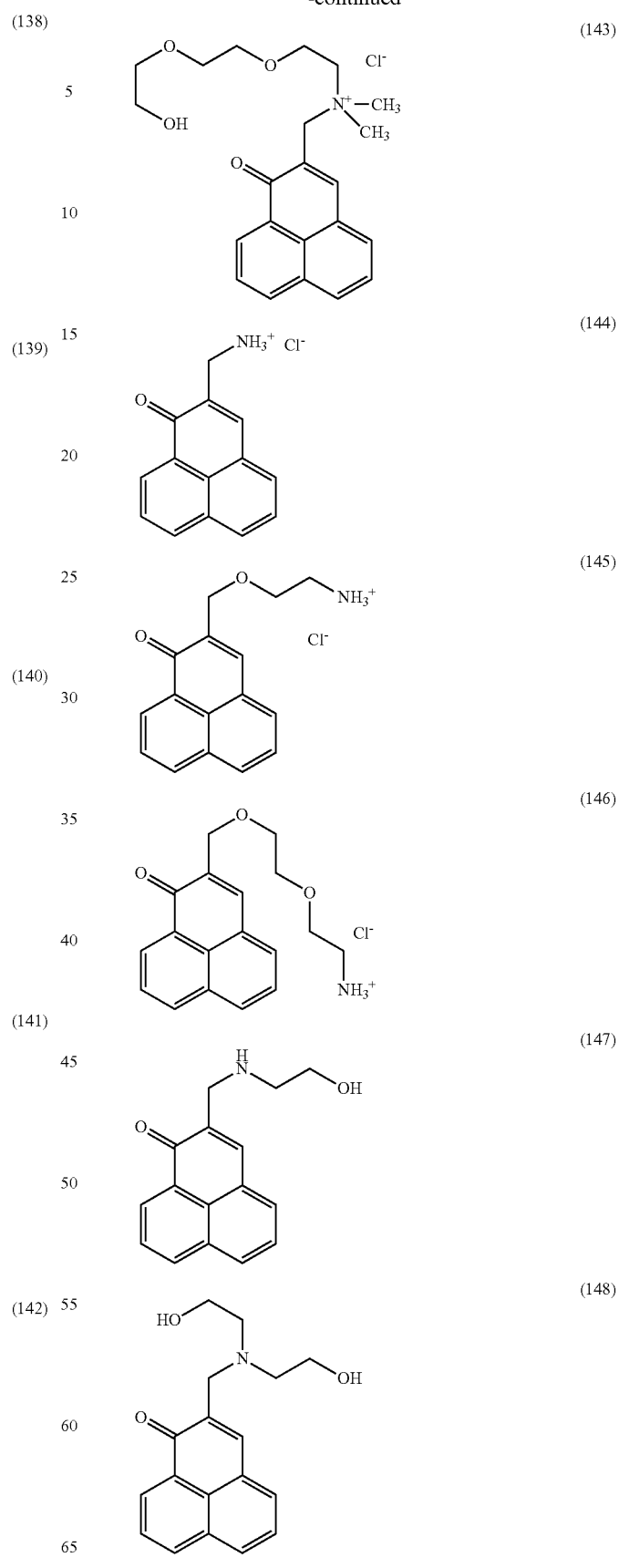

(149) 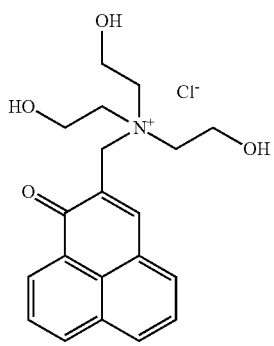
(150) 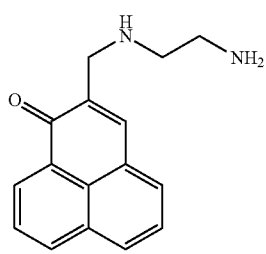
(151) 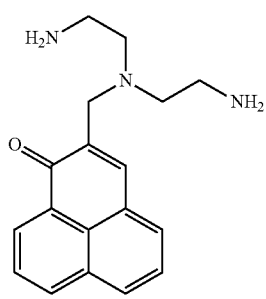
(152) 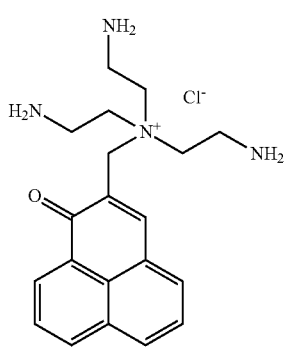
(153) 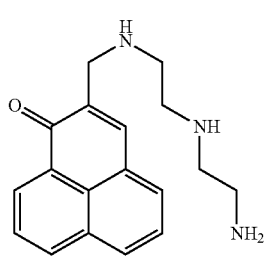
(154) 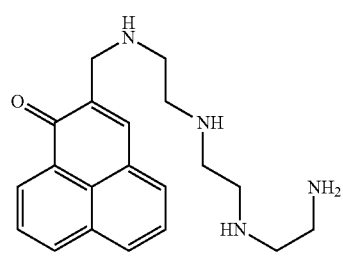
(155) 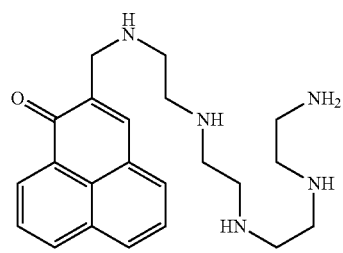
(156) 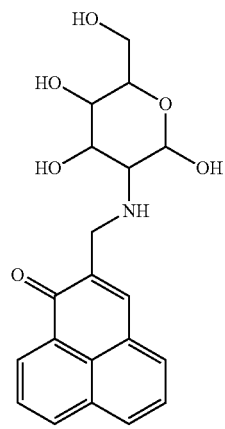
(157) 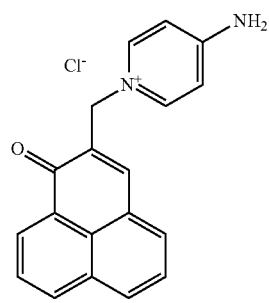
(158) 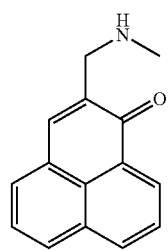

(159) 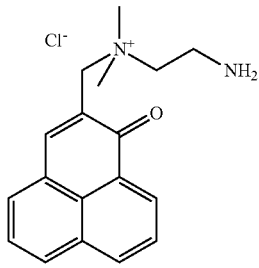

(160) 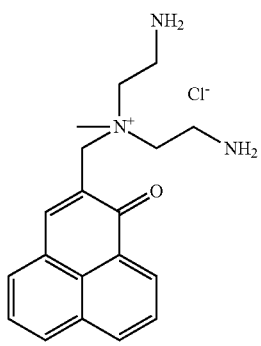

(161) 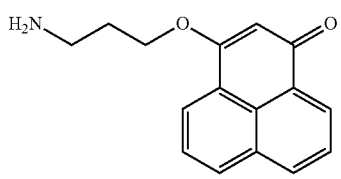

(162) 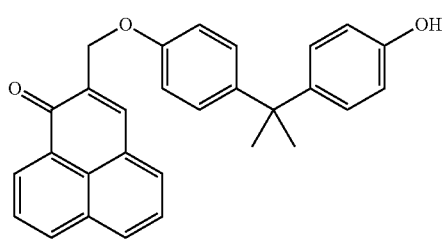

(163) 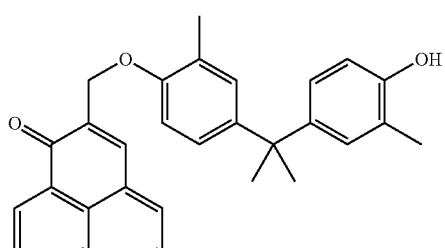

(164) 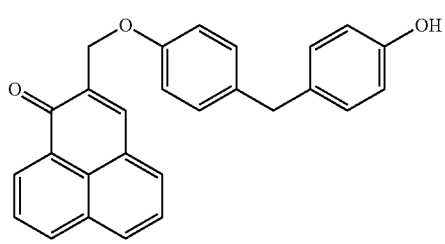

(165) 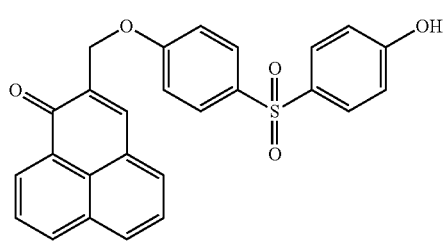

(166) 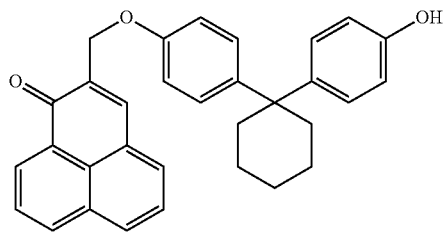

More preferably, a photosensitizer composition in accordance with the invention comprises
(a) at least one phenalen-1-one compound in accordance with the invention with the general formula (1a), and
(b) at least one polymeric component and/or precursor thereof.

An inventive phenalen-1-one compound has the general formula (1a):

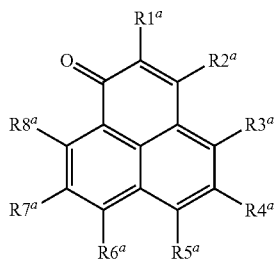

(1a)

wherein the residues $R1^a$ to $R8^a$, which respectively independently of one another may be identical to or different from each other, respectively represent hydrogen, halogen, alkyl containing 1 to 12 C atoms, preferably 2 to 9 C atoms, alkylaryl containing 5 to 20 C atoms, preferably 6 to 9 C atoms, aryl containing 5 to 20 C atoms, preferably 6 to 9 C atoms, *—O-alkyl containing 1 to 12 C atoms, preferably 2 to 9 C atoms, *—O-alkylaryl containing 5 to 20 C atoms, preferably 6 to 9 C atoms, *—O-aryl containing 5 to 20 C atoms, preferably 6 to 9 C atoms, ether containing 2 to 12 C atoms, a residue with the formula *—O—C(=O)—$R^{(Ia)}$, a residue with the formula *—C(=O)—$R^{(Ib)}$, or an organic residue W1a which contains at least one reactive functional group, with the proviso that at least one of the residues $R1^a$ or $R2^a$, preferably one of the residues $R1^a$ or $R2^a$, is an organic residue W1a, wherein the organic residue W1a respectively independently of each other represents a residue with the general formula (2a) to (6a), $$*-[(C(D)(E))_d\text{-}B]_e-(C(D)(E))_m\text{-}X^a \qquad (2a)$$

$$*\text{-}A\text{-}[(C(D)(E))_d\text{-}B]_e-(C(D)(E))_m\text{-}X^a \qquad (3a)$$

*—(C(D)(E))$_d$-Ar—(C(D)(E))$_n$-X$^a$ (4a)

*—[(C(D)(E))$_d$-B]$_b$—(C(D)(E))$_g$-Ar—(C(D)(E))$_n$-X$^a$ (5a)

*-A-[(C(D)(E))$_d$-B]$_f$—(C(D)(E))$_g$-Ar—(C(D)(E))$_n$-X$^a$ (6a)

wherein residue A respectively independently of each other represents oxygen, sulphur or a residue with the general formula (10a) to (11a), preferably oxygen or a residue with the general formula (10a), more preferably oxygen:

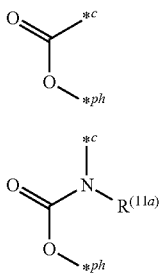

(10a)

(11a)

and wherein *$^{ph}$ respectively denotes a linkage from the residue with the general formula (10a) to (11a) to a C atom of the phenalene ring and *$^c$ respectively denotes a linkage from the residue with the general formula (10a) to (11a) to a C atom of the residue (C(D)(E)), wherein the residue B respectively independently of each other represents oxygen, sulphur or a residue with the general formula (10) to (12), preferably oxygen or a residue with formula (10) or (11), more preferably oxygen or a residue with formula (10):

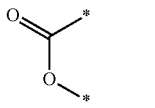

(10)

(11)

(12)

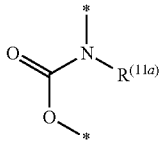

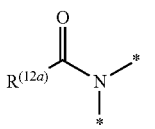

and wherein the residues R$^{(Ia)}$, R$^{(Ib)}$, R$^{(11a)}$ and R$^{(12a)}$ respectively independently of each other represent methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, and wherein the residues D and E respectively independently of each other represent hydrogen, halogen, hydroxyl, alkyl which may be linear or branched, containing 1 to 5 carbon atoms, hydroxyalkyl which may be linear or branched, containing 1 to 5 carbon atoms and 1 to 5 OH groups, phenyl, benzyl, a residue with the formula *-L-R$^{(II)}$, a residue with the formula *-L-C(=L)-R$^{(III)}$, a residue with the formula *—(CH$_2$)$_q$—X, a residue with the formula *-L-(CH$_2$)$_q$—X, or a residue with the formula *—(CH$_2$)$_s$-L-(CH$_2$)$_t$—X, wherein the residue L respectively independently of each other represents oxygen or sulphur, preferably oxygen, wherein the residues R$^{(II)}$ and R$^{(III)}$ respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, the indices q, s and t respectively independently of each other representing a whole number from 1 to 5, wherein the indices c, g, f and n respectively independently of each other represent a whole number from 0 to 5, preferably from 1 to 4, and wherein the indices b, d, e and m respectively independently of each other represent a whole number from 1 to 5, preferably from 2 to 4, wherein the residue Ar respectively independently of each other represents a substituted or unsubstituted aromatic compound or a substituted or unsubstituted heteroaromatic compound which contains no N atoms, and wherein the residue X$^a$ respectively independently of each other is a reactive functional group denoted by *—OH, *—SH, *—NCO, *—NCS, *—Si(R$^{(VIII)}$)(R$^{(IX)}$)—[O—Si(R$^{(X)}$)(R$^{(XI)}$)]$_p$—Z, or a residue with the general formula (20) to (24):

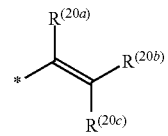

(20)

(21)

(22)

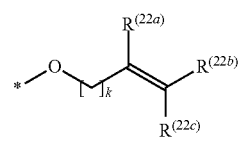

(23)

(24)

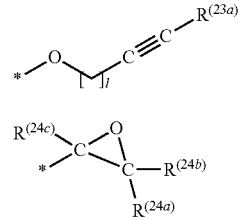

wherein the residues R$^{(20a)}$, R$^{(20b)}$, R$^{(20c)}$, R$^{(21a)}$, R$^{(22a)}$, R$^{(22b)}$, R$^{(22c)}$, R$^{(23a)}$, R$^{(24a)}$, R$^{(24b)}$, and R$^{(24c)}$ respectively independently of each other, represent hydrogen, methyl, ethyl, n-propyl, iso-propyl, n-butyl, sec-butyl, iso-butyl, or n-pentyl, preferably hydrogen, methyl or ethyl, and wherein the indices l and k respectively independently of each other represent a whole number from 0 to 4, wherein the residues $R^{(VII)}$, $R^{(IX)}$, $R^{(X)}$ and $R^{(XI)}$ respectively independently of each other represent hydrogen, alkyl which may be linear or branched, containing 1 to 5 carbon atoms, *—O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, wherein the residue Z respectively independently of each other represents halogen or hydroxyl, and wherein the index p respectively independently of each other represents a whole number from 0 to 4.

Preferably, at least one of the residues $R1^a$ or $R2^a$ of the inventive phenalen-1-one compound with the general formula (1a) respectively independently of each other is at least one organic residue W1a, wherein the at least one organic residue W1a respectively independently of each other represents a residue with the general formula (2a) to (6a) and wherein the residue Ar respectively independently of each other represents an unsubstituted or substituted phenyl residue, an unsubstituted or substituted biphenyl residue, an unsubstituted or substituted diphenylpropyl residue or an unsubstituted or substituted bisphenylsulphonyl residue, preferably a residue with the general formula (25a) to (25c), (29a) to (29c), (30) or (31), preferably a residue with the general formula (25a) to (25c):

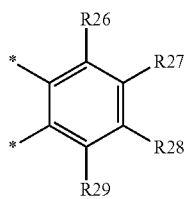
(25a)

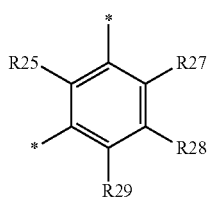
(25b)

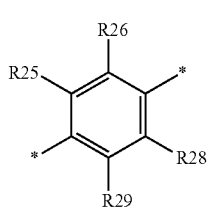
(25c)

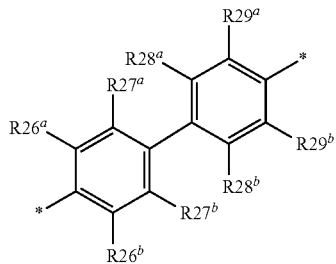
(29a)

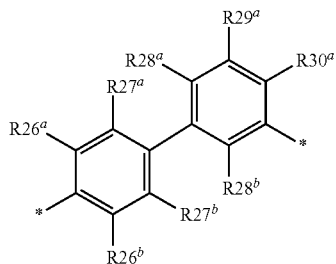
(29b)

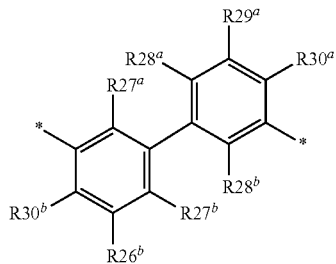
(29c)

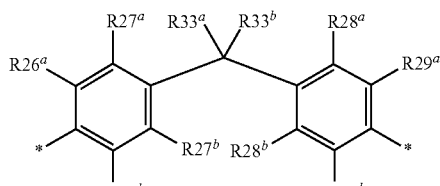
(30)

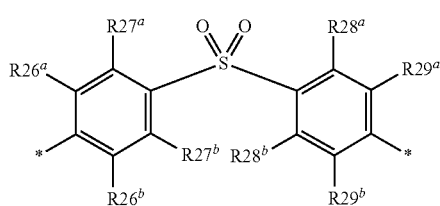
(31)

wherein the residues R25, R26, R27, R28, R29, $R26^a$, $R26^b$, $R27^a$, $R27^b$, $R28^a$, $R28^b$, $R29^a$, $R29^b$, $R30^a$ and $R30^b$ respectively independently of each other represent hydrogen, hydroxy, alkyl which may be linear or branched, containing 1 to 5 carbon atoms, perfluoralkyl which may be linear or branched, containing 1 to 5 carbon atoms, *—O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, and wherein the residues $R33^a$ and $R33^b$ respectively independently of each other represent hydrogen, hydroxy, alkyl which may be linear or branched, containing 1 to 5 carbon atoms, perfluoralkyl which may be linear or branched, containing 1 to 5 carbon atoms, *—O-alkyl which may be linear or branched, containing 1 to 5 carbon atoms, phenyl, benzyl or, when taken together, a cycloalkyl which may be linear or branched, containing 4 to 9 carbon atoms, or a 9H-fluoren-9-ylidene residue.

More preferably, the at least one organic residue W1a of the inventive phenalen-1-one compound with the general formula (1a) is respectively independently of each other selected from the group which consists of residues with the general formula (41) to (67), (98a) to (98e) and combinations thereof, preferably residues with the general formula (41) to (67) and combinations thereof:

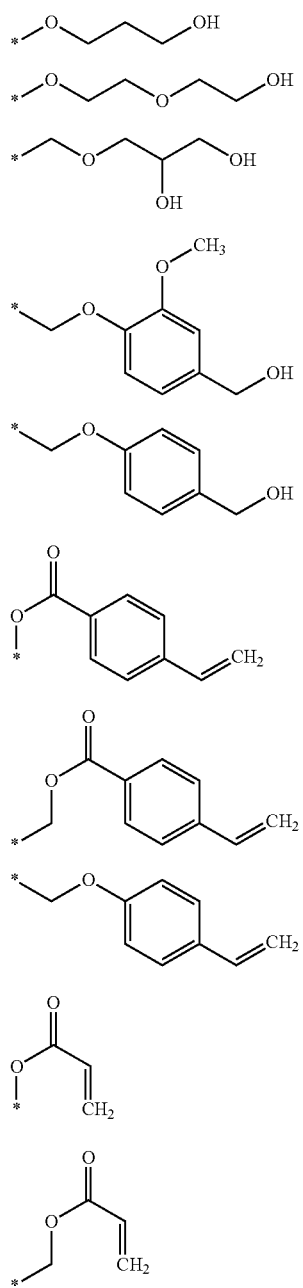

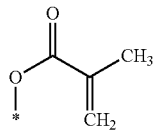

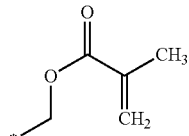

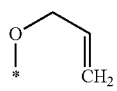

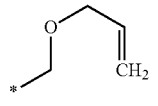

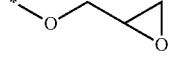

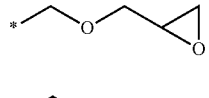

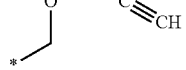

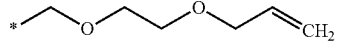

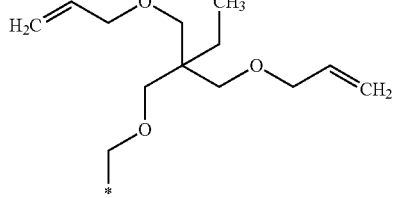

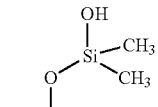

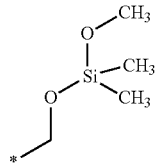

-continued
(63) 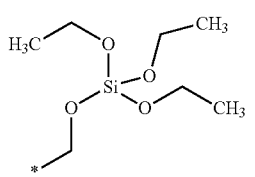
(64) 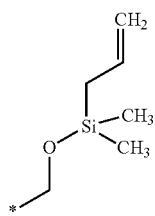
(65) 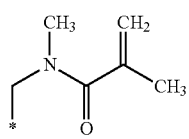
(66) 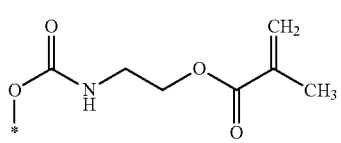
(67) 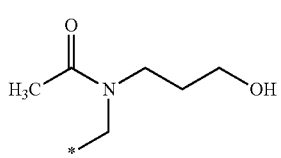
(98a) 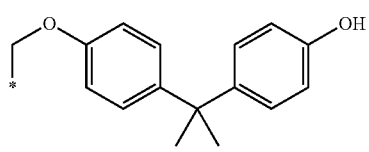
(98b) 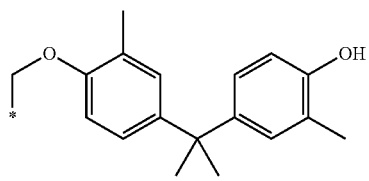
(98c) 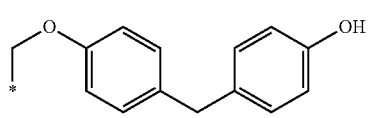
(98d) 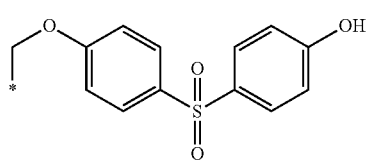
-continued
(98e) 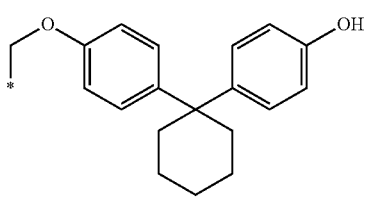
More preferably, a phenalen-1-one compound in accordance with the invention with the general formula (Ia) is selected from the group which consists of compounds with formula (101) to (127), (162) to (166) and combinations thereof, preferably from compounds with formula (101) to (127) and combinations thereof:
(101) 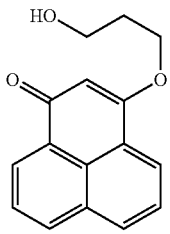
(102) 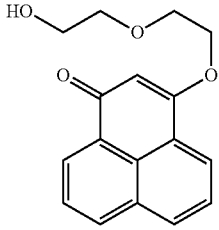
(103) 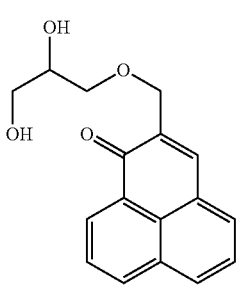
(104) 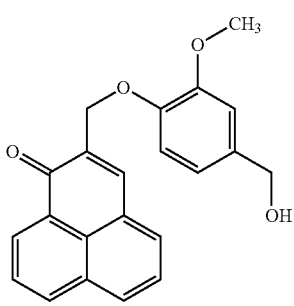

(104)
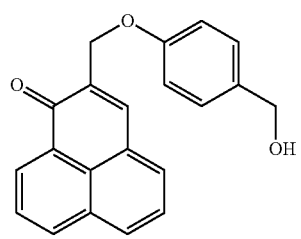
(105)
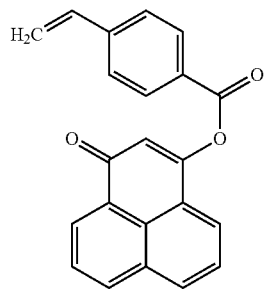
(106)
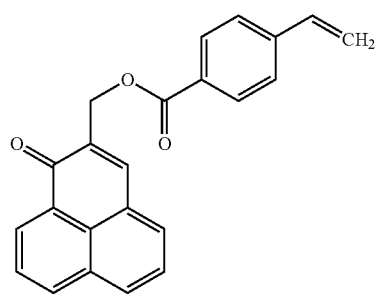
(107)
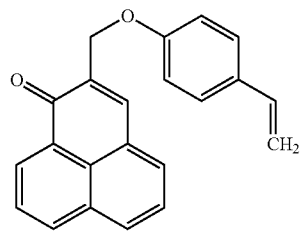
(108)
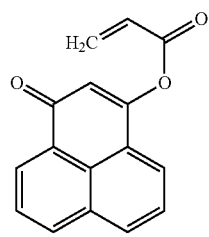
(109)
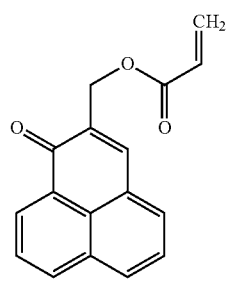
(110)
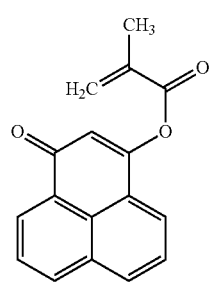
(111)
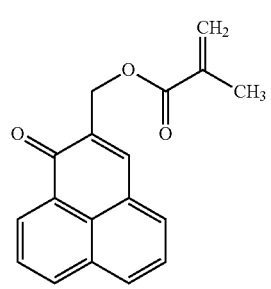
(112)
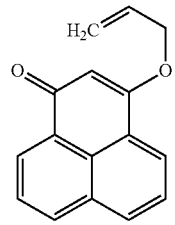
(113)
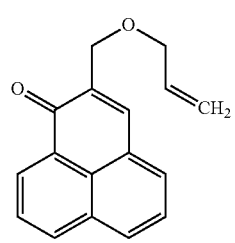
(114)
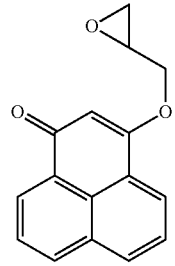
(115)
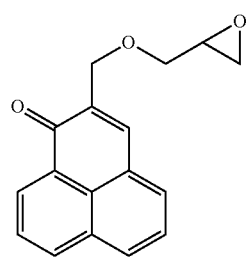
(116)

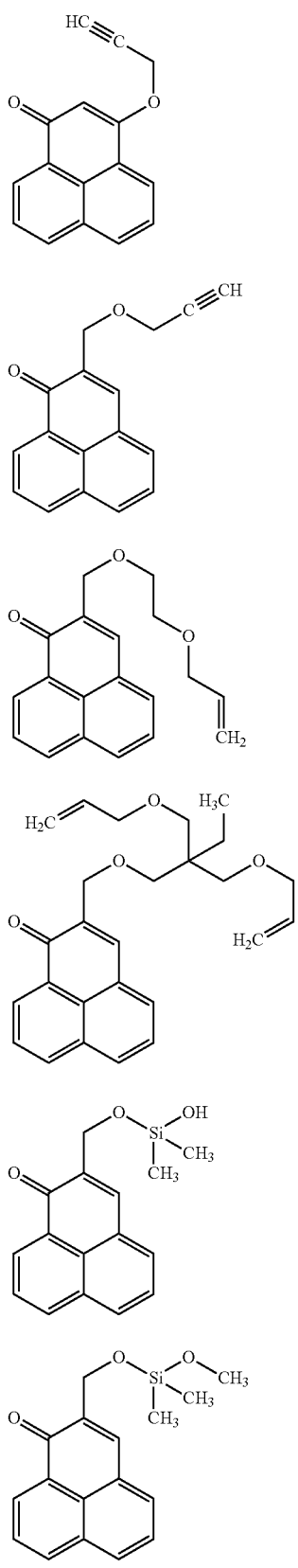
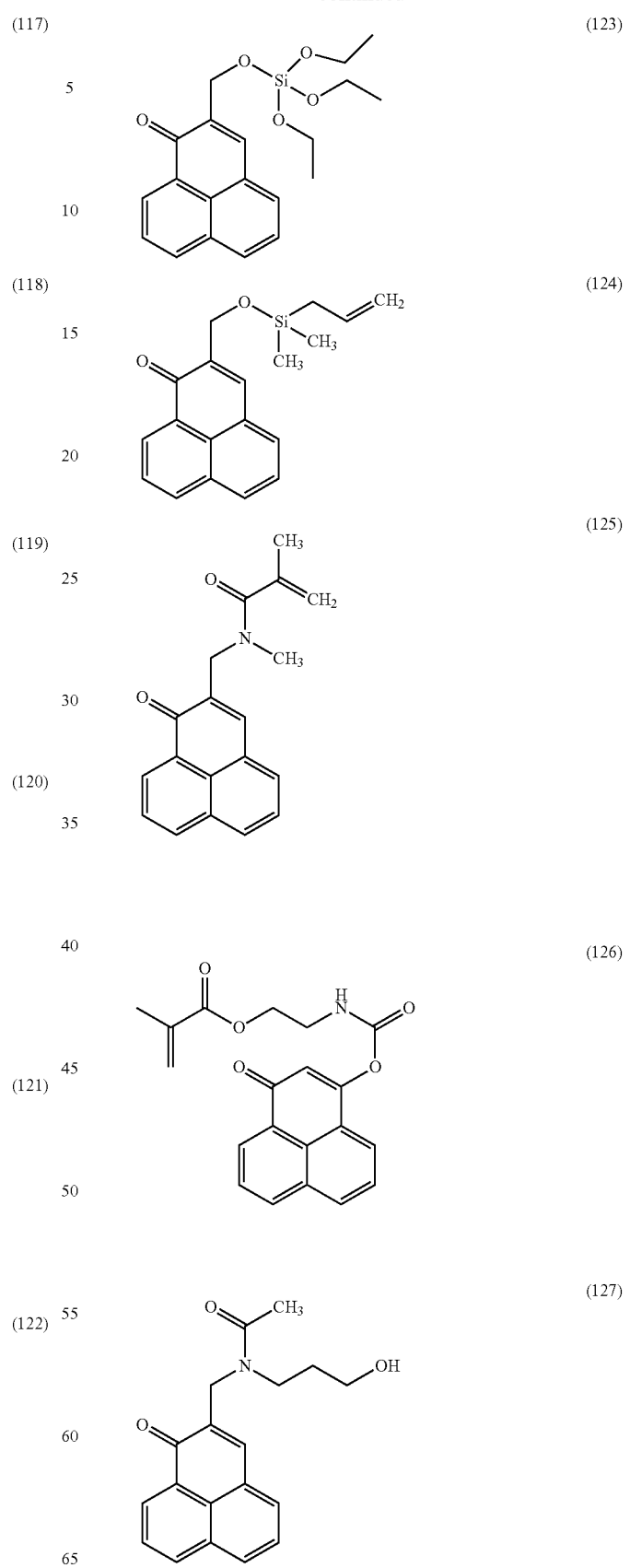

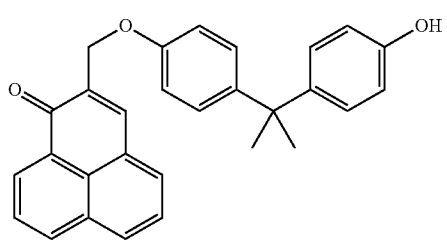
(162)

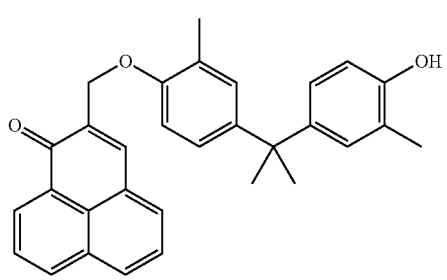
(163)

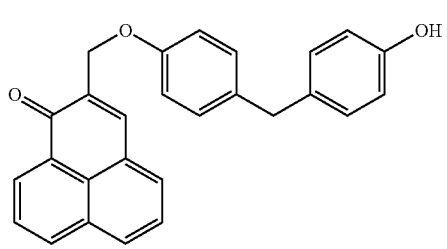
(164)

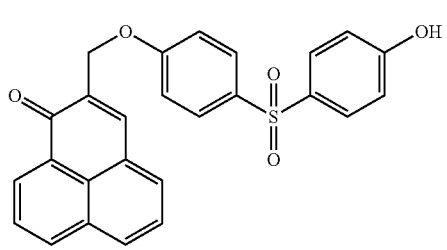
(165)

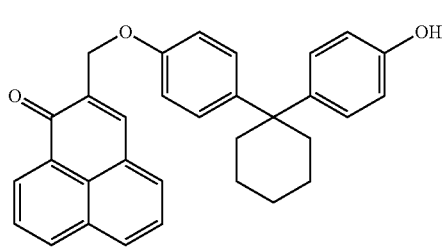
(166)

In a preferred embodiment, a phenalen-1-one compound with the general formula (1) is present as a salt, wherein Y⁻ is an anion which respectively independently of each other represents fluoride, chloride, bromide, iodide, sulphate, hydrogen sulphate, phosphate, hydrogen phosphate, dihydrogen phosphate, at least one carboxylate anion of a carboxylic acid containing 1 to 15 carbon atoms, at least one sulphonate anion of a sulphonic acid containing 1 to 12 C atoms or a mixture thereof.

An example of a suitable carboxylate anion of a carboxylic acid containing 1 to 15 carbon atoms is the acetate, oxalate, succinate, tartrate or a mixture thereof.

An example of a suitable sulphonate anion of a sulphonic acid containing 1 to 12 carbon atoms is the tosylate, mesylate or a mixture thereof.

In a preferred embodiment, a photosensitizer composition as disclosed herein comprises:

(a) at least one phenalen-1-one compound with the general formula (1) which is a phenalen-1-one compound as disclosed herein, and
(b) at least one polymeric component and/or precursor thereof.

In a preferred embodiment, a photosensitizer composition in accordance with the invention, preferably hardenable, is at least partially, preferably completely transparent to electromagnetic radiation which has a wavelength in the range from 280 to 1000 nm, more preferably from 320 to 900 nm, yet more preferably from 360 to 800 nm, yet more preferably from 380 to 700 nm, after hardening of the composition.

Preferably, by means of electromagnetic radiation which has a wavelength in the range from 280 to 1000 nm, more preferably from 320 to 900 nm, yet more preferably from 360 to 800 nm, yet more preferably from 380 to 700 nm, the at least one phenalen-1-one compound for use in accordance with the invention with the general formula (1) and/or a phenalen-1-one compound in accordance with the invention with the general formula (1a) contained in the composition is excited.

The excited at least one phenalen-1-one compound for use in accordance with the invention with the general formula (1), preferably with formula (1a), can cause the formation of reactive oxygen species (ROS), wherein on the one hand radicals, for example superoxide anions, hydrogen peroxide or hydroxyl radicals, and/or on the other hand excited molecular oxygen, for example singlet oxygen, may be formed.

Because after hardening, a photosensitizer composition in accordance with the invention is at least partially, preferably completely transparent to electromagnetic radiation which has the wavelength necessary to excite a phenalen-1-one compound with the general formula (1) for use in accordance with the invention and/or a phenalen-1-one compound in accordance with the invention with the general formula (1a), the incident electromagnetic radiation is only partially, and preferably not attenuated, as this would lead to a significant reduction in the singlet oxygen quantum yield.

A singlet oxygen quantum yield which is as high as possible is necessary for an antimicrobial activity during the photodynamic inactivation of microorganisms on surfaces.

More preferably, a photosensitizer composition in accordance with the invention is at least partially permeable to oxygen following hardening.

Preferably, following hardening, the photosensitizer composition in accordance with the invention is at least partially permeable both to molecular oxygen ($O_2$), which diffuses into the hardened photosensitizer composition, and also to singlet oxygen which is formed, preferably after irradiation of the at least one phenalen-1-one compound with the general formula (1), more preferably at least one phenalen-1-one compound with the general formula (1a), with electromagnetic radiation of a suitable wavelength and energy density.

The inventors have observed that by using at least one phenalen-1-one compound with the general formula (1), more preferably at least one phenalen-1-one compound with the general formula (1a), in a photosensitizer composition in accordance with the invention, following hardening of the photosensitizer composition, if is possible to provide a surface which, following irradiation with electromagnetic radiation of a suitable wavelength and energy density, preferably in the presence of oxygen and/or an oxygen-releasing compound, to reliably inactivate microorganisms adhering to the surface.

The inventors have furthermore observed that when using at least one phenalen-1-one compound with the general formula (1), preferably at least one phenalen-1-one compound with the general formula (1a), in a photosensitizer composition in accordance with the invention, following hardening of the photosensitizer composition, it is possible to provide a surface which, even upon longer irradiation with electromagnetic radiation of a suitable wavelength and energy density, exhibits essentially no, preferably no diminution in the photodynamic activity of the surface and microorganisms adhering to the surface are reliably inactivated.

A photosensitizer solution in accordance with the invention comprises at least one polymeric component and/or precursor thereof, wherein the at least one polymeric component and/or precursor thereof is selected from the group which consists of polymers and/or copolymers of acrylic acid and esters thereof, methacrylic acid and esters thereof, cyanoacrylic acid and esters thereof, acrylamide, methacrylamide, styrene, siloxanes and esters thereof, melamine, acrylonitrile, 1,3-butadiene, epichlorohydrin, polyols, polyisoprenes, polyethers, polyetherimides, polyvinyl acetates, polycarbonates, polyether sulphones, carboxymethyl cellulose, alginate, and combinations thereof.

Preferably, said at least one polymeric component and/or precursor thereof is a prepolymer and/or monomer, more preferably a resin. Preferably, said at least one polymeric component and/or precursor thereof is a polyurethane resin, an epoxy resin, a silicone or silicone resin, a polyacrylic resin, polymethacrylic resin, a melamine-formaldehyde resin, phenol-formaldehyde resin, an ABS (acrylonitrile, 1,3-butadiene, styrene) resin, an alkyd resin, a polyester resin, an alkyd resin, a polyamide resin, a fluoro rubber resin, a vinyl ester resin or a combination thereof. Preferably, said at least one polymeric component and/or precursor thereof may be present as a 1-component (1C) resin or as a 2-component (2C) resin.

More preferably, a photosensitizer composition in accordance with the invention comprises at least one polymeric component and/or precursor thereof and at least one phenalen-1-one compound with the general formula (1), preferably at least one phenalen-1-one compound with the general formula (1a), wherein preferably, the residue X of the at least one phenalen-1-one compound with the general formula (1), preferably at least one phenalen-1-one compound with the general formula (1a), can be coordinated with the at least one polymeric component and/or precursor thereof.

Examples of preferred combinations of at least one polymeric component and/or precursor thereof and at least one residue X of the at least one phenalen-1-one compound with the general formula (1) are as follows:
at least one polymeric component
and/or precursor thereof: residue X:
polyurethane resin —OH, —N($R^{(VI)}$)($R^{(VII)}$),
epoxy resin —OH, —N($R^{(VI)}$)($R^{(VII)}$), a residue with the general formula (20), (22) or (24),
silicone resin —Si($R^{(VIII)}$)($R^{(IX)}$)—[O—Si($R^{(X)}$)($R^{(XI)}$)]$_p$—Z, a residue with the general formula (20) or (22),
polyacrylic resin a residue with the general formula (20) to (23),
polymethacrylic resin a residue with the general formula (20) to (23),
polyacrylamide resin a residue with the general formula (20) to (23),
melamine-formaldehyde resin —OH, —N($R^{(VI)}$)($R^{(VII)}$), a residue
with the general formula (20) or (22),
phenol-formaldehyde resin —OH, —N($R^{(VI)}$)($R^{(VII)}$), a residue
with the general formula (20) or (22),
ABS (acrylonitrile, 1,3-butadiene, styrene) resin —OH, —N($R^{(VI)}$)($R^{(VII)}$), a residue
with the general formula (20) to (23),
alkyd resin —OH, —N($R^{(VI)}$)($R^{(VII)}$), a residue
with the general formula (20) to (23),
polyester resin —OH, —N($R^{(VI)}$)($R^{(VII)}$), a residue
with the general formula (20) to (23)
polyamide resin —OH, —N($R^{(VI)}$)($R^{(VII)}$), a residue
with the general formula (20) to (23),
fluoro rubber resin —OH, —N($R^{(VI)}$)($R^{(VII)}$), a residue
with the general formula (20) or (22),
vinyl ester resin a residue with the general formula (20) to (23).

Examples of preferred combinations of at least one polymeric component and/or precursor thereof and at least one residue $X^a$ of the at least one phenalen-1-one compound with the general formula (1a) are as follows:
at least one polymeric component
and/or precursor thereof: residue $X^a$:
polyurethane resin —OH,
epoxy resin —OH, a residue with the general formula (20), (22) or (24),
silicone resin —Si($R^{(VIII)}$)($R^{(IX)}$)—[O—Si($R^{(X)}$)($R^{(XI)}$)]$_p$—Z, a residue
with the general formula (20) or (22),
polyacrylic resin a residue with the general formula (20) to (23),
polymethacrylic resin a residue with the general formula (20) to (23),
polyacrylamide resin a residue with the general formula (20) to (23),
melamine-formaldehyde resin —OH, a residue with the general
formula (20) or (22),
phenol-formaldehyde resin —OH, a residue with the general
formula (20) or (22),
ABS (acrylonitrile, 1,3-butadiene, styrene) resin —OH, a residue with the general
formula (20) to (23),
polyester resin —OH, a residue with the general formula (20) to (23),
alkyd resin —OH, —N($R^{(VI)}$)($R^{(VII)}$), a residue
with the general formula (20) to (23)
polyamide resin —OH, a residue with the general formula (20) to (23),
fluoro rubber resin —OH, a residue with the general formula (20) or (22),
vinyl ester resin a residue with the general formula (20) to (23).

Following hardening of the photosensitizer composition, it is possible to provide an inventive photosensitizer composition with a surface which, even after lengthy irradiation with electromagnetic radiation of a suitable wavelength and energy density, exhibits essentially no and preferably no diminution in the photodynamic activity of the surface, and microorganisms which adhere to the surface are reliably inactivated.

An inventive composition comprises at least one cross-linking agent, for example at least one polyisocyanate, a blocked isocyanate, at least one alkyl diisocyanate or cycloalkyl diisocyanate or aryl diisocyanate, at least one compound with the general formula $SiZ_4$, $(R^{XII})SiZ_3$, $(R^{XII})_2SiZ_2$, a compound containing at least two epoxy residues, a compound containing at least two acrylamide residues, a compound containing at least two acrylate residues, a compound containing at least two aldehyde residues, a compound containing at least two alcohol groups, a compound containing at least two amine residues, a divinylsulphone, and combinations thereof, wherein the residue $R^{XII}$ respectively independently of each other represents alkyl which may be linear or branched, containing 1 to 5 carbon atoms, phenyl or benzyl, preferably methyl, ethyl, n-propyl, isopropyl, phenyl or benzyl, and wherein the residue Z respectively independently of each other represents halogen, hydroxyl, alkoxyl containing 1 to 4 carbon atoms or alkylcarboxyl containing 1 to 4 carbon atoms, preferably halogen or hydroxyl.

Examples of suitable compounds containing at least two alcohol groups are bisphenols, for example the commercially available bisphenols bisphenol A, bisphenol AF, bisphenol AP, bisphenol B, bisphenol BP, bisphenol C, bisphenol E, bisphenol F, bisphenol FL, bisphenol G, bisphenol M, bisphenol P, bisphenol PH, bisphenol S, bisphenol TMC, bisphenol Z and mixtures thereof, preferably bisphenol A (CAS 80-05-7), bisphenol C (CAS 79-97-0), bisphenol F (CAS 620-92-8), bisphenol S (CAS 80-09-1), bisphenol Z (CAS 843-55-0) and mixtures thereof.

More preferably, a photosensitizer composition in accordance with the invention comprises the at least one phenalen-1-one compound with the general formula (1), preferably with formula 1 a), which is covalently and/or electrostatically bonded, preferably covalently, to the at least one polymeric component and/or precursor thereof.

Preferably, a photosensitizer composition in accordance with the invention is a paint, a varnish, an emulsion paint, a latex paint, a silicate paint, or a chalk paint.

More preferably, a photosensitizer composition in accordance with the invention is a granulate.

More preferably, a photosensitizer composition in accordance with the invention is in the form of a coating, a self-supporting film, a fabric or a shaped article.

An article in accordance with the invention comprises at least one hardened polymer composition, wherein the hardened polymer composition comprises (a) at least one said phenalen-1-one compound with the general formula (1), at least one phenalen-1-one compound as disclosed herein, or a combination thereof, more preferably at least one said phenalen-1-one compound with the general formula (1a), and (b) at least one said hardened polymeric component, wherein the at least one phenalen-1-one compound with the general formula (1), the at least one phenalen-1-one compound as disclosed herein, or a combination thereof, more preferably the at least one said phenalen-1-one compound with the general formula (1a), is covalently and/or electrostatically bonded, preferably covalently, to the at least one hardened polymeric component.

Preferably, an article in accordance with the invention is obtained by coating, for example by spraying, varnishing, painting and/or dipping the article with a photosensitizer composition in accordance with the invention which is preferably spreadable, sprayable or flowable at the temperature of application, preferably liquid, and subsequent drying and/or hardening.

As an example, an article in accordance with the invention may be obtained by laminating, covering, gluing with a photosensitizer composition in accordance with the invention which is in the form of a fabric or a self-supporting film.

As an example, an article in accordance with the invention may be obtained by spraying, melt blowing, extrusion or other known processes for shaping a photosensitizer composition in accordance with the invention, which is preferably spreadable, sprayable or flowable at the temperature of manufacture, preferably liquid, and subsequent drying and/or hardening.

More preferably, an article in accordance with the invention comprises or consists of a hardened polymer composition which comprises (a) at least one phenalen-1-one compound as disclosed herein, and (b) at least one hardened polymeric component which is more preferably in the form of a coating, a self-supporting film, a fabric or a shaped article, wherein the at least one phenalen-1-one compound as disclosed herein is covalently and/or electrostatically bonded, preferably covalently, to the at least one hardened polymeric component.

The objective of the present invention is furthermore achieved by means of the use of a photosensitizer composition as disclosed herein and/or of a phenalen-1-one compound as disclosed herein and/or of an article as disclosed herein, for the inactivation, preferably for the photodynamic inactivation of microorganisms which are preferably selected from the group which consists of viruses, archaea, bacteria, bacterial spores, fungi, fungal spores, protozoa, algae and blood-borne parasites, and/or a biofilm thereof.

Preferably, a photosensitizer composition in accordance with the invention or a phenalen-1-one compound in accordance with the invention is used for the photodynamic surface cleaning and/or surface coating of an article or area.

Preferably, a photosensitizer composition in accordance with the invention or a phenalen-1-one compound in accordance with the invention is used for the surface coating of articles, preferably medical products, food packaging, textiles, building materials, electronic devices, furniture or hygiene articles.

Examples of other applications are Pacifiers, Teats, tubes and conduits, window panes, glass surfaces and/or tiles in wet rooms and/or wash rooms, touch screen elements, personal computers (PC) and peripheral devices, cloths, wipes, work surfaces, treatment and preparation surfaces in clinics and old people's homes, sanitary equipment, sanitary appliances, sausage skins, beverage containers, crockery or waste containers.

A method in accordance with the invention for the inactivation, preferably for the photodynamic inactivation, of microorganisms which preferably comprise viruses, archaea, bacteria, bacterial spores, fungi, fungal spores, protozoa, algae, blood-borne parasites or combinations thereof, and/or of a biofilm thereof, comprises the following steps:

(A) bringing the microorganisms and/or a biofilm thereof into contact with at least one coating which has been produced by hardening a photosensitizer composition as claimed and/or which contains at least one phenalen-1-one compound as claimed, and/or at least one article as claimed, and (B) irradiating the microorganisms and/or a biofilm thereof and the at least one phenalen-1-one compound contained in the coating and/or the article with electromagnetic radiation of a suitable wavelength and energy density.

As an example, transparent, clear or translucent articles such as, for example, teats, pacifiers, tubes, or the like, may be produced using a photosensitizer composition in accordance with the invention, and cleaned and/or decontaminated with the aid of the method in accordance with the invention.

More preferably, articles are treated which have a thermally limited durability, for example articles formed from thermoplastic synthetic materials, or which are attacked by disinfectants.

Articles which have a thermally limited durability may, for example, be insufficiently sterilized, because at higher temperatures they lose their shape or become brittle.

Furthermore, in the case of incorrect and/or excessive use of disinfectants, the build-up of resistance may occur by selecting more robust microorganisms if, for example, the concentration of the substance and the exposure time, and therefore the pathogen-reducing action, is too low.

In a preferred embodiment, the aforementioned alkyl residues containing 1 to 12 carbon atoms, more preferably 2 to 9 C atoms, are respectively independently of each other selected from the group which consists of methyl, ethyl, prop-1-yl, prop-2-yl, but-1-yl, but-2-yl, 2-methylprop-1-yl, 2-methyl prop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl and 2,3-dimethylbut-2-yl, n-pentyl, n-hexyl, n-heptyl and n-octyl and combinations thereof, more preferably from methyl, ethyl, n-propyl, n-butyl, n-pentyl, n-hexyl, n-heptyl and n-octyl and combinations thereof.

In a preferred embodiment, the aforementioned *—O-alkyl residues containing 1 to 12 C atoms, preferably 2 to 9 C atoms, are respectively independently of each other selected from the group which consists of methoxy, ethoxy, n-propoxy, iso-propoxy, n-butoxy, tert-butoxy and combinations thereof.

In a preferred embodiment, the aforementioned aryl residues containing 5 to 20 C atoms, more preferably 6 to 9 C atoms, are respectively independently of each other selected from the group which consists of phenyl, naphthyl, anthracenyl, phenanthrenyl and pyrenyl.

In a preferred embodiment, the aforementioned *—O-aryl residues containing 5 to 20 C atoms, more preferably 6 to 9 C atoms, are respectively independently of each other selected from the group which consists of *—O-phenyl, *—O-naphthyl, *—O-anthracenyl, and combinations thereof.

In a preferred embodiment, the aforementioned alkylaryl residues containing 5 to 20 C atoms, more preferably 6 to 9 C atoms, are respectively independently of each other selected from the group which consists of benzyl, 2-phenyl-eth-1-yl, 3-phenyl-eth-1-yl, and combinations thereof.

In a preferred embodiment, the aforementioned *—O-alkylaryl residues containing 5 to 20 C atoms, more preferably 6 to 9 C atoms, are respectively independently of each other selected from the group which consists of 1-methoxyphenyl, 1-ethoxy-2-phenyl, 1-propoxy-3-phenyl and combinations thereof.

In a further preferred embodiment, the aforementioned ether residues respectively independently of each other contain 2 to 12 C atoms, more preferably 3 to 9 C atoms, more preferably 4 to 7 C atoms. In a further preferred embodiment, the aforementioned ether residues respectively independently of each other are selected from the group which consists of methoxymethyl, methoxyethyl, methoxy-n-propyl, ethoxymethyl, n-propoxymethyl, 2-ethoxy-ethoxymethyl, 2-(2-ethoxyethoxy)ethyl, i-propoxymethyl, tert-butyloxymethyl, dioxa-3,6-heptyl and benzyloxymethyl. In a further preferred embodiment, the aforementioned ether residues may be simple ether residues, oligoether residues, polyether residues or mixtures thereof.

The invention will now be explained by means of figures and examples without being limited in any way thereto.

DESCRIPTION OF PREFERRED EMBODIMENTS

Figure 1A:
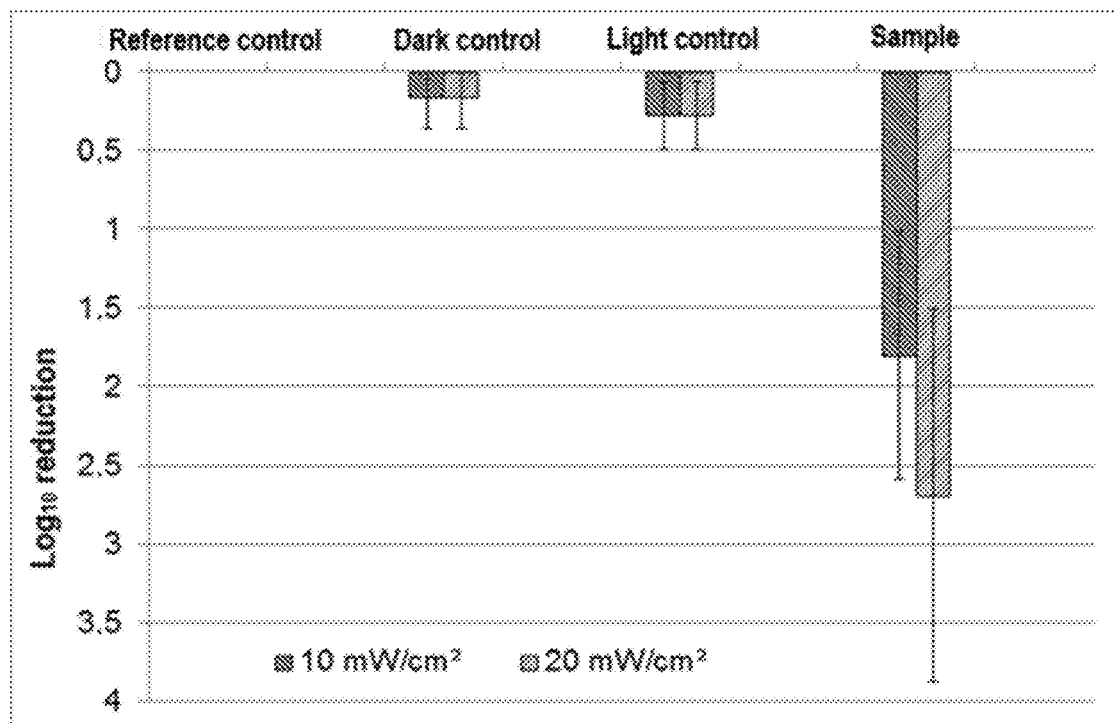
FIG. 1A shows the results of the log reduction of the *S. aureus* count in Example 3.1.

All of the chemicals used were purchased from established suppliers (Thermo Fisher Scientific, Polysciences Europe GmbH, Sigma Aldrich, TCI, ABCR, Acros, Merck and Fluka) and used without further purification. Solvents were distilled prior to use and, if necessary, were dried in the usual manner. Dry DMF was purchased from Fluka (Taufkirchen, DE).

Thin layer chromatography was carried out on thin layer aluminium foil coated with 60 F254 silica gel from Merck (Darmstadt, DE). Preparative thin layer chromatography was carried out on commercially available glass plates coated with silica gel 60 (20 cm×20 cm, Carl Roth GmbH & Co. KG, Karlsruhe, D E)). The compounds were detected using UV light ($\lambda$=254 nm, 333 nm) and sometimes detected with the naked eye or stained with ninhydrin. Chromatography was carried out using silica gel (0.060-0.200) from Acros (Waltham, US).

NMR spectra were measured on a Bruker Avance 300 spectrometer (300 MHz [1H-NMR]) (Bruker Corporation, Billerica, US).

All of the chemical displacements are given in $\delta$ [ppm] relative to an external standard (tetramethylsilane, TMS). The coupling constants are respectively given in Hz; characterization of signals: s=singlet, d=doublet, t=triplet, m=multiplet, dd=doublet of doublets, br=broad. Integration determined the relative number of atoms. The unequivocal determination of the signals in the carbon spectrum was carried out using the DEPT method (pulse angle: 135°). Error limits: 0.01 ppm for $^1$H-NMR and 0.1 Hz for coupling constants. The solvent used is recorded for each spectrum.

The IR spectra were recorded on a Biorad Excalibur FTS 3000 spectrometer (Bio-Rad Laboratories GmbH, Munich, DE).

ES-MS spectra were measured using a ThermoQuest Finnigan TSQ 7000 spectrometer, all HR-MS spectra were determined on a ThermoQuest Finnigan MAT 95 spectrometer (each from Thermo Fisher Scientific Inc, Waltham, US), and argon was used as the ionization gas for FAB.

The melting points were determined with the aid of the Büchi SMP-20 melting point measuring instrument (Büchi Labortechnik GmbH, Essen, DE) using a glass capillary.

All of the UV/vis spectra were recorded using a Varian Cary 50 bio UV/VIS spectrometer, and fluorescence spectra were recorded with a Varian Cary Eclipse spectrometer (both from Agilent Technologies, Santa Clara, US).

The solvents for the absorption and emission measurements were purchased from Acros or Baker or Uvasol from Merck in special spectroscopic grades. Millipore water (18 MΩ, Milli QPlus) was used for all measurements.

Example 1: Production of the Phenalen-1-One Derivatives

Overview 1: Synthesis of the Phenalen-1-One Derivatives Employed

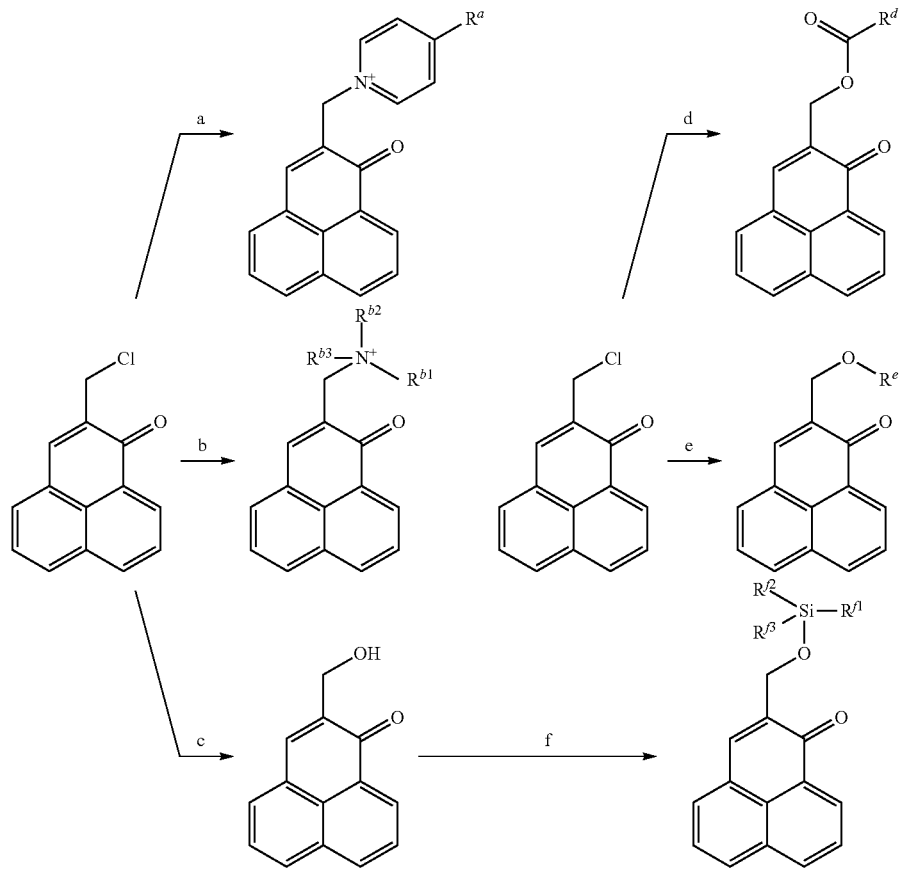

Conditions: a) Substituted pyridine, MeCN, 50° C., 6 h; b) Substituted dimethylamine, MeCN, RT, 24 h; c) 4N NaOH, water, toluene, tetrabutylammonium hydrogen sulphate, RT, 6 h; d) Variation 1: carboxylic acid as sodium salt, Adogen® 464, toluene, reflux, 4 h; Variation 2: carboxylic acid, DMAP, DCC, THF, 0° C.→RT, 4 h; e) Substituted alcohol, toluene, 4N NaOH, tetrabutylammonium hydrogen sulphate, RT, 6 h or substituted phenol, THF, PPh₃, DEAD, 0° C.→RT, 6 h; f) Substituted silyl chloride, DCM or THF, triethylamine or imidazole, 0° C.→RT;

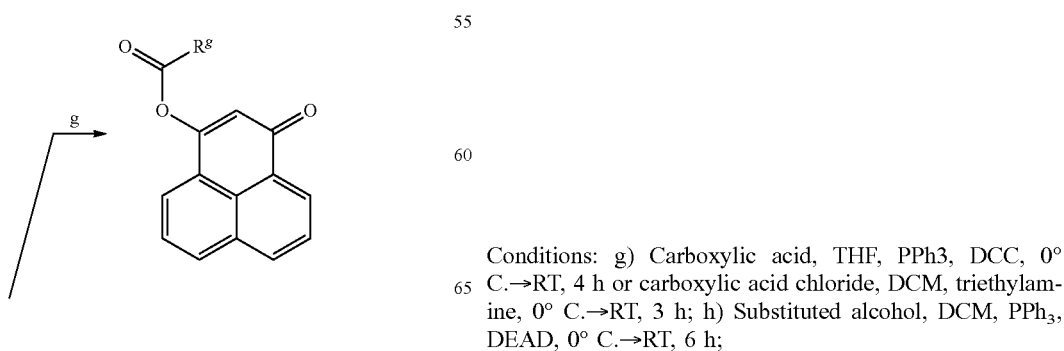

-continued

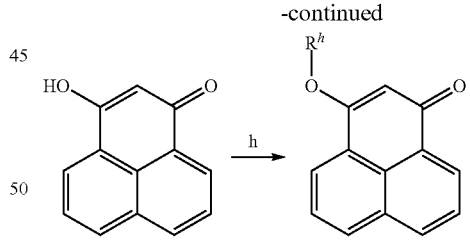

Conditions: g) Carboxylic acid, THF, PPh3, DCC, 0° C.→RT, 4 h or carboxylic acid chloride, DCM, triethylamine, 0° C.→RT, 3 h; h) Substituted alcohol, DCM, PPh₃, DEAD, 0° C.→RT, 6 h;

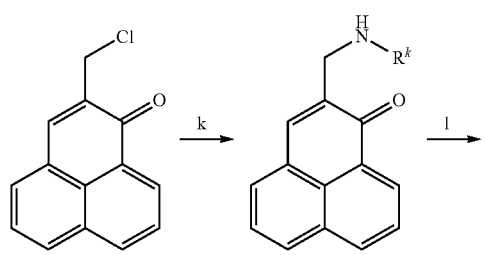

1. Production of 2-chloromethyl-1H-phenalen-1-one 2-chloromethyl-1H-phenalen-1-one was obtained using the method described in Example 1 of US 2014/039184 A1. The NMR spectrum corresponded to the values disclosed in US 2014/039184 A1.

2. General Specification a)

| | Substituted pyridine in overview 1, step a) | MW [g/mol] | Weight [mg] | | Product | |
|---|---|---|---|---|---|---|
| | | | | | Formula | Designation |
| 2.1 | 4-pyridine methanol (Sigma-Aldrich) $R^a$ = *—$CH_2OH$ | 109.13 | 270 | → | | SAPN-19a [compound (132)] |
| 2.2 | 4-pyridine ethanol (Sigma-Aldrich) $R^a$ = *—$CH_2CH_2OH$ | 123.16 | 310 | → | | SAPN-19b [compound (134)] |

-continued

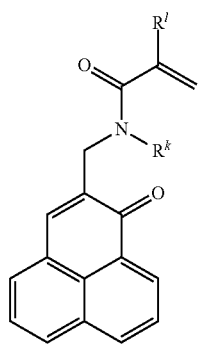

Conditions: k) Secondary amine in methanol, 0° C.→RT, 6 h;

l) Carboxylic acid chloride, DCM or THF, triethylamine, 0° C.→RT;

2-chloromethyl-1H-phenalen-1-one (115 mg, 0.5 mmol) was placed in acetonitrile (6 mL). The substituted pyridine given above (2.5 mmol) was respectively added slowly in small portions. The suspension was stirred for 3 days at room temperature in the dark.

For purification, the suspension was divided into two polypropylene tubes with conical bases (nominal volume 15 mL, Greiner Bio-One GmbH, Frickenhausen, D E) and precipitated by adding diethyl ether up to 15 mL per tube. The product was centrifuged (60 mins, 4400 rpm, 0° C.) and the supernatant was discarded. The precipitate was suspended in diethyl ether. After the product had settled out, in each case, the supernatant was discarded. The purification step was repeated once more and the product was then dried.

3. General Specification b)

| | Substituted dimethylamine in overview 1, step b) | MW [g/mol] | Weight [mg] | Product Formula | Designation |
|---|---|---|---|---|---|
| 3.1 | N,N-dimethylallylamine (Sigma-Aldrich) $R^{b1}$ = 2-propen-1-yl $R^{b2}, R^{b3}$ = methyl | 85.16 | 170 | → | SAPN-35a [compound (135)] |
| 3.2 | 1-N,N-dimethylamino-2-propyne (Sigma-Aldrich) $R^{b1}$ = 2-propyn-1-yl $R^{b2}, R^{b3}$ = methyl | 83.13 | 166 | → | SAPN-35a [compound (136)] |
| 3.3 | N-(4-vinylbenzyl)-N,N-dimethylamine (Thermo Fisher Scientific) $R^{b1}$ = 4-vinylphen-1-yl $R^{b2}, R^{b3}$ = methyl | 161.24 | 322 | → | SAPN-36 [compound (137)] |
| 3.4 | 2-(N,N-dimethylamino)-ethyl methacrylate (Sigma-Aldrich) $R^{b1}$ = eth-1-ylmethacrylate $R^{b2}, R^{b3}$ = methyl | 157.21 | 314 | → | SAPN-37a [compound (138)] |

-continued

| | Substituted dimethylamine in overview 1, step b) | MW [g/mol] | Weight [mg] | Product Formula | Product Designation |
|---|---|---|---|---|---|
| 3.5 | N-[2-(N,N-dimethylamino)-ethyl]-methacrylamide (Polysciences Europe GmbH) $R^{b1}$ = eth-1-ylmethacrylamide $R^{b2}$, $R^{b3}$ = methyl | 156.22 | 312 | → 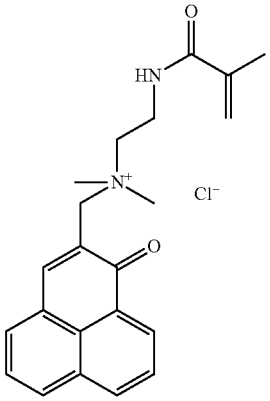 [SMILES: C=C(C)C(=O)NCC[N+](C)(C)CC1=Cc2cccc3cccc(c23)C1=O ; [Cl-]] | SAPN-37b [compound (139)] |
| 3.6 | (N,N-dimethyl-3-aminopropyl)-trimethoxysilane (Sigma-Aldrich) $R^{b1}$ = 3-(trimethoxysilyl)-prop-1-yl $R^{b2}$, $R^{b3}$ = methyl | 207.34 | 414 | → 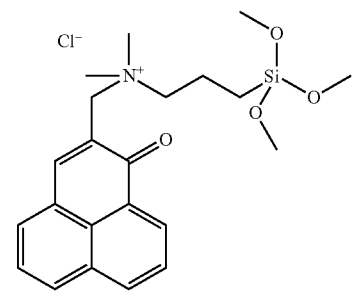 [SMILES: CO[Si](CCC[N+](C)(C)CC1=Cc2cccc3cccc(c23)C1=O)(OC)OC ; [Cl-]] | SA-PN-38 [compound (140)] |
| 3.7I | 1-N-Boc-ethylene diamine (Sigma-Aldrich) $R^{b1}$ = 2-N-Boc-ethyleneamin-1-yl $R^{b2}$, $R^{b3}$ = H | 160.2 | 320 | → 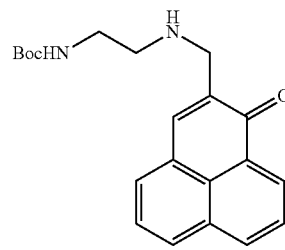 | SA-PN-25c-boc |
| 3.8 | 2-N-Boc-aminoethyl-1-N,N-dimethylamine $R^{b1}$ = 2-N-Boc-ethyleneamin-1-yl $R^{b2}$, $R^{b3}$ = methyl | 198.2 | 396 | → 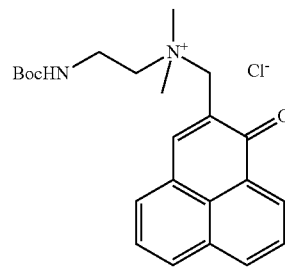 | SA-PN-25a-boc |

| | Substituted dimethylamine in overview 1, step b) | MW [g/mol] | Weight [mg] | | Product Formula | Designation |
|---|---|---|---|---|---|---|
| 3.9 | 1,1-N,N-(2-N-Boc-aminoethyl)-N-methylamine<br>$R^{b1}$, $R^{b2}$ = 2-N-Boc-ethyleneamin-1-yl<br>$R^{b3}$ = methyl | 327.2 | 654 | → | 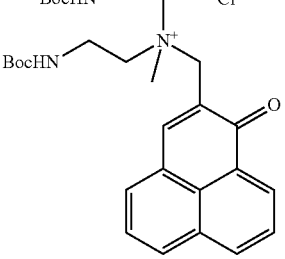 | SA-PN-34a-boc |
| 3.10 | 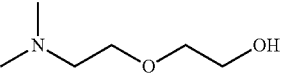<br>$R^{b1}$ = *—$(CH_2)_2O(CH_2)_2OH$<br>$R^{b2}$, $R^{b3}$ = $CH_3$ | 133.19 | 400 | → | 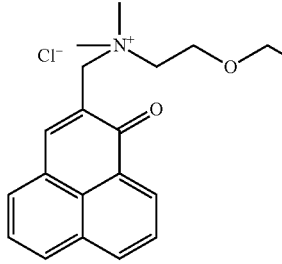 | SA-PN-11 [compound (142)] |
| 3.11 | 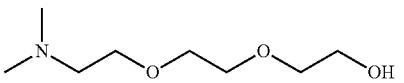<br>$R^{b1}$ = *—$(CH_2)_2O[(CH_2)_2O]_2H$<br>$R^{b2}$, $R^{b3}$ = $CH_3$ | 177.25 | 530 | → | 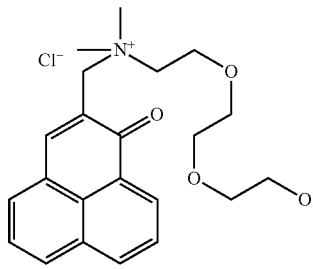 | SA-PN-12 [compound (143)] |
| 3.12 | N,N-dimethyl-aminoethanol<br>$R^{b1}$ = *—$(CH_2)_2OH$<br>$R^{b2}$, $R^{b3}$ = $CH_3$ | 89.14 | 270 | → | 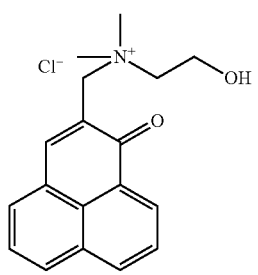 [SMILES: C[N+](C)(CCO)CC1=Cc2cccc3cccc(c23)C1=O ; [Cl-]] | SA-PN-09 [compound (141)] |

2-chloromethyl-1H-phenalen-1-one (115 mg, 0.5 mmol) was placed in acetonitrile (6 mL). The substituted dimethylamine given above (2 mmol) was respectively added slowly in small portions. The suspension was stirred for 48 h at room temperature in the dark.

For purification, the suspension was divided into two polypropylene tubes with conical bases (nominal volume 15 mL, Greiner Bio-One GmbH) and precipitated by adding diethyl ether up to 15 mL per tube. The product was centrifuged (60 mins, 4400 rpm, 0° C.) and the supernatant was discarded. The precipitated was suspended in diethyl ether. After the product had settled out, in each case, the supernatant was discarded. The purification step was repeated once more and the product was then dried.

4. Specification c): Production of 2-hydroxymethyl-1H-phenalen-1-one

[Designation: PNOH, compound (100)]

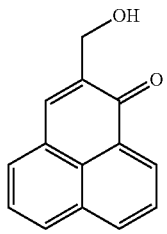

2-chloromethyl-1H-phenalen-1-one (230 mg, 1 mmol) was dissolved in 20 mL of toluene. Aqueous sodium hydroxide (4N, 5 mL) and the phase transfer catalyst tetrabutylammonium hydrogen sulphate (100 mg) were added. The reaction mixture was stirred vigorously for 6 h at room temperature. A yellow-brown precipitate was formed. The precipitate was filtered off and washed with water (4 times, 20 mL), toluene and petroleum ether (respectively 1 time, 20 mL). The product was dried in air to constant weight.

5. General Specification d)

|   |   | Carboxylic acid in overview 1, step d) | | | Product | |
|---|---|---|---|---|---|---|
|   |   | MW [g/mol] | Weight [mg] |   | Formula | Designation |
| 5.1 | acrylic acid (Sigma-Aldrich) $R^d = *{-}CH{=}CH_2$ | 72.06 | 72 | → | (structure) | PN-AMO-07a [compound (110)] |
| 5.2 | methacrylic acid (Sigma-Aldrich) $R^d = *{-}C(CH_3){=}CH_2$ | 87.09 | 87 | → | (structure) | PN-AMO-07b [compound (112)] |
| 5.3 | 4-vinylbenzoic acid (Sigma-Aldrich) $R^d$ = 4-vinylphen-1-yl | 148.16 | 148 | → | (structure) | PN-AMO-08 [compound (107)] |

Variation 1

The carboxylic acids given above (1 mmol) were respectively neutralized with an equimolar quantity of sodium hydroxide and the sodium salt of the carboxylic acid obtained was isolated by freeze drying.

2-chloromethyl-1H-phenalen-1-one (115 mg, 0.5 mmol) was dissolved in toluene (3 mL). The sodium salt of the carboxylic acid given above, hydroquinone (11 mg, 0.1 mmol) and Adogen® 464 (200 mg) were added and the reaction mixture was refluxed for 4 h with vigorous stirring. After cooling to room temperature, it was diluted with toluene (20 mL) and shaken with water (30 mL). The aqueous phase was extracted twice with acetic acid ethyl ester (20 mL). The organic phases were combined, washed with water (50 mL) separated and dried over magnesium sulphate.

After filtration and concentration under reduced pressure, the raw product was purified by flash chromatography (DCM/PE 2:1).

Variation 2

Compound (100) (65 mg, 0.3 mmol) was dissolved in dry THF (1 mL). The aforementioned carboxylic acid, hydroquinone (11 mg, 0.1 mmol), DMAP (61 mg, 0.5 mmol) and DCC (103 mg, 0.5 mmol) were added at 2-5° C. The reaction mixture was stirred vigorously for 4 h at RT. It was diluted with acetic acid ethyl ester (20 mL) and shaken with water (30 mL). The aqueous phase was extracted twice with acetic acid ethyl ester (20 mL). The organic phases were combined, washed with water (50 mL), separated and dried over magnesium sulphate.

After filtration and concentration under reduced pressure, the raw product was purified by flash chromatography (DCM/PE 2:1).

6. General Specification e)

| | Substituted alcohol in overview 1, step e) | MW [g/mol] | Weight [mg] | | Product Formula | Designation |
|---|---|---|---|---|---|---|
| 6.1 | allyl alcohol (Sigma-Aldrich) $R^e$ = 2-propen-1-yl | 58.08 | 58 | → | 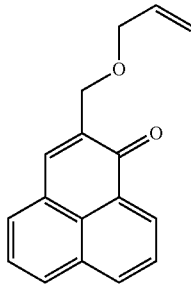 | PN-AMO-04a [compound (114)] |
| 6.2 | Propargyl alcohol (Sigma-Aldrich) $R^e$ = 2-propyn-1-yl | 56.06 | 56 | → | 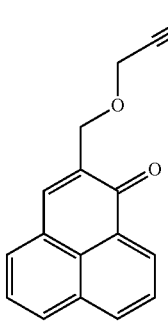 | PN-AMO-04b [compound (118)] |

-continued
| | Substituted alcohol in overview 1, step e) | | | Product | |
|---|---|---|---|---|---|
| | | MW [g/mol] | Weight [mg] | Formula | Designation |
| 6.3 | 4-vinyl phenol (Sigma-Aldrich) $R^e$ = 4-vinylphen-1-yl | 120.15 | 120 | → | PN-AMO-06 [compound (108)] |
| 6.4 | 2-allyloxyethanol (Sigma-Aldrich) $R^e$ = 2-allyloxyeth-1-yl | 102.13 | 102 | → | PN-AMO-05 [compound (119)] |
| 6.5 | Glycerine (Sigma-Aldrich) $R^e$ = 2,3-dihydroxyprop-1-yl | 92.09 | 92 | → | PN-AMO-10 [compound (103)] |
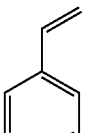

-continued

| | Substituted alcohol in overview 1, step e) | MW [g/mol] | Weight [mg] | Product Formula | Designation |
|---|---|---|---|---|---|
| 6.6 | 4-hydroxy-benzyl alcohol (Sigma-Aldrich) $R^e$ = 4-(hydroxymethyl)phen-1-yl | 124.14 | 124 | → (structure with OH-benzyl-O-CH₂-phenalenone) | PN-AMO-02b [compound (105)] |
| 6.7 | 4-hydroxy-3-methoxy-benzyl alcohol (Sigma-Aldrich) $R^e$ = 4-(hydroxymethyl)-2-methoxy-phen-1-yl | 154.17 | 154 | → (structure with OH-benzyl-methoxy-O-CH₂-phenalenone) | PN-AMO-04a [compound (104)] |

2-chloromethyl-1H-phenalen-1-one (115 mg, 0.5 mmol) was placed in toluene (4 mL). The aforementioned substituted alcohol (1 mmol), hydroquinone (11 mg, 0.1 mmol) and tetrabutylammonium hydrogen sulphate (100 mg) were added. 2 mL of aqueous 4N sodium hydroxide was added to the vigorously stirred solution at 2-5° C. The ice bath was removed and the reaction mixture was stirred vigorously for a further 6 h. It was diluted with 30 mL DCM and shaken several times with water (4 times, each time 20 mL).

The organic phase was separated out and dried over magnesium sulphate. After filtration and concentration under reduced pressure, the raw product was purified by flash chromatography (DCM/PE 2:1).

7. General Specification f)

| | Substituted silyl chloride in overview 1, step f) | MW [g/mol] | Weight [mg] | | Product Formula | Designation |
|---|---|---|---|---|---|---|
| 7.1 | Triethoxychlorosilane (Sigma-Aldrich) $R^{f1}, R^{f2}, R^{f3}$ = ethoxy | 198.72 | 76 | → | 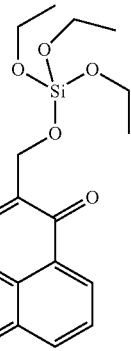 | PN-AMO-14a [compound (123)] |
| 7.2 | Allyldimethylchlorosilane (Sigma-Aldrich) $R^{f1}$ = 2-propen-1-yl $R^{f2}, R^{f3}$ = methyl | 134.68 | 54 | → | 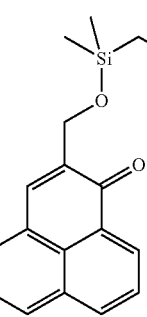 | PN-AMO-14b [compound (124)] |

2-hydroxymethyl-1H-phenalen-1-one (70 mg, 0.3 mmol) was placed together with imidazole (30 mg, 0.4 mmol) in dry DCM (3 mL) in a 10 mL round bottomed flask with a septum, under nitrogen. The aforementioned substituted silyl chloride (0.4 mmol) in 2 mL of dry DCM was slowly added dropwise through the septum using a syringe, at approximately 0° C. The ice bath was removed and the reaction mixture was stirred at room temperature overnight. It was diluted with 30 mL DCM and shaken several times with water (4 times, 20 mL each time). The organic phase was separated and dried over magnesium sulphate. After filtration and concentration under reduced pressure, the raw product was purified using flash chromatography (DCM/PE 2:1).

8. General Specification g)

| | Carboxylic acid in overview 1, step g) | MW [g/mol] | Weight [mg] | | Product Formula | Designation |
|---|---|---|---|---|---|---|
| 8.1 | acrylic acid $R^g$ = *—CH=CH$_2$ | 72.06 | 53 | → | 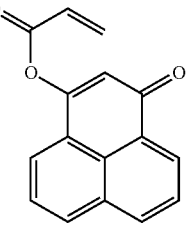 | PN-AMO-12a [compound (109)] |

-continued

| | Carboxylic acid in overview 1, step g) | MW [g/mol] | Weight [mg] | Product Formula | Product Designation |
|---|---|---|---|---|---|
| 8.2 | methacrylic acid $R^g = *-C(CH_3)=CH_2$ | 87.09 | 62 | → (structure) | PN-AMO-12b [compound (111)] |
| 8.3 | 4-vinylbenzoic acid $R^g$ = 4-vinylphen-1-yl | 148.16 | 88 | → (structure) | PN-AMO-12c [compound (106)] |

3-hydroxy-phenalen-1-on (Sigma-Aldrich) (100 mg, 0.5 mmol) was placed together with triphenylphosphine (50 mg, 1 mmol) and the aforementioned carboxylic acid (0.6 mmol) in dry THF (5 mL) in a 10 mL round bottomed flask with a septum, under nitrogen. DCC (103 mg, 0.5 mmol) in dry THF (1 mL) was slowly added dropwise through the septum using a syringe, at approximately 0° C. After stirring for 2 h in the ice bath, a further portion of DCC (103 mg, 0.5 mmol) in dry THF (1 mL) was added dropwise. The reaction mixture was stirred in the thawing ice bath, then at room temperature for 6 h. The THF was withdrawn, the residue was taken up in 30 mL of DCM and shaken several times with water (4 times, 20 mL).

The organic phase was separated and dried over magnesium sulphate. After filtration and concentration under reduced pressure, the raw product was purified using flash chromatography (DCM/PE 2:1).

9. General Specification h)

| | Substituted alcohol in overview 1, step h) | MW [g/mol] | Weight [mg] | Product Formula | Product Designation |
|---|---|---|---|---|---|
| 9.1 | allyl alcohol $R^h$ = 2-propen-1-yl | 58.08 | 23 | → (structure) | PN-AMO-11a [compound (113)] |

| | Substituted alcohol in overview 1, step h) | MW [g/mol] | Weight [mg] | | Product Formula | Designation |
|---|---|---|---|---|---|---|
| 9.2 | propargyl alcohol $R^h$ = 2-propyn-1-yl | 56.06 | 22 | → | (structure) | PN-AMO-11b [compound (117)] |
| 9.3 | glycidol (Sigma-Aldrich) $R^h$ = 2,3-epoxy-prop-1-yl | 74.08 | 30 | → | (structure) | PN-AMO-13 [compound (115)] |
| 9.4 | bis(2-hydroxyethyl)ether (Thermo Fisher Scientific) $R^h$ = *—(CH$_2$)$_2$O(CH$_2$)$_2$OH | 106.12 | 42 | → | (structure) | PN-AMO-03a [compound (102)] |
| 9.5 | 1,3-propanediol (Sigma-Aldrich) $R^h$ = *—(CH$_2$)$_2$OH | 76.10 | 31 | → | (structure) | PN-AMO-03b [compound (101)] |
| 9.6I | 3-Boc-aminopropan-1-ol (Sigma-Aldrich) $R^h$ = *—(CH$_2$)$_2$NHBoc | 175.2 | 70 | → | (structure) | SAPN-32-boc |

3-hydroxy-phenalen-1-on (60 mg, 0.3 mmol) was placed together with triphenylphosphine (30 mg, 0.6 mmol) in DCM (3 mL) and the aforementioned substituted alcohol (0.4 mmol) in a 10 mL round bottomed flask with a septum, under nitrogen. DEAD in toluene (40%, 0.2 mL, 0.4 mmol) was slowly added dropwise using a syringe via the septum, at approximately 0° C. The reaction mixture was stirred in the thawing ice bath, then at room temperature for 6 h. It was diluted with 30 mL of DCM and shaken several times with water (4 times, 20 mL). The organic phase was separated and dried over magnesium sulphate. After filtration and concentration under reduced pressure, the raw product was purified using flash chromatography (DCM/PE 2:1).

10. Specification k): Production of 2-(N-methylamino)methyl-1H-phenalen-1-one Hydrochloride

[Designation: SAPN-02c, Compound (158)]]

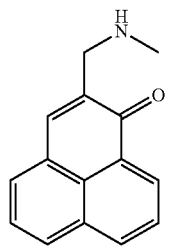

$R^k$ = methyl 2-chloromethyl-1H-phenalen-1-one (113 mg, 0.5 mmol) in methanol (10 mL) was added dropwise to an ice cold solution of the amine in methanol (10 mL, 5 M) over 2 h. After stirring vigorously for 1 h at room temperature, the solvent together with the surplus amine was driven off in the stream of nitrogen. The residue was dissolved in as little DCM/ethanol 4:1 as possible and precipitated by adding diethyl ether. The product was centrifuged (60 mins, 4400 rpm, 0° C.) and the supernatant was discarded. The precipitate was suspended in diethyl ether and centrifuged again. The purification step was repeated once more and the product was then dried.

2-(N-methylamino)methyl-1H-phenalen-1-one hydrochloride (80 mg, 0.3 mmol) was dissolved with triethylamine (100 mg, 1 mmol) in DCM (3 mL) and stirred in an ice bath with the exclusion of moisture. The corresponding carboxylic acid chloride (0.4 mmol) in DCM (0.5 mL) was added dropwise. The reaction mixture was stirred in the thawing ice bath, then at room temperature for 4 h. It was diluted with 30 mL of DCM and shaken several times with water (4 times, 20 mL). The organic phase was separated and dried over magnesium sulphate. After filtration and concentration under reduced pressure, the raw product was purified using flash chromatography.

12. Synthesis of Compound (127)

[Designation: PN-AMO-01]

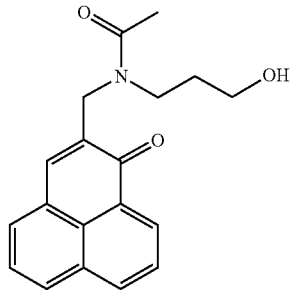 [SMILES: CC(=O)N(CCCO)CC1=Cc2cccc3cccc(c23)C1=O]

2-chlormethyl-1H-phenalen-1-one (230 mg, 1.0 mmol) in acetonitrile (20 mL) was added dropwise to a solution of 3-aminopropanol (1.5 mL, 20 mmol) in acetonitrile (50 mL)

11. General Specification l)

| | Carboxylic acid chloride in overview 1, step I) | MW [g/mol] | Weight [mg] | | Product Formula | Designation |
|---|---|---|---|---|---|---|
| 11.1 | acrylic acid chloride (Merck-Millipore) $R^k$ = methyl $R^l$ = 2-ethen-1-yl | 90.5 | 36 | → | | PN-AMO-07a [compound (126)] |
| 11.2 | Methacrylic acid chloride $R^k$ = methyl $R^l$ = 1-methyl-2-ethen-1-yl | 104.53 | 41 | → | | PN-AMO-07b [compound (126)] | over 30 min. After stirring overnight at room temperature, triethylamine (2.02 g, 2.66 mL, 20 mmol) was added and the solution was stirred in an ice bath. Acetic acid anhydride (3.06 g, 2.83 mL, 30 mmol) was added dropwise at approximately 0° C. The reaction mixture was stirred for 2 h at room temperature, then heated to 50° C. for 1 h. All of the volatile components were removed under reduced pressure.

The product was purified by column chromatography using dichloromethane/ethanol 20:1. 261 mg of a yellow syrup was obtained. This material was dissolved in methanol (2 mL). Aqueous sodium hydroxide (1 M, 0.5 mL) was added and the mixture was stirred overnight at room temperature. The alcohol was withdrawn and the remaining solution was diluted with water (10 mL). The product was extracted with dichloromethane (2×10 mL). The organic phases were dried over magnesium sulphate, filtered and concentrated under reduced pressure. The product was a yellowish, greasy solid (215 mg, 69%, 0.69 mmol).

13. Deprotection of the Boc Group

| | Protected phenalenone derivative | | Product | |
|---|---|---|---|---|
| | | | Formula | Designation |
| 13.1 | 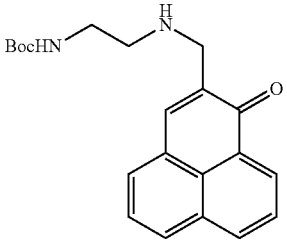 [SMILES: CC(C)(C)OC(=O)NCCNCC1=Cc2cccc3cccc(c23)C1=O]<br>(from synthesis 3.7) | → | 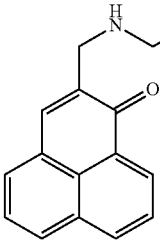 | SA-PN-25c<br>[compound (150)] |
| 13.2 | 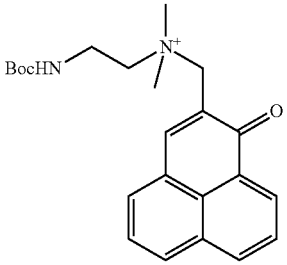 [SMILES: CC(C)(C)OC(=O)NCC[N+](C)(C)CC1=Cc2cccc3cccc(c23)C1=O]<br>(from synthesis 3.8) | → | 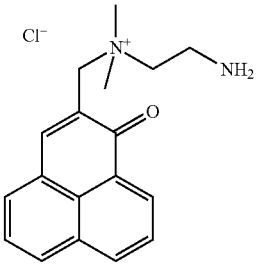 [SMILES: C[N+](C)(CCN)CC1=Cc2cccc3cccc(c23)C1=O ; [Cl-]] | SA-PN-25b<br>[compound (159)] |
| 13.3 | 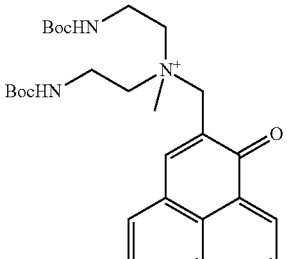<br>(from synthesis 3.9) | → | 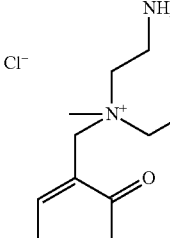 | SA-PN-34b<br>[compound (160)] |
| 13.4 | 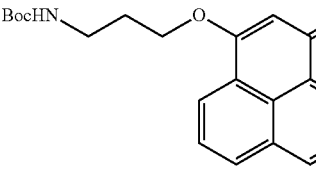<br>(from synthesis 9.6) | → | 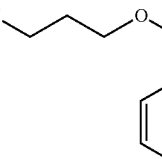 | SAPN-32<br>[compound (161)] |

The corresponding tert-butyloxycarbonyl (Boc-protected phenalenone derivative was placed in dichloromethane (3 mL per 100 mg). A saturated solution of hydrochloric acid in diethyl ether (0.5 mL per mmol Boc group) was added dropwise. The batch was stirred for 3 h with the exclusion of moisture. The product was precipitated by adding 30 mL of diethyl ether. The precipitate was centrifuged and washed thoroughly with diethyl ether. The product was dried under reduced pressure.

The respective calculated molecular weight (MW) and molecular formula (MF) as well as the data for the measured mass spectra (MS) and $^1$H NMR spectra are given below for the compounds produced.

| Sub-stance No. | | Structure | Molecular weight (MW)/Molecular formula (MF) | Mass spectrum (MS) | NMR |
|---|---|---|---|---|---|
| 2.1 | SAPN-19a | 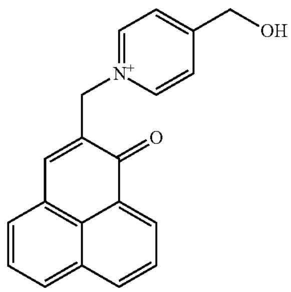 [SMILES: O=C1C(C[n+]2ccc(CO)cc2)=Cc2cccc3cccc1c23] | MW: 302.3 + 35.45 = 337.75 g/mol MF: $C_{20}H_{16}NO_2Cl$ | MS (ESI-MS, $CH_2Cl_2$/MeOH + 10 mmol $NH_4OAc$): m/z = 302.1 (100%, M+) | $^1$H-NMR (300 MHz, DMSO-d6): δ [ppm] = 9.18 (d, J = 6.8 Hz, 2H), 8.54-8.45 (m, 2H), 8.42 (s, 1H), 8.35 (d, J = 7.8 Hz, 1H), 8.15 (d, J = 6.4 Hz, 1H), 8.04 (d, J = 6.7 Hz, 2H), 7.91 (t, J = 7.7 Hz, 1H), 7.80 (dd, J = 8.2 & 7.2 Hz, 1H), 6.17 (t, J = 5.4 Hz, 1H), 5.79 (s, 2H), 4.80 (d, J = 4.5 Hz, 2H). |
| 2.2 | SAPN-19c | 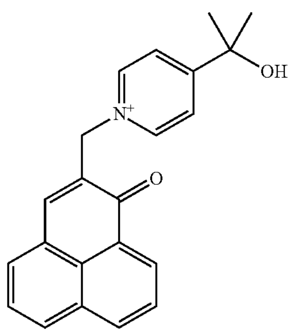 [SMILES: CC(C)(O)c1cc[n+](CC2=Cc3cccc4cccc(c34)C2=O)cc1] | MW: 330.4 + 35.45 = 365.85 g/mol MF: $C_{22}H_{20}NO_2Cl$ | MS (ESI-MS, $CH_2Cl_2$/MeOH + 10 mmol $NH_4OAc$): m/z = 330.1 (100%, M+) | $^1$H-NMR (300 MHz, DMSO-d6): δ [ppm] = 9.18 (d, J = 6.8 Hz, 2H), 8.52 (dd, J = 8.9, 7.7 Hz, 2H), 8.45 (s, 1H), 8.36 (d, J = 8.1 Hz, 1H), 8.22-8.13 (m, 3H), 7.93 (t, J = 7.7 Hz, 1H), 7.82 (dd, J = 8.1 & 7.3 Hz, 1H), 5.91 (s, 1H), 5.78 (s, 2H), 1.49 (s, 6H). |
| 2.3 | SAPN-19b | 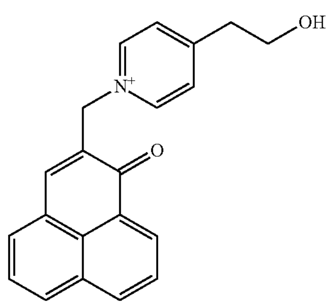 [SMILES: O=C1C(C[n+]2ccc(CCO)cc2)=Cc2cccc3cccc1c23] | MW: 316.4 + 35.45 = 351.85 g/mol MF: $C_{21}H_{18}NO_2Cl$ | MS (ESI-MS, $CH_2Cl_2$/MeOH + 10 mmol $NH_4OAc$): m/z = 316.1 (100%, M+) | $^1$H-NMR (300 MHz, DMSO-d6): δ [ppm] = 9.11 (d, J = 6.6 Hz, 2H), 8.60-8.45 (m, 2H), 8.46-8.31 (m, 2H), 8.17 (d, J = 6.9 Hz, 1H), 8.02 (d, J = 6.6 Hz, 2H), 7.93 (t, J = 7.7 Hz, 1H), 7.87-7.72 (m, 1H), 5.75 (s, 2H), 4.95 (s, 1H), 3.75 (t, J = 5.9 Hz, 2H), 3.01 (t, J = 6.0 Hz, 2H). |
| 3.1 | SAPN-35a | 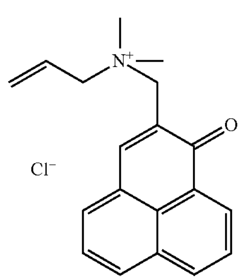 [SMILES: C=CC[N+](C)(C)CC1=Cc2cccc3cccc(c23)C1=O ; [Cl-]] | MW: 278.38 + 35.45 = 313.83 g/mol MF: $C_{19}H_{20}NOCl$ | MS (ESI-MS, $CH_2Cl_2$/MeOH + 10 mmol $NH_4OAc$): m/z = 278.2 (100%, M+) | $^1$H-NMR (300 MHz, MeOD): δ [ppm] = 8.66 (dd, J = 7.4 & 1.1 Hz, 1H), 8.49-8.37 (m, 2H), 8.36-8.24 (m, 1H), 8.18-8.06 (m, 1H), 7.91 (t, J = 7.8 Hz, 1H), 7.77 (dd, J = 8.2 & 7.2 Hz, 1H), 5.87-5.69 (m, 2H), 4.56 (s, 2H), 4.10 (d, J = 7.3 Hz, 2H), 3.11 (s, 6H). |

-continued

| Substance No. | | Structure | Molecular weight (MW)/Molecular formula (MF) | Mass spectrum (MS) | NMR |
|---|---|---|---|---|---|
| 3.2 | SAPN-35b | 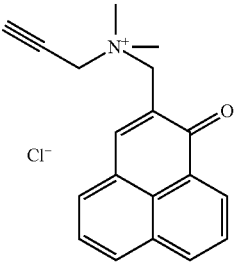 [SMILES: C#CC[N+](C)(C)CC1=Cc2cccc3cccc(c23)C1=O ; [Cl-]] | MW: 276.36 + 35.45 = 311.81 g/mol MF: C₁₉H₁₈NOCl | MS (ESI-MS, CH₂Cl₂/MeOH + 10 mmol NH₄OAc): m/z = 276.1 (100%, M+) | ¹H-NMR (300 MHz, MeOD): δ [ppm] = 8.66 (dd, J = 7.4 & 1.1 Hz, 1H), 8.51-8.37 (m, 2H), 8.30 (d, J = 8.3 Hz, 1H), 8.12 (d, J = 6.5 Hz, 1H), 7.91 (t, J = 7.8 Hz, 1H), 7.77 (dd, J = 8.2 & 7.2 Hz, 1H), 4.67 (s, 2H), 4.47 (s, 2H), 3.64 (m, 1H), 3.25 (s, 6H). |
| 3.3 | SAPN-36 | 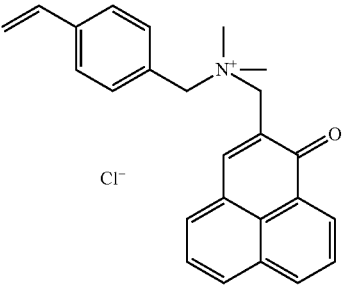 [SMILES: C=Cc1ccc(C[N+](C)(C)CC2=Cc3cccc4cccc(c34)C2=O)cc1 ; [Cl-]] | MW: 354.48 + 35.45 = 389.93 g/mol MF: C₂₅H₂₄NOCl | MS (ESI-MS, CH₂Cl₂/MeOH + 10 mmol NH₄OAc): m/z = 354.2 (100%, M+) | ¹H-NMR (300 MHz, CDCl₃): δ [ppm] = 8.92 (s, 1H), 8.57 (dd, J = 7.4 & 0.9 Hz, 1H), 8.25 (d, J = 7.3 Hz, 1H), 8.12 (d, J = 7.7 Hz, 2H), 7.79 (t, J = 7.7 Hz, 1H), 7.66 (m, 3H), 7.57 (m, 2H), 7.43 (d, J = 8.1 Hz, 2H), 7.57 (m, 2H), 6.68 (m, 1H), 5.80 (d, J = 16.8 Hz, 1H), 5.33 (d, J = 10.9 Hz, 1H), 5.15 (s, 2H), 5.03 (s, 2H), 3.19 (s, 6H). |
| 3.4 | SAPN-37a | 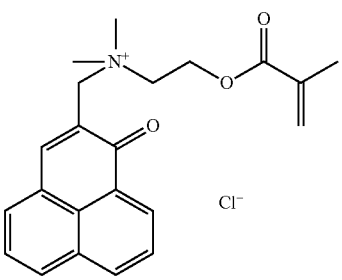 [SMILES: C=C(C)C(=O)OCC[N+](C)(C)CC1=Cc2cccc3cccc(c23)C1=O ; [Cl-]] | MW: 350.44 + 35.45 = 385.89 g/mol MF: C₂₂H₂₄NO₃Cl | MS (ESI-MS, CH₂Cl₂/MeOH + 10 mmol NH₄OAc): m/z = 350.2 (100%, M+) | ¹H-NMR (300 MHz, MeOD): δ [ppm] = 8.58 (dd, J = 7.4, 1.1 Hz, 1H), 8.52-8.32 (m, 2H), 8.25 (dd, J = 8.3 & 0.7 Hz, 1H), 8.18-8.03 (m, 1H), 7.93-7.78 (m, 1H), 7.76-7.63 (m, 1H), 6.19 (m, 1H), 5.72 (m, 1H), 4.89 (m, 2H), 4.67 (m, 2H), 3.98-3.76 (m, 2H), 3.26 (s, 6H), 1.97 (s, 3H). |
| 3.5 | SAPN-37b | 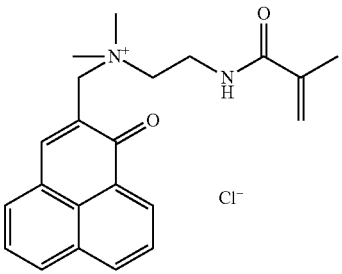 [SMILES: C=C(C)C(=O)NCC[N+](C)(C)CC1=Cc2cccc3cccc(c23)C1=O ; [Cl-]] | MW: 349.46 + 35.45 = 384.91 g/mol MF: C₂₂H₂₅N₂O₂Cl | MS (ESI-MS, CH₂Cl₂/MeOH + 10 mmol NH₄OAc): m/z = 349.2 (100%, M+) | Not measured |
| 3.6 | SA-PN-38 | 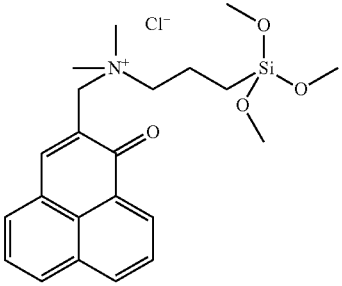 [SMILES: CO[Si](CCC[N+](C)(C)CC1=Cc2cccc3cccc(c23)C1=O)(OC)OC ; [Cl-]] | MW: 400.57 + 35.45 = 436.02 g/mol MF: C₂₂H₃₀NO₄SiCl | MS (ESI-MS, CH₂Cl₂/MeOH + 10 mmol NH₄OAc): m/z = 358.1 (100%, (M − 3Me)+) | ¹H-NMR (300 MHz, DMSO-d6): δ [ppm] = 8.81-7.29 (m, 7H), 5.67 (m, 1H), 4.55 (s, 2H), 3.64 (m, 2H), 3.45-2.98 (m, 15H), 2.03 (m, 2H), 0.77 (m, 2H). |

| Substance No. | Structure | Molecular weight (MW)/Molecular formula (MF) | Mass spectrum (MS) | NMR |
|---|---|---|---|---|
| 3.7 | SA-PN-25c-boc 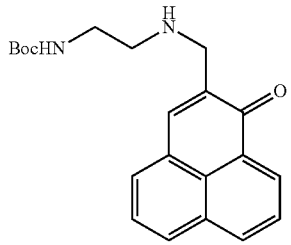 [SMILES: CC(C)(C)OC(=O)NCCNCC1=Cc2cccc3cccc(c23)C1=O] | MW: 352.44 g/mol MF: $C_{21}H_{24}N_2O_3$ | MS (ESI-MS, $CH_2Cl_2$/MeOH + 10 mmol $NH_4OAc$): m/z = 353.1 (100%, MH+) | $^1$H-NMR (300 MHz, $CDCl_3$): δ [ppm] = 8.64 (dd, J = 7.4 & 1.0 Hz, 1H), 8.21 (d, J = 8.2 Hz, 1H), 8.03 (d, J = 8.2 Hz, 1H), 7.92 (s, 1H), 7.79 (dd, J = 16.7 & 7.4 Hz, 2H), 7.65-7.57 (m, 1H), 5.40 (s, 1H), 3.98 (s, 2H), 3.41 (d, J = 5.3 Hz, 2H), 3.03-2.95 (m, 2H), 1.42 (s, 9H). |
| 3.8 | SA-PN-25a 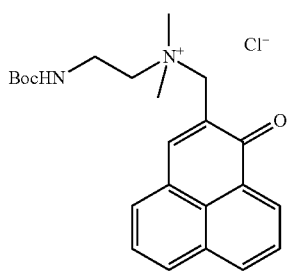 [SMILES: CC(C)(C)OC(=O)NCC[N+](C)(C)CC1=Cc2cccc3cccc(c23)C1=O ; [Cl-]] | MW: 381.50 + 35.45 = 416.95 g/mol MF: $C_{23}H_{29}N_2O_3Cl$ | MS (ESI-MS, $CH_2Cl_2$/MeOH + 10 mmol $NH_4OAc$): m/z = 381.0 (100%, M+) | $^1$H-NMR (300 MHz, DMSO-d6): δ [ppm] = 8.66-8.47 (m, 2H), 8.39 (d, J = 8.1 Hz, 1H), 8.18 (d, J = 6.8 Hz, 1H), 7.96 (t, J = 7.7 Hz, 1H), 7.83 (dd, J = 8.1 & 7.3 Hz, 1H), 7.27 (t, J = 5.1 Hz, 1H), 4.57 (s, 2H), 3.55-3.40 (m, 4H), 3.13 (s, 6H), 1.39 (s, 9H). |
| 3.9 | SA-PN-34a 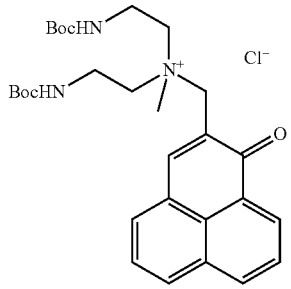 [SMILES: CC(C)(C)OC(=O)NCC[N+](C)(CCNC(=O)OC(C)(C)C)CC1=Cc2cccc3cccc(c23)C1=O ; [Cl-]] | MW: 510.66 + 35.45 = 546.12 g/mol MF: $C_{29}H_{40}N_3O_5Cl$ | MS (ESI-MS, $CH_2Cl_2$/MeOH + 10 mmol $NH_4OAc$): m/z = 510.3 (100%, M+) | $^1$H-NMR (300 MHz, $CDCl_3$): δ [ppm] = 8.89 (s, 1H), 8.58 (d, J = 7.3 Hz, 1H), 8.31-8.02 (m, 3H), 7.78 (t, J = 7.7 Hz, 1H), 7.66 (t, J = 7.7 Hz, 1H), 6.53 (s, 2H), 4.82 (s, 2H), 3.98-3.58 (m, 8H), 3.22 (s, 3H), 1.39 (s, 18H). |
| 3.10 | SA-PN-11 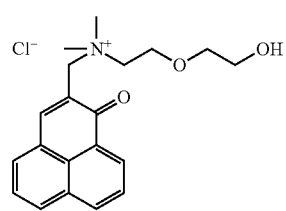 [SMILES: C[N+](C)(CCOCCO)CC1=Cc2cccc3cccc(c23)C1=O ; [Cl-]] | MW: 326.4 + 35.45 = 361.85 g/mol MF: $C_{20}H_{24}NO_3Cl$ | MS (ESI-MS, $CH_2Cl_2$/MeOH + 10 mmol $NH_4OAc$): e/z (%) = 326.2 (100, M+); | $^1$H-NMR (300 MHz, $CDCl_3$): δ [ppm] = 8.69 (s, 1H), 8.48-8.34 (m, 1H), 8.17-7.91 (m, 3H), 7.65 (t, J = 7.6 Hz, 1H), 7.56 (t, J = 7.7 Hz, 1H), 5.03-4.78 (bs, 1H), 4.81 (s, 2H), 4.06 (m, 2H), 3.84 (m, 2H), 3.69 (m, 2H), 3.63 (m, 2H), 3.30 (s, 6H). |
| 3.11 | SA-PN-12 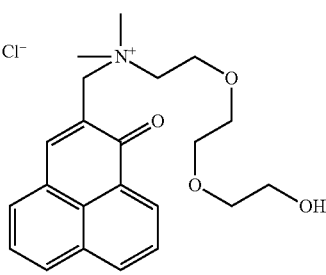 [SMILES: [Cl-] ; C[N+](C)(CCOCCOCCO)CC1=Cc2cccc3cccc(c23)C1=O] | MW: 370.5 + 35.45 = 405.95 g/mol MF: $C_{22}H_{28}NO_4Cl$ | MS (ESI-MS, $CH_2Cl_2$/MeOH + 10 mmol $NH_4OAc$): e/z (%) = 370.2 (100, M+); | $^1$H-NMR (300 MHz, DMSO): δ [ppm] = 8.65-8.45 (m, 3H), 8.39 (d, J = 8.0 Hz, 1H), 8.17 (d, J = 6.5 Hz, 1H), 7.96 (t, J = 7.7 Hz, 1H), 7.83 (dd, J = 8.2 & 7.2 Hz, 1H), 4.60 (s, 2H), 3.97 (s, 2H), 3.75-3.41 (m, 13H), 3.14 (s, 6H). |

-continued

| Substance No. | | Structure | Molecular weight (MW)/Molecular formula (MF) | Mass spectrum (MS) | NMR |
|---|---|---|---|---|---|
| 3.12 | SA-PN-09 | 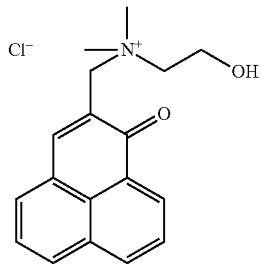 [SMILES: [Cl-] ; C[N+](C)(CCO)CC1=Cc2cccc3cccc(c23)C1=O] | MW: 282.4 + 35.45 = 317.85 g/mol MF: $C_{18}H_{20}NO_2Cl$ | MS (ESI-MS, $CH_2Cl_2$/MeOH + 10 mmol $NH_4OAc$): e/z (%) = 282.1 (100, M+); | $^1$H-NMR (300 MHz, DMSO-d6): δ [ppm] = 8.58-8.54 (dd, J = 1.0 & 7.3 Hz, 1H), 8.55-8.50 (dd, J = 1.2 & 7.4 Hz, 1H), 8.52 (s, 1H), 8.37 (dd, J = 1.0 & 7.8 Hz, 1H), 8.18 (dd, J = 0.9 Hz, J = 7.1 Hz, 1H), 7.95 (t, J = 7.7 Hz, 1H), 7.84-7.78 (m, 1H), 5.62 (t, J = 5.1 Hz, 1H), 4.61 (s, 2H), 3.99-3.88 (m, 2H), 3.59-3.51 (m, 2H), 3.15 (s.6H). |
| 4 | PNOH | 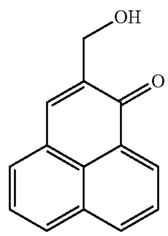 [SMILES: O=C1C(CO)=Cc2cccc3cccc1c23] | MW: 210.33 g/mol MF: $C_{14}H_{10}NO_2$ | MS (ESI-MS, $CH_2Cl_2$/MeOH + 10 mmol $NH_4OAc$): m/z = 211.1 (100%, MH+), 193.1 (64%, MH+ − $H_2O$) | $^1$H-NMR (300 MHz, CDCl$_3$): δ [ppm] = 8.66 (dd, J = 7.4 & 1.2 Hz, 1H), 8.22 (dd, J = 8.1, 1.1 Hz, 1H), 8.01 (m, 2H), 7.89-7.74 (m, 2H), 7.62 (dd, J = 8.2 & 7.1 Hz, 1H), 4.82 (d, J = 1.4 Hz, 2H). |
| 5.1 | PN-AMO-07a | 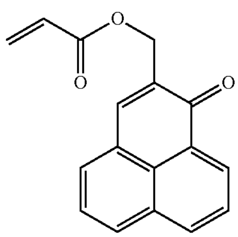 [SMILES: C=CC(=O)OCC1=Cc2cccc3cccc(c23)C1=O] | MW: 264.28 g/mol MF: $C_{17}H_{12}O_3$ | MS (ESI-MS, $CH_2Cl_2$/MeOH + 10 mmol $NH_4OAc$): m/z = 265.1 (100%, MH+) | $^1$H-NMR (300 MHz, CDCl$_3$): δ [ppm] = 8.67 (d, J = 7.4 Hz, 1H), 8.23 (d, J = 8.0 Hz, 1H), 8.03 (d, J = 8.4 Hz, 2H), 7.87-7.76 (m, 2H), 7.65-7.59 (m, 1H), 6.64 (d, J = 16.6 Hz, 1H), 6.35 (dd, J = 16.6, 10.1 Hz, 1H), 6.18 (d, J = 10.1 Hz, 1H), 4.83 (s, 2H). |
| 5.2 | PN-AMO-07b | 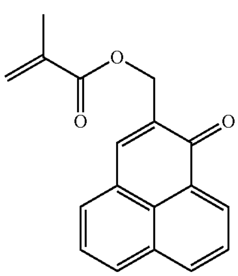 [SMILES: C=C(C)C(=O)OCC1=Cc2cccc3cccc(c23)C1=O] | MW: 278.31 g/mol MF: $C_{18}H_{14}O_3$ | MS (ESI-MS, $CH_2Cl_2$/MeOH + 10 mmol $NH_4OAc$): m/z = 279.1 (100%, MH+) | Not measured |
| 5.3 | PN-AMO-08 | 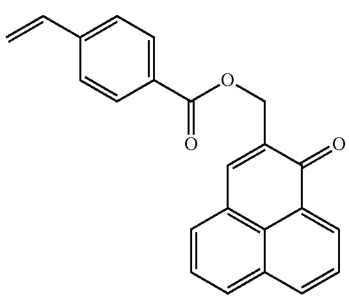 [SMILES: C=Cc1ccc(C(=O)OCC2=Cc3cccc4cccc(c34)C2=O)cc1] | MW: 340.38 g/mol MF: $C_{23}H_{16}O_3$ | MS (ESI-MS, $CH_2Cl_2$/MeOH + 10 mmol $NH_4OAc$): m/z = 341.1 (100%, MH+) | $^1$H-NMR (300 MHz, CDCl$_3$): δ [ppm] = 8.69 (d, J = 7.4 Hz, 1H), 8.25 (d, J = 8.1 Hz, 1H), 8.22 (d, J = 8.4 Hz, 2H), 8.05 (d, J = 8.4 Hz, 2H), 7.89-7.74 (m, 2H), 7.67-7.62 (m, 1H), 7.58 (d, J = 8.3 Hz, 2H), 6.90-6.73 (m, 2H), 5.94 (d, J = 17.5 Hz, 1H), 5.48 (d, J = 10.8 Hz, 1H), 4.85 (s, 1H). |

-continued

| Substance No. | | Structure | Molecular weight (MW)/Molecular formula (MF) | Mass spectrum (MS) | NMR |
|---|---|---|---|---|---|
| 6.1 | PN-AMO-04a | 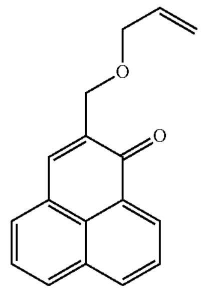 [SMILES: C=CCOCC1=Cc2cccc3cccc(c23)C1=O] | MW: 250.30 g/mol MF: $C_{17}H_{14}O_2$ | MS (ESI-MS, $CH_2Cl_2$/MeOH + 10 mmol $NH_4OAc$): m/z = 193.1 (52%, MH+ −C3H6O), 251.1 (100%, MH+), 273.1 (13%, MNa+) | $^1$H-NMR (300 MHz, $CDCl_3$): δ [ppm] = 8.63 (d, J = 7.4 Hz, 1H), 8.19 (d, J = 8.1 Hz, 1H), 7.99 (d, J = 8.3 Hz, 1H), 7.85 (m, 1H), 7.75 (m, 2H), 7.58 (t, J = 7.7 Hz, 1H), 6.06 (m, 1H), 5.40 (dd, J = 17.2 & 1.6 Hz, 1H), 5.26 (dd, J = 10.4 & 1.1 Hz, 1H), 4.61 (s, 2H), 4.20 (d, J = 5.6 Hz, 2H). |
| 6.2 | PN-AMO-04b | 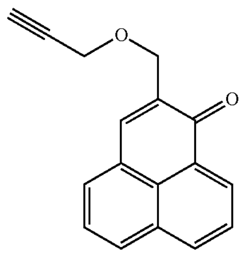 [SMILES: C#CCOCC1=Cc2cccc3cccc(c23)C1=O] | MW: 248.28 g/mol MF: $C_{17}H_{12}O_2$ | MS (ESI-MS, $CH_2Cl_2$/MeOH + 10 mmol $NH_4OAc$): m/z = 249.1 (100%, MH+) | $^1$H-NMR (300 MHz, $CDCl_3$): δ [ppm] = 8.66 (dd, J = 7.4, 1.1 Hz, 1H), 8.22 (dd, J = 8.0, 0.9 Hz, 1H), 8.02 (d, J = 8.1 Hz, 1H), 7.87 (t, J = 1.4 Hz, 1H), 7.79 (t, J = 7.7 Hz, 2H), 7.61 (dd, J = 8.2, 7.2 Hz, 1H), 4.71 (d, J = 1.5 Hz, 2H), 4.37 (d, J = 2.4 Hz, 2H), 2.51 (t, J = 2.4 Hz, 1H). |
| 6.3 | PN-AMO-06 | 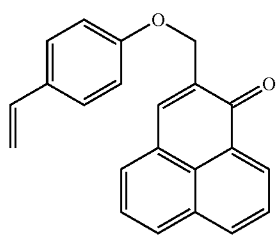 [SMILES: C=Cc1ccc(OCC2=Cc3cccc4cccc(c34)C2=O)cc1] | MW: 312.37 g/mol MF: $C_{22}H_{16}O_2$ | MS (ESI-MS, $CH_2Cl_2$/MeOH + 10 mmol $NH_4OAc$): m/z = 313.1 (100%, MH+) | $^1$H-NMR (300 MHz, $CDCl_3$): δ [ppm] = 8.70 (d, J = 6.4 Hz, 1H), 8.25 (d, J = 8.1 Hz, 1H), 8.04 (d, J = 8.1 Hz, 1H), 7.95 (s, 1H), 7.86-7.78 (m, 2H), 7.66-7.58 (m, 1H), 7.38 (d, J = 8.7 Hz, 2H), 7.03 (d, J = 8.7 Hz, 2H), 6.67 (dd, J = 17.6, 10.9 Hz, 1H), 5.63 (d, J = 17.6 Hz, 1H), 5.20 (d, J = 1.5 Hz, 2H), 5.14 (d, J = 11.0 Hz, 1H). |
| 6.4 | PN-AMO-05 | 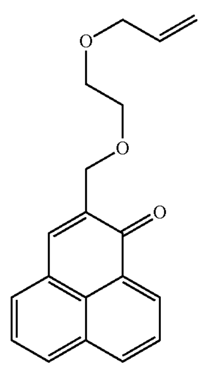 [SMILES: C=CCOCCOCC1=Cc2cccc3cccc(c23)C1=O] | MW: 294.35 g/mol MF: $C_{19}H_{18}O_3$ | MS (ESI-MS, $CH_2Cl_2$/MeOH + 10 mmol $NH_4OAc$): m/z = 193.1 (27%, MH+ −C5H10O2), 295.1 (100%, MH+), 317.1 (10%, MNa+) | $^1$H-NMR (300 MHz, $CDCl_3$): δ [ppm] = 8.63 (dd, J = 7.4 & 1.1 Hz, 1H), 8.19 (dd, J = 8.1 & 0.9 Hz, 1H), 7.99 (d, J = 8.1 Hz, 1H), 7.89 (t, J = 1.5 Hz, 1H), 7.76 (t, J = 7.6 Hz, 2H), 7.58 (dd, J = 8.2 & 7.2 Hz, 1H), 5.94 (m, 1H), 5.32 (ddd, J = 17.2 & 3.2 & 1.6 Hz, 1H), 5.26-5.16 (m, 1H), 4.66 (d, J = 1.5 Hz, 2H), 4.09 (dt, J = 5.6 & 1.3 Hz, 2H), 3.83 (m, 2H), 3.72 (m, 2H). |
| 6.5 | PN-AMO-10 | 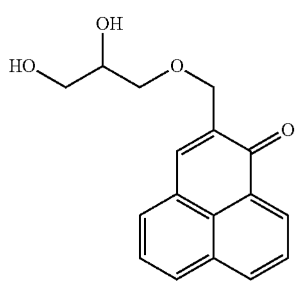 [SMILES: O=C1C(COCC(O)CO)=Cc2cccc3cccc1c23] | MW: 284.31 g/mol MF: $C_{17}H_{16}O_4$ | MS (ESI-MS, $CH_2Cl_2$/MeOH + 10 mmol $NH_4OAc$): m/z = 285.1 (100%, MH+), 263.1 (29%, MH+ − $H_2O$) | $^1$H-NMR (300 MHz, $CDCl_3$): δ [ppm] = 8.62 (d, J = 7.6 Hz, 1H), 8.20 (d, J = 8.1 Hz, 1H), 7.97 (d, J = 8.2 Hz, 1H), 7.87 (s, 1H), 7.76 (t, J = 7.5 Hz, 2H), 7.56 (t, J = 7.6 Hz, 1H), 4.61 (s, 2H), 4.12-3.56 (m, 7H). |

-continued

| Substance No. | | Structure | Molecular weight (MW)/Molecular formula (MF) | Mass spectrum (MS) | NMR |
|---|---|---|---|---|---|
| 6.6 | PN-AMO-02b | 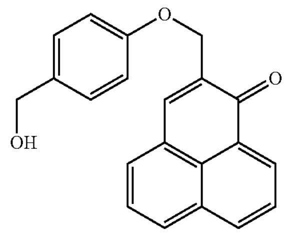 [SMILES: O=C1C(COc2ccc(CO)cc2)=Cc2cccc3cccc1c23] | MW: 316.36 g/mol MF: $C_{21}H_{16}O_3$ | MS (ESI-MS, $CH_2Cl_2$/MeOH + 10 mmol $NH_4OAc$): m/z = 317.1 (100%, MH+) | $^1$H-NMR (300 MHz, $CDCl_3$): δ [ppm] = 8.69 (d, J = 7.4 Hz, 1H), 8.23 (d, J = 8.1 Hz, 1H), 7.98 (d, J = 8.1 Hz, 1H), 7.93 (s, 1H), 7.78-7.73 (m, 2H), 7.62-7.51 (m, 1H), 7.01 (d, J = 7.8 Hz, 2H), 6.78 (d, J = 7.8 Hz, 2H), 5.26 (m, 2H), 4.46 (s, 2H). |
| 6.7 | PN-AMO-02a | 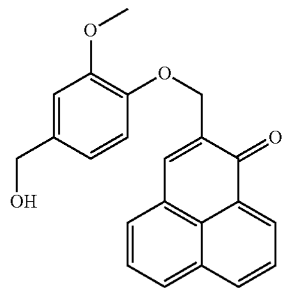 [SMILES: COc1cc(CO)ccc1OCC1=Cc2cccc3cccc(c23)C1=O] | MW: 346.39 g/mol MF: $C_{22}H_{18}O_4$ | MS (ESI-MS, $CH_2Cl_2$/MeOH + 10 mmol $NH_4OAc$): m/z = 347.1 (100%, MH+), 369.1 (9%, MNa+) | $^1$H-NMR (300 MHz, $CDCl_3$): δ [ppm] = 8.67 (dd, J = 7.3 & 0.9 Hz, 1H), 8.21 (d, J = 8.0 Hz, 1H), 8.01 (d, J = 8.2 Hz, 1H), 7.94 (s, 1H), 7.78 (dd, J = 10.8 & 4.4 Hz, 2H), 7.65-7.52 (m, 1H), 6.97-6.89 (m, 2H), 6.84 (dd, J = 8.2 & 1.7 Hz, 1H), 5.24 (d, J = 1.3 Hz, 2H), 4.63 (s, 2H), 3.95 (s, 3H). |
| 7.1 | PN-AMO-14a | 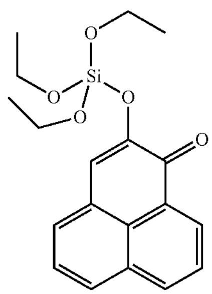 | MW: 372.50 g/mol MF: $C_{20}H_{24}O_5Si$ | MS (ESI-MS, $CH_2Cl_2$/MeOH + 10 mmol $NH_4OAc$): m/z = 373.1 (13%, MH+), 286.1 (100%, (M − 3$C_2H_5$)+) | $^1$H-NMR (300 MHz, $CDCl_3$): δ [ppm] = 8.67 (d, J = 7.4 Hz, 1H), 8.22 (d, J = 7.5 Hz, 1H), 8.03 (d, J = 8.6 Hz, 2H), 7.90-7.74 (m, 2H), 7.67-7.57 (m, 1H), 4.82 (s, 2H), 3.76-3.69 (m, 6H), 1.26 (d, J = 7.0 Hz, 9H). |
| 7.2 | PN-AMO-14b | 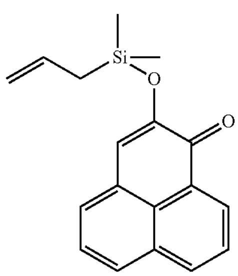 | MW: 308.46 g/mol MF: $C_{19}H_{20}O_2Si$ | MS (ESI-MS, $CH_2Cl_2$/MeOH + 10 mmol $NH_4OAc$): m/z = 309.1 (26%, MH+), 193.1 (100%, (M − $H_2O$ − $C_5H_{11}Si$)+) | $^1$H-NMR (300 MHz, $CDCl_3$): δ [ppm] = 8.67 (d, J = 7.4 Hz, 1H), 8.22 (d, J = 8.2 Hz, 1H), 8.03 (d, J = 8.4 Hz, 2H), 7.90-7.74 (m, 2H), 7.68-7.57 (m, 1H), 4.98 (dd, J = 28.1, 14.7 Hz, 1H), 4.83 (s, 2H), 1.72 (dt, J = 6.4, 1.6 Hz, 1H), 0.51 (d, J = 5.2 Hz, 1H), 0.23-0.07 (m, 6H). |
| 8.1 | PN-AMO-12a | 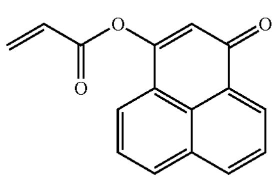 [SMILES: C=CC(=O)OC1=CC(=O)c2cccc3cccc1c23] | MW: 250.26 g/mol MF: $C_{16}H_{10}O_3$ | MS (ESI-MS, $CH_2Cl_2$/MeOH + 10 mmol $NH_4OAc$): m/z = 251.1 (100%, MH+) | $^1$H-NMR (300 MHz, $CDCl_3$): δ [ppm] = 8.70 (d, J = 7.3 Hz, 1H), 8.57 (d, J = 6.6 Hz, 1H), 8.27 (d, J = 8.0 Hz, 1H), 8.19 (d, J = 7.8 Hz, 1H), 8.11 (s, 1H), 7.79 (dt, J = 21.7, 7.8 Hz, 2H), 6.70 (dd, J = 17.3, 1.1 Hz, 1H), 6.41 (dd, J = 17.3 & 10.4 Hz, 1H), 6.11 (dd, J = 10.4 & 1.1 Hz, 1H). |
| 8.2 | PN-AMO-12b | 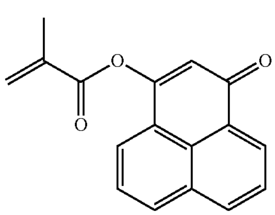 [SMILES: C=C(C)C(=O)OC1=CC(=O)c2cccc3cccc1c23] | MW: 264.28 g/mol MF: $C_{17}H_{12}O_3$ | MS (ESI-MS, $CH_2Cl_2$/MeOH + 10 mmol $NH_4OAc$): m/z = 265.1 (100%, MH+) | Not measured |

| Substance No. | | Structure | Molecular weight (MW)/Molecular formula (MF) | Mass spectrum (MS) | NMR |
|---|---|---|---|---|---|
| 8.3 | PN-AMO-12c | 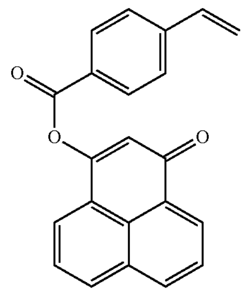 [SMILES: C=Cc1ccc(C(=O)OC2=CC(=O)c3cccc4cccc2c34)cc1] | MW: 326.36 g/mol MF: $C_{22}H_{14}O_3$ | MS (ESI-MS, $CH_2Cl_2$/MeOH + 10 mmol $NH_4OAc$): m/z = 327.1 (100%, MH+) | $^1$H-NMR (300 MHz, CDCl$_3$): δ [ppm] = 8.55 (d, J = 7.3 Hz, 1H), 8.19 (d, J = 8.3 Hz, 2H), 8.12 (d, J = 8.0 Hz, 1H), 8.00 (d, J = 8.2 Hz, 1H), 7.91 (d, J = 7.2 Hz, 1H), 7.69 (t, J = 7.7 Hz, 1H), 7.61-7.48 (m, 3H), 6.91-6.60 (m, 2H), 5.92 (d, J = 17.6 Hz, 1H), 5.45 (d, J = 10.9 Hz, 1H). |
| 9.1 | PN-AMO-11a | 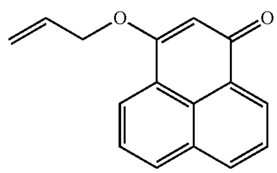 [SMILES: C=CCOC1=CC(=O)c2cccc3cccc1c23] | MW: 236.27 g/mol MF: $C_{16}H_{12}O_2$ | MS (ESI-MS, $CH_2Cl_2$/MeOH + 10 mmol $NH_4OAc$): m/z = 237.1 (100%, MH+) | $^1$H-NMR (300 MHz, CDCl$_3$): δ [ppm] = 8.59 (dd, J = 7.3, 1.1 Hz, 1H), 8.31 (dd, J = 7.3, 0.9 Hz, 1H), 8.22-8.14 (m, 1H), 8.08 (d, J = 7.5 Hz, 1H), 7.78-7.57 (m, 2H), 6.23-6.08 (m, 2H), 5.55 (dd, J = 17.3, 1.4 Hz, 1H), 5.42 (dd, J = 10.5, 1.2 Hz, 1H), 4.73 (d, J = 5.4 Hz, 2H). |
| 9.2 | PN-AMO-11b | 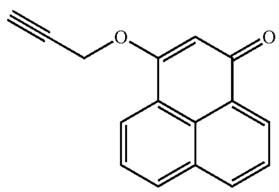 [SMILES: C#CCOC1=CC(=O)c2cccc3cccc1c23] | MW: 234.26 g/mol MF: $C_{16}H_{10}O_2$ | MS (ESI-MS, $CH_2Cl_2$/MeOH + 10 mmol $NH_4OAc$): m/z = 235.1 (100%, MH+) | 1H-NMR (300 MHz, CDCl$_3$): δ [ppm] = 8.56 (d, J = 7.2 Hz, 1H), 8.47 (d, J = 7.3 Hz, 1H), 8.20 (d, J = 8.0 Hz, 1H), 8.10 (d, J = 8.1 Hz, 1H), 7.81-7.63 (m, 2H), 7.57 (s, 1H), 4.35-4.10 (m, 2H), 2.63 (s, 1H). |
| 9.3 | PN-AMO-13 | 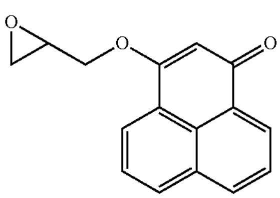 [SMILES: O=C1C=C(OCC2CO2)c2cccc3cccc1c23] | MW: 252.27 g/mol MF: $C_{16}H_{12}O_3$ | MS (ESI-MS, $CH_2Cl_2$/MeOH + 10 mmol $NH_4OAc$): m/z = 253.1 (100%, MH+) | $^1$H-NMR (300 MHz, CDCl$_3$): δ [ppm] = 8.59 (dd, J = 7.1 & 0.9 Hz, 1H), 8.29 (m, 2H), 8.17 (d, J = 7.6 Hz, 1H), 7.47 (t, J = 7.8 Hz, 1H), 7.31 (t, J = 7.8 Hz, 1H), 7.16 (m, 1H), 4.18 (dd, J = 11.4 & 4.6 Hz, 1H), 3.93 (dd, J = 11.2 & 5.8 Hz, 1H), 3.31 (m, 1H), 2.88 (m, 1H), 2.69 (m, 1H). |
| 9.4 | PN-AMO-03a | 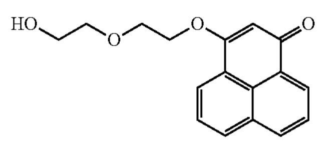 [SMILES: O=C1C=C(OCCOCCO)c2cccc3cccc1c23] | MW: 284.31 g/mol MF: $C_{17}H_{16}O_4$ | MS (ESI-MS, $CH_2Cl_2$/MeOH + 10 mmol $NH_4OAc$): m/z = 285.1 (100%, MH+) | $^1$H-NMR (300 MHz, CDCl$_3$): δ [ppm] = 8.26 (dd, J = 7.2 & 0.8 Hz, 1H), 7.94-7.74 (m, 2H), 7.66 (d, J = 7.9 Hz, 1H), 7.43 (t, J = 7.7 Hz, 1H), 7.23 (t, J = 7.8 Hz, 1H), 5.79 (s, 1H), 4.13-3.97 (m, 2H), 3.88-3.79 (m, 2H), 3.77-3.69 (m, 2H), 3.68-3.51 (m, 3H). |
| 9.5 | PN-AMO-03b | 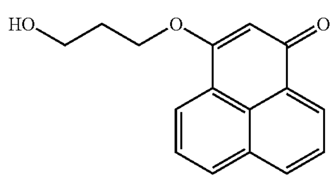 [SMILES: O=C1C=C(OCCCO)c2cccc3cccc1c23] | MW: 254.29 g/mol MF: $C_{16}H_{14}O_3$ | MS (ESI-MS, $CH_2Cl_2$/MeOH + 10 mmol $NH_4OAc$): m/z = 255.1 (100%, MH+) | H-NMR (300 MHz, MeOD): δ [ppm] = 8.66-8.58 (m, 1H), 8.45 (m, 2H), 8.27 (m, 1H), 7.96-7.72 (m, 3H), 3.22 (t, J = 7.1 Hz, 2H), 2.47 (m, 2H), 1.81 (m, 2H). |
| 9.6 | SAPN-32boc | 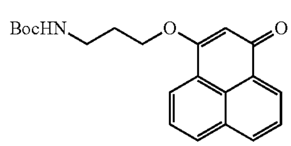 [SMILES: CC(C)(C)OC(=O)NCCCOC1=CC(=O)c2cccc3cccc1c23] | MW: 353.42 g/mol MF: $C_{21}H_{23}NO_4$ | MS (ESI-MS, $CH_2Cl_2$/MeOH + 10 mmol $NH_4OAc$): m/z = 354.2 (100%, MH+) | $^1$H-NMR (300 MHz, CDCl$_3$): δ [ppm] = 8.56 (dd, J = 7.3 & 1.0 Hz, 1H), 8.22 (d, J = 7.2 Hz, 1H), 8.19-8.11 (m, 1H), 8.05 (d, J = 7.9 Hz, 1H), 7.72 (t, J = 7.7 Hz, 1H), 7.67-7.55 (m, 1H), 6.13 (s, 1H), 4.81 (s, 1H), 4.22 (t, |

| Sub-stance No. | Structure | Molecular weight (MW)/Molecular formula (MF) | Mass spectrum (MS) | NMR |
|---|---|---|---|---|
| | | | | J = 5.9 Hz, 2H), 3.43 (s, 2H), 2.14 (p, J = 6.3 Hz, 2H), 1.45 (s, 9H). |
| 10 | SAPN-02c 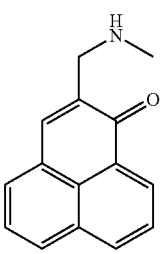 [SMILES: CNCC1=Cc2cccc3cccc(c23)C1=O] | MW: 223.28 g/mol MF: C₁₅H₁₃NO | MS (ESI-MS, CH₂Cl₂/MeOH + 10 mmol NH₄OAc): m/z = 223.1 (100%, M+) | H-NMR (300 MHz, MeOD): δ [ppm] = 8.68 (dd, J = 7.4 & 1.0 Hz, 1H), 8.51-8.38 (m, 1H), 8.27 (d, J = 7.9 Hz, 1H), 8.20 (s, 1H), 8.07 (d, J = 7.0 Hz, 1H), 7.91 (t, J = 7.8 Hz, 1H), 7.76 (dd, J = 8.2 & 7.2 Hz, 1H), 4.21 (s, 2H), 2.79 (s, 3H). |
| 11.1 | PN-AMO-09a 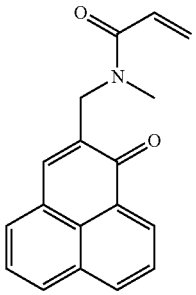 | MW: 291.35 g/mol MF: C₁₉H₁₇NO₂ | MS (ESI-MS, CH2Cl2/MeOH + 10 mmol NH4OAc): m/z = 292.1 (100%, MH+) | ¹H-NMR (300 MHz, CDCl3): δ [ppm] = 8.72-8.59 (m, 1H), 8.30-8.16 (m, 1H), 8.02 (dd, J = 14.3 & 8.2 Hz, 1H), 7.85-7.72 (m, 2H), 7.60 (m, 1H), 7.47 (s, 1H), 6.62 (m, 1H), 6.41 (m, 1H), 5.70 (m, 1H), 4.72-4.60 (m, 2H), 3.20 (d, J = 27.8 Hz, 3H). |
| 11.2 | PN-AMO-09b 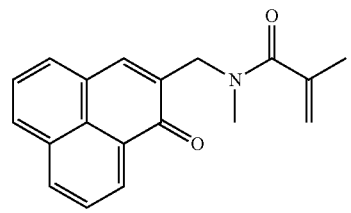 | MW: 277.33 g/mol MF: C₁₈H₁₅NO₃ | MS (ESI-MS, CH2Cl2/MeOH + 10 mmol NH4OAc): m/z = 278.1 (100%, MH+) | Not measured |
| 12 | PN-AMO-01 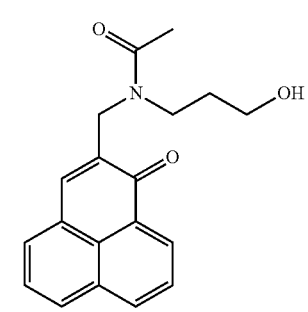 [SMILES: CC(=O)N(CCCO)CC1=Cc2cccc3cccc(c23)C1=O] | MW: 309.37 g/mol MF: C₁₉H₁₉NO₃ | MS (ESI-MS, CH₂Cl₂/MeOH + 10 mmol NH₄OAc): m/z = 310.1 (100%, MH+) | ¹H-NMR (300 MHz, CDCl₃): δ [ppm] = 8.69 (dd, J = 1.2 & 7.4 Hz, 1H), 8.26 (dd, J = 1.0 & 8.1 Hz, 1H), 8.08 (dd, J = 0.6 & 8.2 Hz, 1H), 7.78-7.90 (m, 2H), 7.62 (dd, J = 7.0 & 1.2 Hz, 1H), 7.51 (s, 1H), 4.65 (s, 2H), 3.83 (bs, 1H), 3.66 (t, J = 5.6 Hz, 2H), 3.59 (t, J = 5.6 Hz, 2H), 2.16 (s, 3H), 1.78 (m, 2H). |
| 13.1 | SA-PN-25c 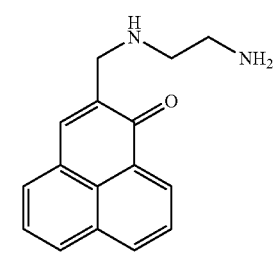 [SMILES: NCCNCC1=Cc2cccc3cccc(c23)C1=O] | MW: 252.32 g/mol MF: C₁₆H₁₆N₂O | MS (ESI-MS, CH₂Cl₂/MeOH + 10 mmol NH₄OAc): m/z = 253.1 (100%, MH+) | H-NMR (300 MHz, MeOD): δ [ppm] = 8.71 (dd, J = 7.4 & 1.0 Hz, 1H), 8.46 (d, J = 8.1 Hz, 1H), 8.29 (t, J = 3.9 Hz, 2H), 8.10 (d, J = 7.1 Hz, 1H), 7.92 (t, J = 7.8 Hz, 1H), 7.77 (dd, J = 8.2 & 7.2 Hz, 1H), 4.33 (s, 2H), 3.46 (m, 4H). |

-continued

| Sub-stance No. | Structure | Molecular weight (MW)/Molecular formula (MF) | Mass spectrum (MS) | NMR |
|---|---|---|---|---|
| 13.2 | SA-PN-25b | MW: 281.38 + 35.45 = 316.83 g/mol<br>MF: $C_{18}H_{21}N_2OCl$ | MS (ESI-MS, $CH_2Cl_2$/MeOH + 10 mmol $NH_4OAc$): m/z = 281.1 (100%, M+) | $^1$H-NMR (300 MHz, DMSO-d6): δ [ppm] = 8.68 (s, 3H), 8.57 (dd, J = 10.0 & 6.5 Hz, 3H), 8.40 (d, J = 8.3 Hz, 1H), 8.22 (d, J = 7.0 Hz, 1H), 7.97 (t, J = 7.7 Hz, 1H), 7.91-7.76 (m, 1H), 4.62 (s, 2H), 3.77-3.65 (m, 2H), 3.43 (m, 2H), 3.20 (s, 6H). |
| 13.3 | SA-PN-34b | MW: 310.42 + 35.45 = 345, 87 g/mol<br>MF: $C_{19}H_{24}N_3O$ | MS (ESI-MS, $CH_2Cl_2$/MeOH + 10 mmol $NH_4OAc$): m/z = 310.1 (100%, M+) | H-NMR (300 MHz, MeOD): δ [ppm] = 8.74 (dd, J = 7.5 & 0.9 Hz, 1H), 8.47 (d, J = 8.0 Hz, 1H), 8.31 (t, J = 3.8 Hz, 2H), 8.12 (d, J = 7.2 Hz, 1H), 7.93 (t, J = 7.6 Hz, 1H), 7.79 (dd, J = 8.2 & 7.4 Hz, 1H), 4.35 (s, 2H), 3.58-3.35 (m, 8H). |
| 13.4 | SAPN-32 | MW: 253.30 g/mol<br>MF: $C_{16}H_{15}NO_2$ | MS (ESI-MS, $CH_2Cl_2$/MeOH + 10 mmol $NH_4OAc$): m/z = 254.1 (100%, MH+) | H-NMR (300 MHz, MeOD): δ [ppm] = 8.62-8.50 (m, 1H), 8.42 (m, 2H), 8.26 (m, 1H), 7.98-7.70 (m, 3H), 3.05 (t, J = 7.0 Hz, 2H), 2.88-2.78 (m, 2H), 1.86 (dd, J = 9.5 & 3.6 Hz, 2H). |

Example 2: Production of Antimicrobial Surface Coatings

The photosensitizers produced in Example 1 were tested in a variety of paint systems, as follows.

1) 2-Component (2-C) Polyurethane Paint, Containing Solvent

The respective photosensitizer (0.06 mmol) was dissolved in 100 mL of clear basic paint (polyisocyanate cross-linkable, hydroxyl group-containing acrylic resin, 20% in xylene/n-butyl acetate). The cross-linking agent (hexamethylene diisocyanate (HDI)—containing polymer, 20% in xylene/n-butyl acetate, "Desmodur® N75" from Covestro AG, Leverkusen, DE) was mixed with the basic paint in a ratio of 5:1 (v/v). The viscous, pale yellow solution was applied to a variety of degreased surfaces using a spray gun. The tested substances were PMMA, PVC, glass, aluminium, stainless steel and wood. After drying for 4 h at room temperature, complete hardening was obtained by heating to 60° C. for 30 min.

The following photosensitizers were processed using this method:

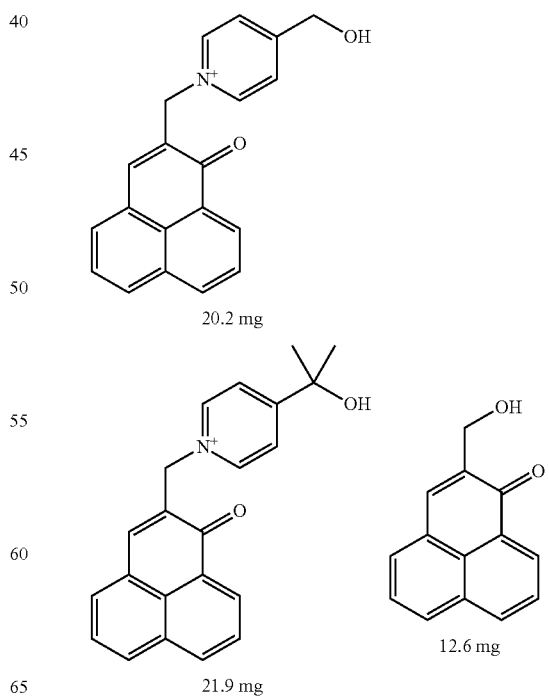

20.2 mg 21.9 mg 12.6 mg

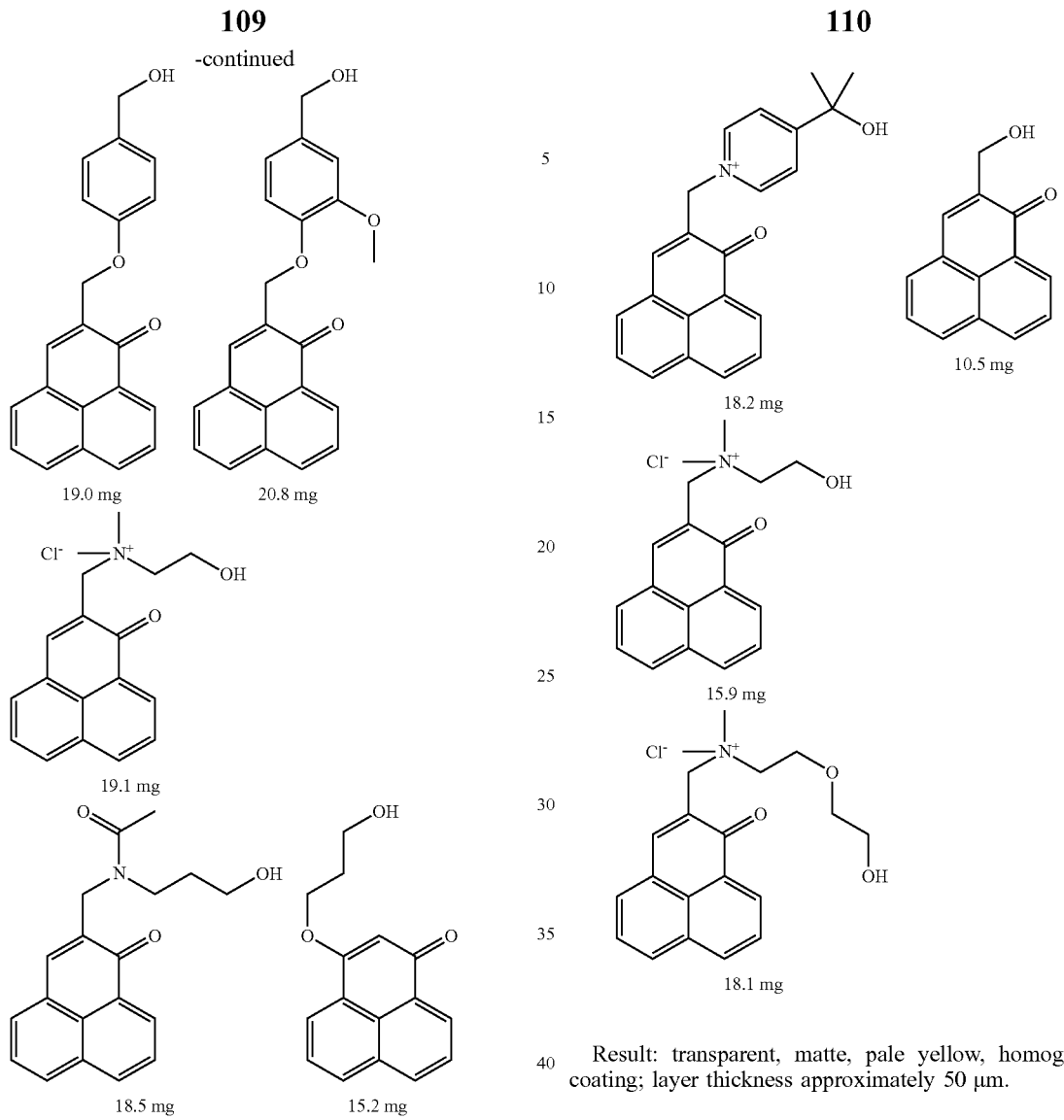

Result: transparent, pale yellow, homogeneous coating; layer thickness between 20 and 40 μm.

2) 1-Component (1-C) Polyurethane Paint, Water-Based

The respective photosensitizer (0.05 mmol) was dissolved in the water-based paint (100 mL, acrylic-polyurethane emulsion, fatty acid-modified, 20% in water). The mixture was vigorously stirred for 30 min at room temperature. The paint was applied evenly to i) an untreated wooden board, ii) PMMA plates or iii) PVC plates using a brush. Alternatively, the paint was applied using a spray gun, evenly from a distance of approximately 30 cm. The coating was allowed to dry in air and was allowed to harden overnight at room temperature.

The following photosensitizers were processed using this method:

Result: transparent, matte, pale yellow, homogeneous coating; layer thickness approximately 50 μm.

3) 2-C Epoxy Resins

Composition of Basic Resins (Typical Technical Products):

Formulation I (resin with reactive diluent): bisphenol-A-epichlorohydrin resin with mean molecular weight of <700 g/mol (25-50%)

C12-C14 aliphatic glycidyl ether (25-50%)

alkylglycidyl ether (5-25%)

Formulation II (resin with reactive diluent): bisphenol-A-epichlorohydrin resin with mean molecular weight of <700 g/mol (60-80%)

1,4-bis(2,3-epoxypropoxy)butane (20-40%)

Formulation III (resin with reactive diluent): bisphenol-A-epichlorohydrin resin with mean molecular weight of <700 g/mol (75-90%)

hexanediol diglycidyl ether (10-25%)

Formulation IV (resin with reactive diluent): bisphenol-A-epichlorohydrin resin with mean molecular weight of <700 g/mol (50-90%)

bisphenol F epoxy resin (25-50%)

C12-C14 aliphatic glycidyl ether (10-20%)

1,4-bis(2,3-epoxypropoxy)butane (10-20%)

Composition of Hardener (Typical Technical Products);

Formulation I (normal hardener): isophorone diamine (aminomethyl-3,5,5-trimethyl-cyclohexylamine) (10-25%)
benzyl alcohol (25-50%)
2,2,4-trimethylhexane-1,6-diamine (3-10%)

Formulation II (normal hardener): isophorone diamine (aminomethyl-3,5,5-trimethyl-cyclohexylamine) (44%)
xylidene diamine (10%)
trimethylhexamethylene diamine (5%)
salicylic acid (1%)
polyethylene amine (10%)
benzyl alcohol (30%)

Formulation III (rapid hardener): diaminocyclohexane (18%)
pentamethylene diamine (25%)
salicylic acid (2%)
polyethylene amine (20%)
benzyl alcohol (35%)

Optionally with accelerator/catalyst: N-benzyldimethylamine (BDMA) and/or
N, N, N, N-tetramethyl-1,3-butanediamine (TMBDA) and/or
2-methyl imidazole (2MI)

Variation a)

The respective photosensitizer (0.05 mmol) was dissolved in 25 mL of the clear hardener (formulation I or II). From the basic resin (formulation II, III or IV), 75 mL was mixed with the hardener. The viscous, pale yellow solution was applied to degreased surfaces formed from i) PMMA or ii) PVC using a spray gun.

Alternatively, the mixture was applied with a brush several times in even coats to untreated wood, in order to obtain an antimicrobial seal. After hardening for 12 h at room temperature, post-hardening was carried out by heating to 40° C. for 6 h.

The following photosensitizers were processed using this method:

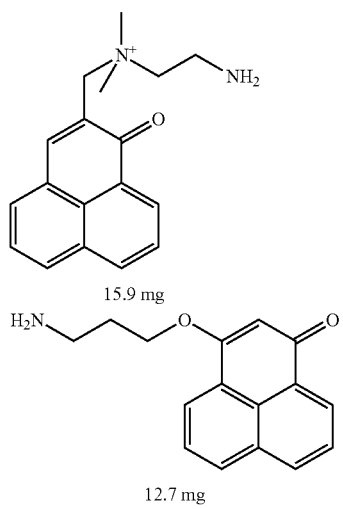

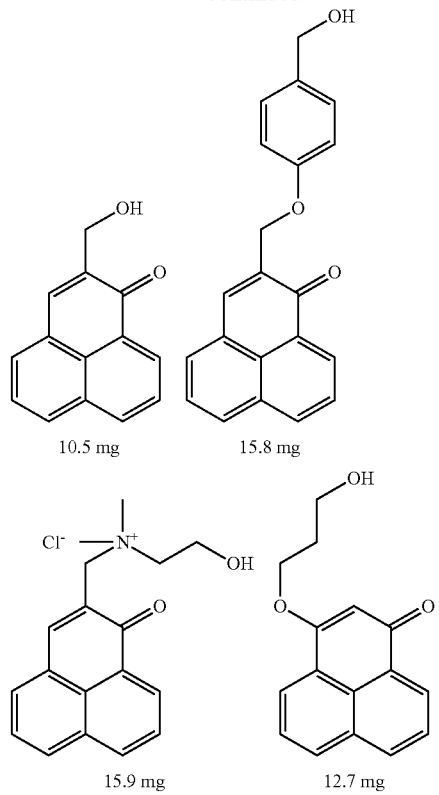

Result: transparent, pale yellow, homogeneous coating; layer thickness between 20 and 40 µm.

Variation b)

The respective photosensitizer (0.05 mmol) was dissolved in 30 mL of the clear hardener (formulation II or III). From the basic resin (formulation I), 70 mL was mixed with the hardener. A flat stainless steel pan was evenly coated with release wax. In it, i) a glass fibre mat, ii) a piece of CFRP fabric or iii) a piece of aramid fabric (each 20×20 cm²) was evenly impregnated with the resin mixture with a brush so that the fabric could completely take up the mixture. After hardening for 24 hours at room temperature, post-hardening was carried out by slowly heating to 60° C. and holding for 30 min.

The following photosensitizers were processed using this method:

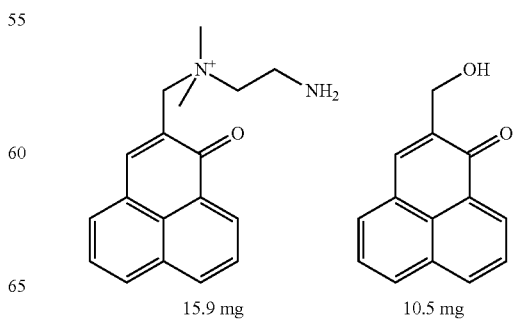

-continued

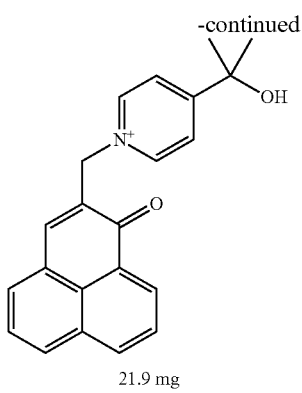

21.9 mg

Result: stiff, limited flexibility fibrous mat; intrinsic colour of colorant could not be discerned.

Variation c)

The respective photosensitizer (0.05 mmol) was dissolved in 70 mL of the basic resin (formulation II, III or IV). Of the hardener (formulation III), 30 mL was mixed in. The viscous, pale yellow solution was applied with a spray gun to degreased surfaces formed from i) PMMA or ii) roughened glass.

Alternatively, the mixture was applied to untreated wood several times in even coats with a brush, in order to obtain an antimicrobial seal. After hardening for 6 h at room temperature, post-hardening was carried out by heating to 40° C. for 3 h. The following examples were processed using this method:

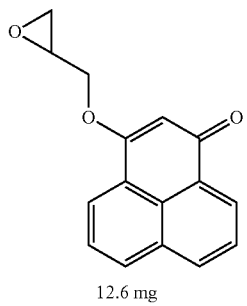 [SMILES: O=C1C=C(OCC2CO2)c2cccc3cccc1c23]

12.6 mg

Result: transparent, pale yellow, homogeneous coating; layer thickness between 20 and 40 µm, when brush used: >50 µm.

4) Room Temperature-Vulcanizing 1-Component (RTV-1) Silicone

Typical composition of the silicone (technical product from Wacker): polydimethylsiloxane diol and polydimethylsiloxane as a mixture with silicon dioxide (filler) and triacetoxymethylsilane (cross-linking agent, <5%)

Variation a)

Clear sanitary silicone (1-C, room temperature-crosslinking, acid-crosslinking, 5.0 g) was dissolved in hexane (10 mL). A solution of the respective photosensitizer (0.012 mmol) in dry dichloromethane (20 mL) was mixed in. The slightly opaque, pale yellow, viscous solution was evenly applied to i) a degreased glass plate, ii) a degreased PMMA plate, iii) a ceramic plate or iv) a polyester film. After approximately 15 min at room temperature, the coating had dried; approximately 10 min later, skin formation had commenced. After 6 h at room temperature, the approximately 0.1 mm thick layer had hardened all the way through.

Result: transparent, matte, pale yellow, homogeneous, rubber-like coating.

Variation b)

The respective photosensitizer (0.02 mmol) was dissolved in dry ethyl acetate (100 mL). Clear sanitary silicone (1-C, room temperature-crosslinking, acid-crosslinking, 8.0 g) was added and the solution was stirred until it was homogeneous. The slightly opaque, pale yellow solution was evenly applied to i) a clay plate, ii) a ceramic tile, iii) a degreased PE plate or iii) an aluminium plate, using a spray gun. After approximately 20 min at room temperature the coating had dried; approximately 10 min later, skin formation had commenced. After 6 h at room temperature the approximately 0.1 mm thick layer had hardened all the way through.

Result: transparent, matte, pale yellow, homogeneous, rubber-like coating.

Variation c)

The finely powdered photosensitizer (0.012 mmol) was stirred into clear sanitary silicone (1-C, room temperature-crosslinking, acid-crosslinking, 5.0 g) in a SpeedMixer™ DAC 600 (Hauschild Engineering, Germany) mixer at room temperature, until a macroscopically homogeneous paste was obtained. The pale yellow, viscous mass was evenly applied using a disposable syringe to i) a tile grout or ii) to bond two glass plates which were stacked vertically one on top of the other. After approximately 30 min at room temperature the silicone had dried; approximately 20 min later, skin formation had commenced. After 6 h at room temperature, the layer had hardened all the way through.

The following photosensitizers in the three variations were processed into pale yellow, rubber-like silicone grouts:

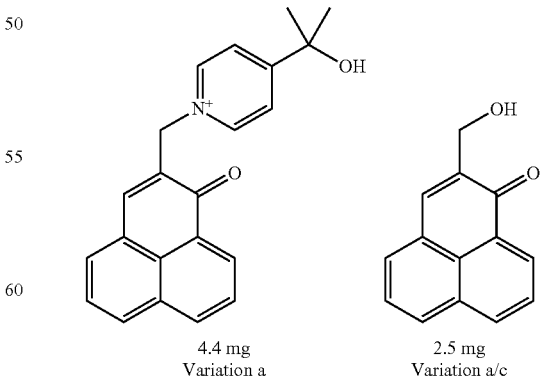

4.4 mg
Variation a 2.5 mg
Variation a/c

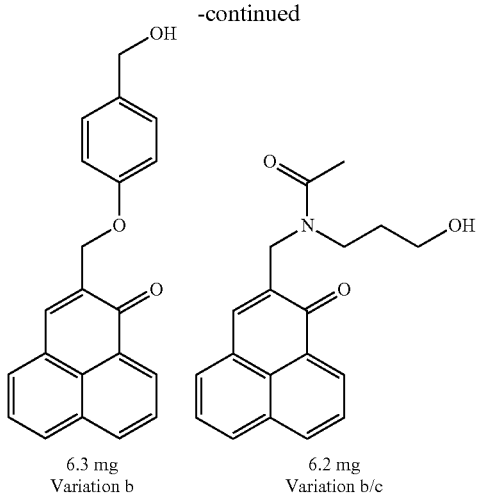
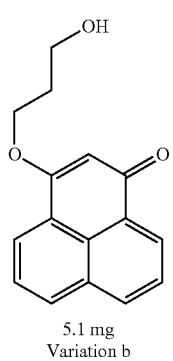

Result: transparent, matte, pale yellow, homogeneous, rubber-like grout.

5) Room Temperature-Vulcanizing 2-Component (RTV-2) Silicone

Typical composition of the silicone (technical product from Wacker): component A) oligomeric silane containing vinyl groups/vinylsilane and component B) polydimethylsiloxane as a mixture with silicon dioxide (filler) and adjuvants and platinum catalyst.

The base polymer (A) was mixed with the crosslinking agent (B) in a ratio of 9:1.

The finely powdered photosensitizer (0.05 mmol) was stirred into 90 g of the base polymer (A) at room temperature, until a macroscopically homogeneous paste was obtained. The pale yellow, viscous mass was mixed with the crosslinking agent (B) in a ratio of 9:1 with the aid of a flat spatula, evenly applied to i) a polyester film, ii) a ceramic tile, a degreased glass plate, iv) a degreased PE plate or v) an aluminium plate (50 mL per m²).

After approximately 30 min at room temperature, initial skin formation had occurred. After 8 h at room temperature the layer had hardened all the way through.

The following photosensitizers were processed into silicone coatings:

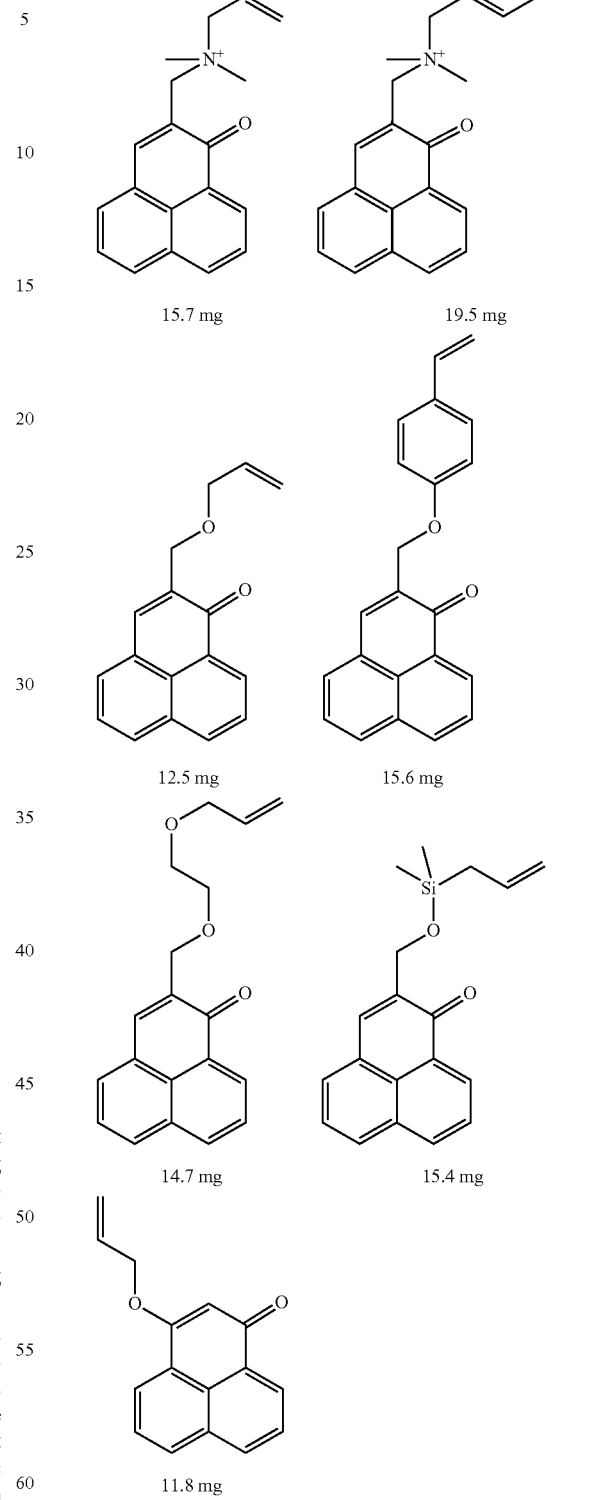

Result: transparent, matt, pale yellow, homogeneous, rubber-like coating.

6) Polyacrylate, 1-C

The finely powdered photosensitizer (0.05 mmol) was dissolved in 100 mL of methacrylic acid ethyl ester (dry conditions). Camphor quinone (1.7 mg, 0.01 mmol) and 4-dimethylaminobenzoic acid methyl ester (0.9 mg, 0.005 mmol, amine accelerator) were added and the mixture was stirred for 15 min in the dark. The solution could be kept for weeks in the dark.

The solution was applied to i) wood with a brush or ii) absorbed into a filter paper or iii) sprayed evenly onto a degreased PMMA plate.

In the second step, illumination was carried out using a polymerization lamp (LED Bluephase; IvoclarVivadent AG, at 650 mW/cm²) for 30 seconds. After production, the test specimens were stored in a drying cabinet at 37° C. for 24 h in order to complete the polymerization. The following photosensitizers were used in the experiments:

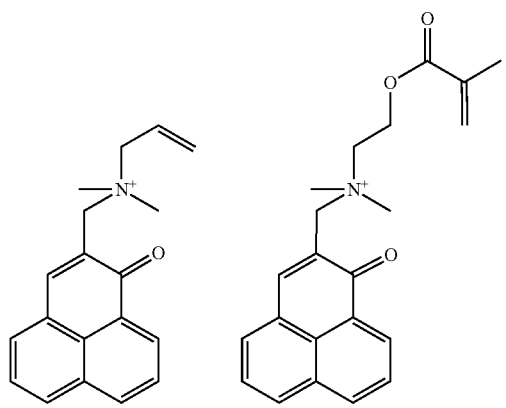

15.7 mg                19.3 mg

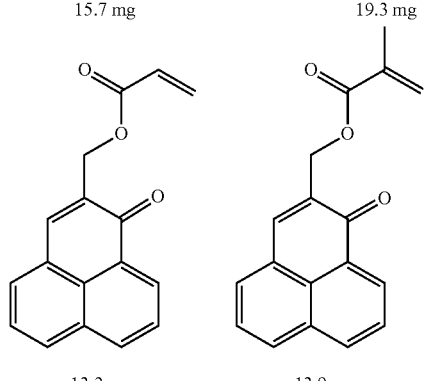

13.2 mg                13.9 mg

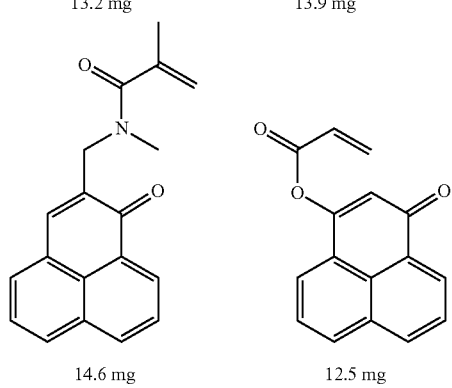

14.6 mg                12.5 mg

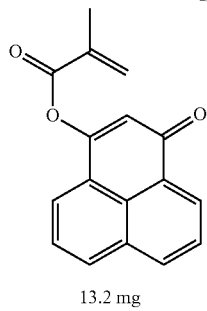

13.2 mg

Result: the following were obtained: i) transparent, polymeric seal, ii) a partially flexible, pale yellow platelet or iii) transparent, pale yellow, paint-like coating.

7) Polyacrylate, 2-C

Variation a)

The respective photosensitizer (0.05 mmol) was dissolved in 100 mL of methacrylic acid methyl ester (methyl methacrylate, MMA, Sigma Aldrich) (solution A). Tert-butyl peroxybenzoate (Peroxan PB, 0.5 g) was dissolved in THF (2 mL) (solution B). Solution B was added to solution A and the mixture was heated for 15 min at 90° C. in a water bath. The slightly viscous solution was i) applied to a degreased PMMA plate or ii) sprayed onto a degreased glass plate or iii) applied to pine wood and distributed evenly with a brush (50 mL per m²). To completely harden the acrylic glass coating, the support was stored for 24 hours at 60° C. in a drying cabinet. A pale yellow, clear synthetic material coating or polymeric seal for the wood was obtained.

Result: transparent, homogeneous, paint-like coating; in i) and ii), the yellow intrinsic colour of the layer was barely detectable, in iii), the intrinsic colour could not be distinguished from the background.

Variation b)

The respective photosensitizer (0.05 mmol) was dissolved in 100 mL of methacrylic acid methyl ester (methyl methacrylate, MMA, Sigma Aldrich) (solution A). Benzoyl peroxide (0.5 g) was dissolved in THF (2 mL) (solution B). Solution B was added to solution A and the mixture was heated for 20 min at 80° C. in a water bath. With the mixture, i) approximately 6 mm thick cotton fleece or ii) an approximately 6 mm thick felt mat or iii) a piece of aramid fabric (each 20×20 cm²) was impregnated evenly with a brush, so that the fabric could take up the mixture in its entirety.

In order to harden the acrylic glass completely, the fibrous mats were dried for 12 hours at 60° C. A solid yellowish plate was obtained. The following photosensitizers were processed:

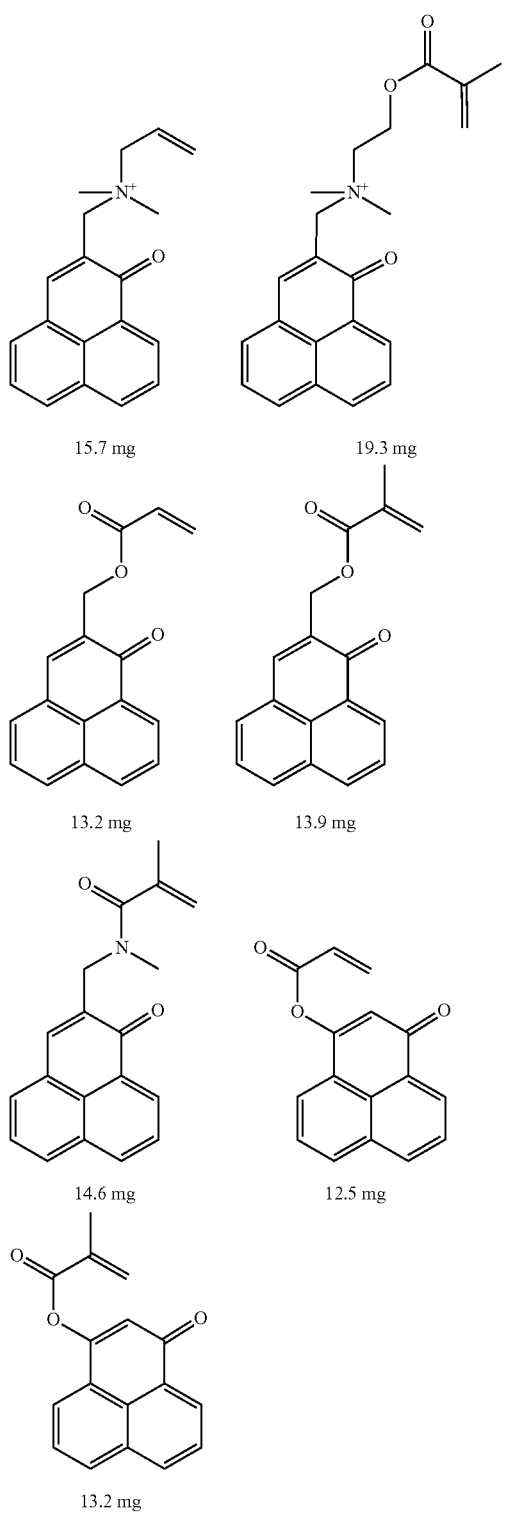

Result: stiff, limited flexibility fibrous mat; intrinsic colour of colorant could only just be discerned in i).

8) Polyacrylamide

A 40% solution of acrylamide/bis-acrylamide (37.5:1) in water (2.5 mL) was mixed with Tris buffer (3.75 mL, 1M, pH 8.8) and propylene glycol (0.6 mL). The respective photosensitizer (0.005 mmol) in distilled water (3.0 mL) was added. The solution was degassed for 5 minutes with a vacuum pump (5-10 mbar) and then TEMED was added (10 µL). Finally, 0.05 mL of ammonium persulphate (10% in water) was added, with stirring.

Next, i) a 3 mm thick cassette (plates previously cleaned with 70% alcohol) was filled with the mixture and carefully overlaid with isopropanol. After polymerization for 30 min at room temperature, the gel was solid and the supernatant could be poured away. After removing the chamber plates, a flexible, thick pale yellow film was obtained. Alternatively, ii) the mixture was evenly applied to a fleece.

During the polymerization, the material was covered with cling film. After polymerization for min at room temperature, the gel was solid and the film was carefully removed. A gel-like yellowish coating was obtained.

The following photosensitizers were polymerized in this manner:

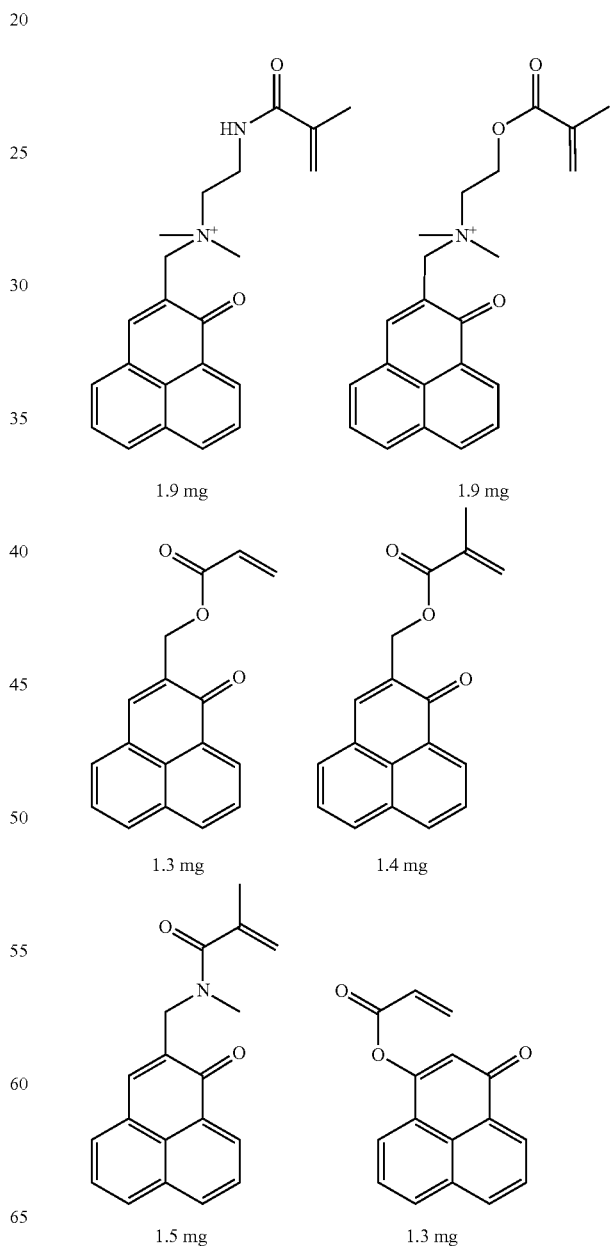

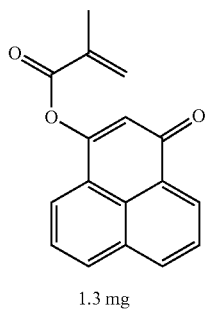

1.3 mg

Result: i) rubber-like, slightly opaque, pale yellow mat; ii) transparent, matt, pale yellow, homogeneous, rubber-like coating.

9) Cyanoacrylate

Variation a)

The respective photosensitizer (0.01 mmol) was dissolved in 100 mL of dichloromethane (dried over calcium chloride). 0.2 g of commercial cyanoacrylate (Loctite, Henkel AG & Co. KGaA, Düsseldorf, DE) was added to 1 g of the solution (dry conditions). The mixture was evenly sprayed onto a) a degreased glass plate or b) dry spruce wood. At room temperature and with a humidity of between 20% and 70%, the layer hardened completely within 20 min.

Variation b)

The respective photosensitizer (0.01 mmol) was dissolved in 100 mL of dry methylethylketone. Commercial cyanoacrylate (Loctite.) was mixed with 10 g of the solution in a ratio of 1:5 (w/w). The solution was evenly applied to a substrate cleaned with isopropanol, for example i) glass or ii) PE or iii) melamine plate. After evaporation of the solvent, the coating cured in the moisture of the air (approximately 15 min, humidity between 20% and 70%).

The following photosensitizers were processed in accordance with the respective variation:

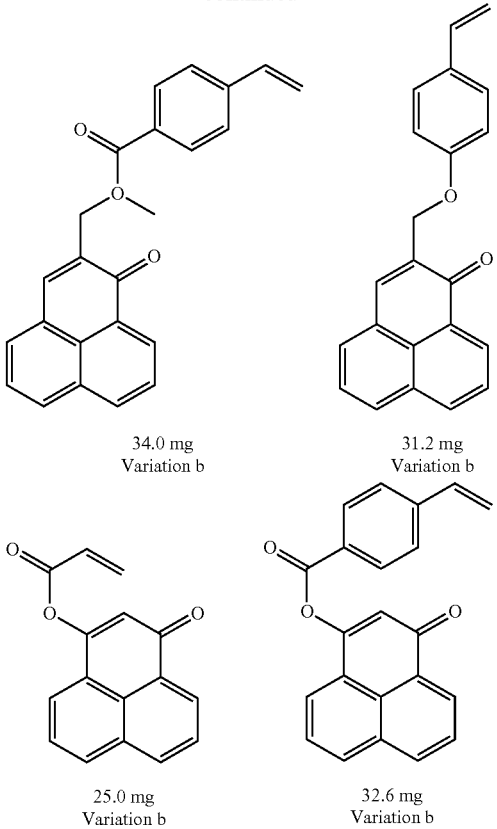

34.0 mg
Variation b 31.2 mg
Variation b 25.0 mg
Variation b 32.6 mg
Variation b

Result: transparent, slightly opaque, pale yellow, homogeneous coating; layer thickness between 20 and 40 μm.

10) Polystyrene

The respective photosensitizer (0.01 mmol) was dissolved in 20 mL of freshly distilled polystyrene (Sigma Aldrich) (solution A). Benzoyl peroxide (0.5 g) was dissolved in THF (2 mL) (solution B). Solution B was added to solution A and the mixture was heated for 20 min at 80° C. in a water bath. 5 to 6 mL of the mixture was painted evenly onto i) a clean, untreated chipboard or ii) a degreased PMMA plate or iii) a degreased glass plate (each 20×20 cm²) with a brush. The support was left for 12 hours at 60° C. in order to dry fully. A solid yellow plate was obtained. The following photosensitizers were processed:

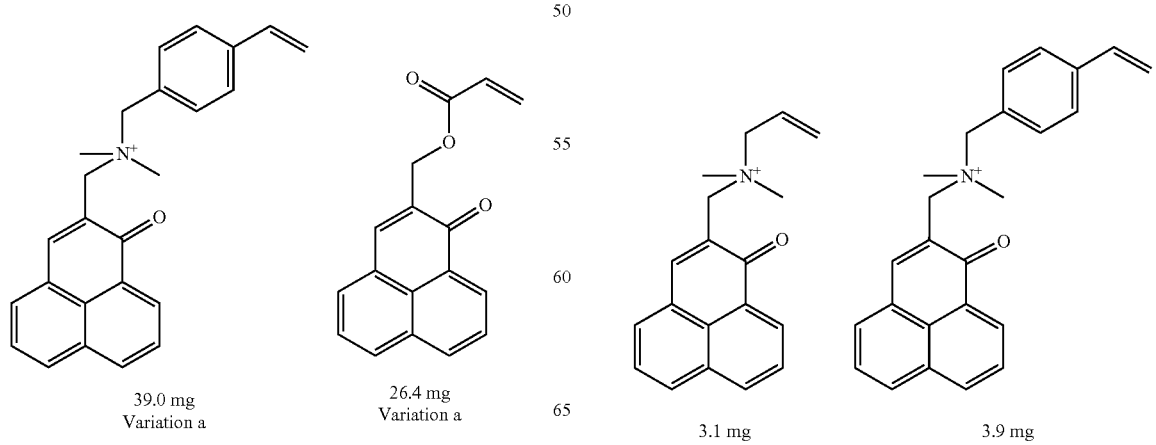

39.0 mg
Variation a 26.4 mg
Variation a 3.1 mg 3.9 mg

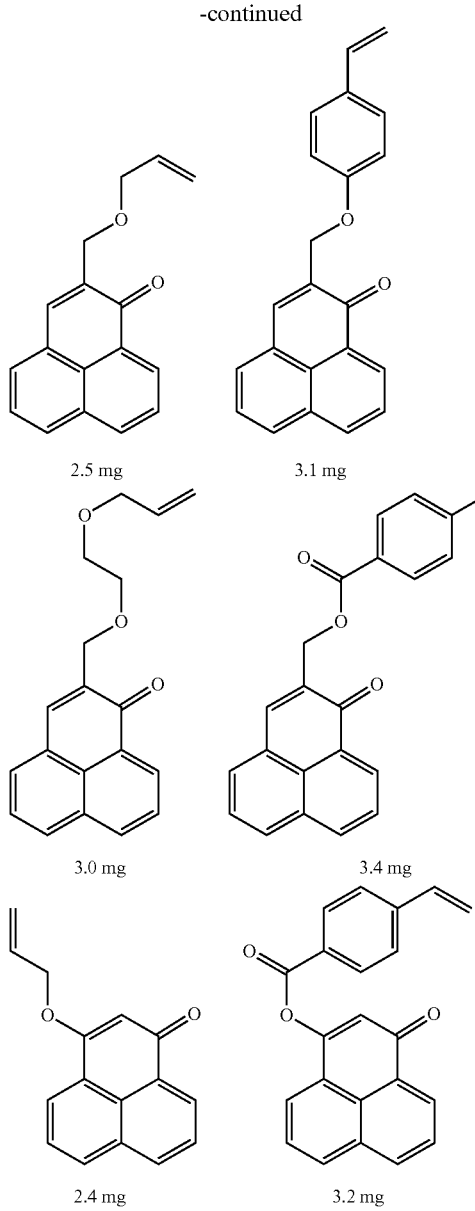

2.5 mg    3.1 mg 3.0 mg    3.4 mg 2.4 mg    3.2 mg

11) Carboxymethyl Cellulose Coatings

The respective photosensitizer (0.05 mmol) was dissolved in 100 mL of water along with finely crushed carboxymethyl cellulose (4.0 g, Akzo Nobel). 5 to 6 mL of the clear, somewhat viscous solution was painted evenly onto i) a clean, untreated chipboard or ii) a degreased PMMA plate (each 20×20 cm$^2$) using a brush.

Alternatively, iii) a cotton fleece (20×20 cm$^2$) could be evenly impregnated with a brush, so that the fabric could take up the mixture in its entirety. To harden, the support was left to dry for 3 hours at room temperature. The following photosensitizers were processed:

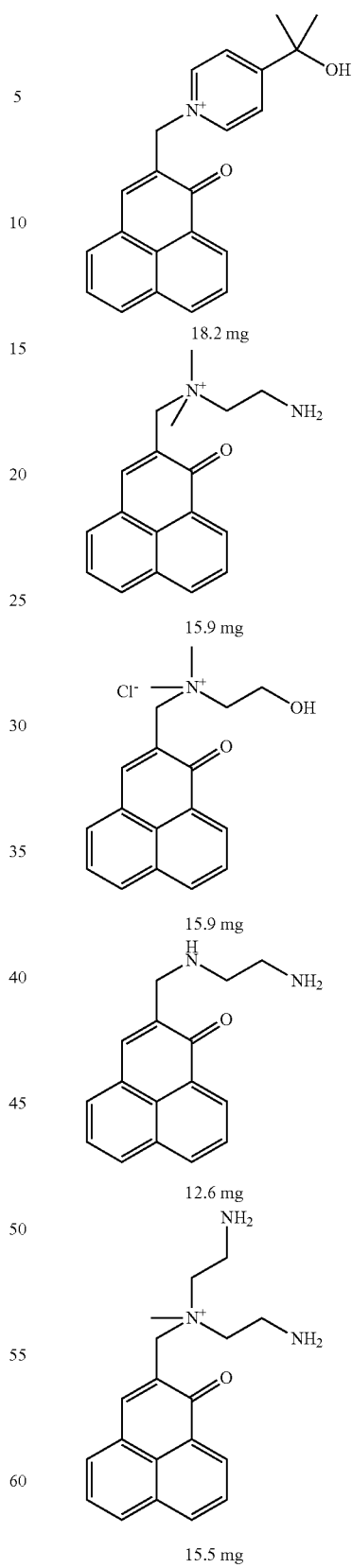

18.2 mg 15.9 mg 15.9 mg 12.6 mg 15.5 mg

Result: i) transparent, polymeric seal without any detectable intrinsic colour; ii) transparent, slightly opaque, pale yellow, homogeneous coating; iii) stiff, limited flexibility fibrous mat; the intrinsic colour of the photosensitizer was barely detectable.

12) Alginate Coatings

Sodium hydroxide (850 mg, 21.25 mmol) was dissolved in 95 mL distilled water. 5 g of alginic add (Sigma Aldrich) was added to the warm solution (approximately 35° C.) and stirred for 3 h. A viscous, clear solution was formed. A stock solution of the respective photosensitizer (5 mL, 12 mmol/L) was added dropwise, with stirring. Using the yellow, slightly viscous solution, i) a piece of paper or ii) a piece of cotton fleece or iii) a paper towel/pad (each 20×20 cm²) was impregnated. The surplus solution was allowed to drip out. The wet support was quickly immersed in a 1% calcium chloride solution. The material was allowed to drain well, it was then carefully swabbed and dried at room temperature in air for 3 hours.

The following photosensitizers were processed:

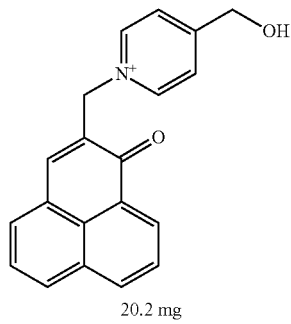

20.2 mg

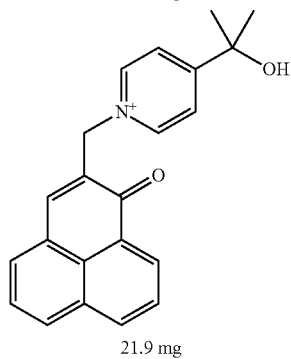

21.9 mg

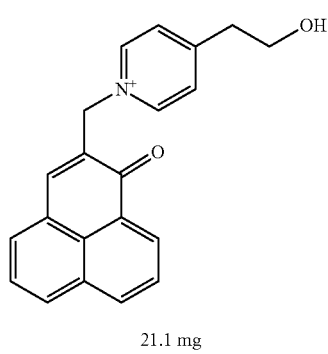

21.1 mg

-continued

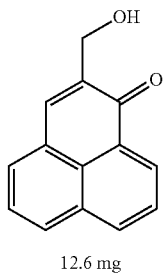

12.6 mg

Result: stiff, limited flexibility fibrous mat or piece of paper; the intrinsic colour of the photosensitizer was barely detectable.

Example 3: Testing the Activity of the Antimicrobial Surface Coatings

1.) Production of Sample Supports

The following photosensitizer was used for the tests below:

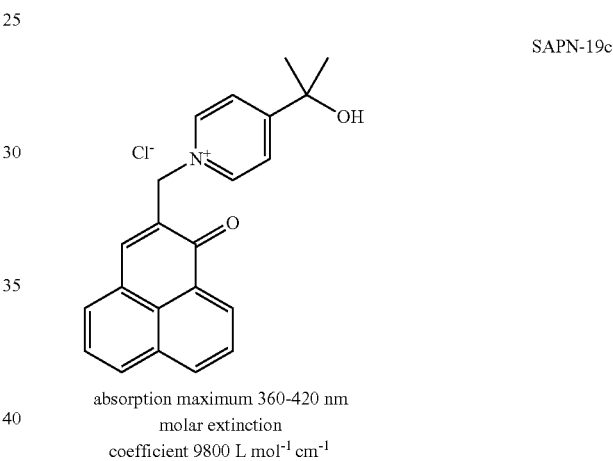

SAPN-19c absorption maximum 360-420 nm
molar extinction coefficient 9800 L mol$^{-1}$ cm$^{-1}$ The photosensitizer was dissolved in the respective paint system and applied to various square sample supports (width: 4 cm, length: 4 cm, thickness: 3 mm) formed from PVC or PMMA and then dried. After drying the coating, a specific quantity of bacteria from the species *Staphylococcus aureus* ATCC 25923 was applied to the surface.

In this regard, firstly, an overnight (ON) culture of *S. aureus* in 5 mL of Mueller Hinton broth (Carl Roth GmbH+Co. KG, Karlsruhe, DE) was inoculated with a single colony from an agar plate and incubated at 37° C. and 180 rpm on a shaker for 18-20 hours.

On the day of the test, in each case 1 mL of ON culture was centrifuged (Hettich Universal 320 R centrifuge (Andreas Hettich GmbH & Co. KG, Tuttlingen, DE); swing-out rotor 1494; 10 Min, 3000 rpm, RT). The supernatant was discarded and the pellet was re-suspended in 1 mL of Milli-Q water, which is commercially available from Merck (KGaA, Darmstadt, DE) (designation "Milli-Q Integral Ultra-pure Water (Type 1)").

After determining the optical density at 600 nm ("Specord 50 plus", spectrometer, Analytik Jena), the re-suspended bacteria were diluted with Milli-Q-water to a cell count of $10^5$ bacteria/mL. From the dilution, in each case 100 μL was dripped onto the sample support using a pipette (droplet size approximately 1 cm²).

This resulted in approximately 10.000 bacteria per cm² on the surface of the respective sample support. The sample support was then dried in air under a clean bench in the dark for approximately 2 hours, until water could no longer be seen on the surface.

2.) Irradiation and Quantitative Determination of the Colony Forming Units (CPU)/mL The respective sample supports were irradiated with monochrome light at a wavelength of 405 nm with the aid of a LED module (test area 5×5 cm homogeneously illuminated; high power LEDs) or with room lighting (Osram Lumilux Cool White, colour temperature 4000 K) at the intensities and for the irradiation periods given below. Directly after irradiation, the bacteria were wiped from the surface of the respective sample support with a sterile cloth and re-suspended in 1 mL of Mueller-Hinton broth.

Next, the sample was serially diluted (1:10 dilution stages: 180+20 μL; to dilution stage $10^5$).

For each dilution stage (100 to $10^{-5}$), 3× respectively 20 μL of broth was dripped onto a Mueller-Hinton agar plate (Carl Roth GmbH+Co. KG) using a pipette, and spread. The agar plates were then incubated at 37° C. ON.

On the following day, the colonies from all of the dilution stages which could be counted of an experiment were counted and the CFU/mL was calculated.

Dilution stages which exhibited a bacterial lawn or no colonies at all were denoted with "∞" or "0" and were not included in the calculation of the CFU/mL.

Next, from the value for the CFU/mL, the $\log_{10}$ eradication rate was calculated. The reference point in each experiment was the reference control (=100% count of bacteria employed).

A test was composed of the following:
coated sample support: without photosensitizer, not irradiated ("reference control")
coated sample support: with photosensitizer, not irradiated ("dark control")
coated sample support: without photosensitizer and irradiated ("light control")
coated sample support: with photosensitizer and irradiated ("sample")

3.) Paint Systems Used and Irradiation Parameters

3.1) 2-C Polyurethane Paint, Solvent Butyl Acetate/Xylene from Example 2.1

Coated material: PMMA, 3 mm thickness, 4×4 cm
Drying time approximately 1 hour
Drying temperature 15-30° C.
Application with a spray gun
Concentration of photosensitizer used: 200 μm (61.55 mg/L)
Irradiation Conditions:

| Test No. | Irradiation source | Irradiation intensity | Irradiation duration |
|---|---|---|---|
| 3.1.1 | LED module (405 nm) | 10 mW/cm² | 2 min |
| 3.1.2 | LED module (405 nm) | 20 mW/cm² | 2 min |
| 3.1.3 | LED-module (405 nm) | 0.7 mW/cm² | 0 to 150 min |

3.2.) 1-C Polyurethane Paint, Water-Based, from Example 2.2

Coated material: PVC, 3 mm thickness, 4×4 cm
Drying time approximately 2 hours
Drying temperature 15-30° C.
Relative humidity for the drying time 30-70%
Application with a spray gun
Concentration of photosensitizer used: 200 μm (61.55 mg/L)
Irradiation Conditions:

| Test No. | Irradiation source | Irradiation intensity | Irradiation duration |
|---|---|---|---|
| 3.2.1 | LED module (405 nm) | 10 mW/cm² | 10 min |

3.3) Room Temperature-Vulcanizing 2-Component (RTV-2) Silicone from Example 2.5

Coated material: PVC, 3 mm thickness, 4×4 cm
Drying time approximately 2 hours
Drying temperature 15-30° C.
Relative humidity for the drying time 30-70%
Application with a spray gun
Concentration of photosensitizer used: 200 μm (61.55 mg/L)
Two grades of silicone hardness (known as "Shores"): A=10 Shore; B=45 Shore
Irradiation Conditions:

| Test No. | Irradiation source | Irradiation intensity | Irradiation duration |
|---|---|---|---|
| 3.3.1 | LED module (405 nm) | 10 mW/cm² | 5 min |
| 3.3.2 | LED module (405 nm) | 10 mW/cm² | 10 min |

4.) Results and Evaluation

4.1) 2-C Polyurethane Paint (Solvent: Butyl Acetate/Xylene) from Example 2.1

In a first study with the 2-C paint system, firstly, high intensities of 10 and 20 mW/cm² were used in order to test the activity of the photosensitizer SAPN-19c used against *S. aureus*. The results are shown in FIG. 1A.

FIG. 1A respectively shows the mean values for the reduction of *S. aureus* on the 2-C paint surface from three independent tests. The irradiation was carried out using 10 or 20 mW/cm² and for 2 minutes (corresponds to an energy density of 1.2 or 2.4 J/cm²).

FIG. 2A shows that the 2-C paint system, even after a irradiation time of 2 minutes at a light intensity of 10 mW/cm², there was a $\log_{10}$ reduction of 1.8 (mean value of 3 independent experiments). Increasing the light intensity to 20 mW/cm² led to an effective extermination of 2.7 $\log_{10}$ units.

Subsequently, the effectivity at low intensities of 0.7 mW/cm² was determined. The results are shown in FIG. 1B.

Figure 1B:
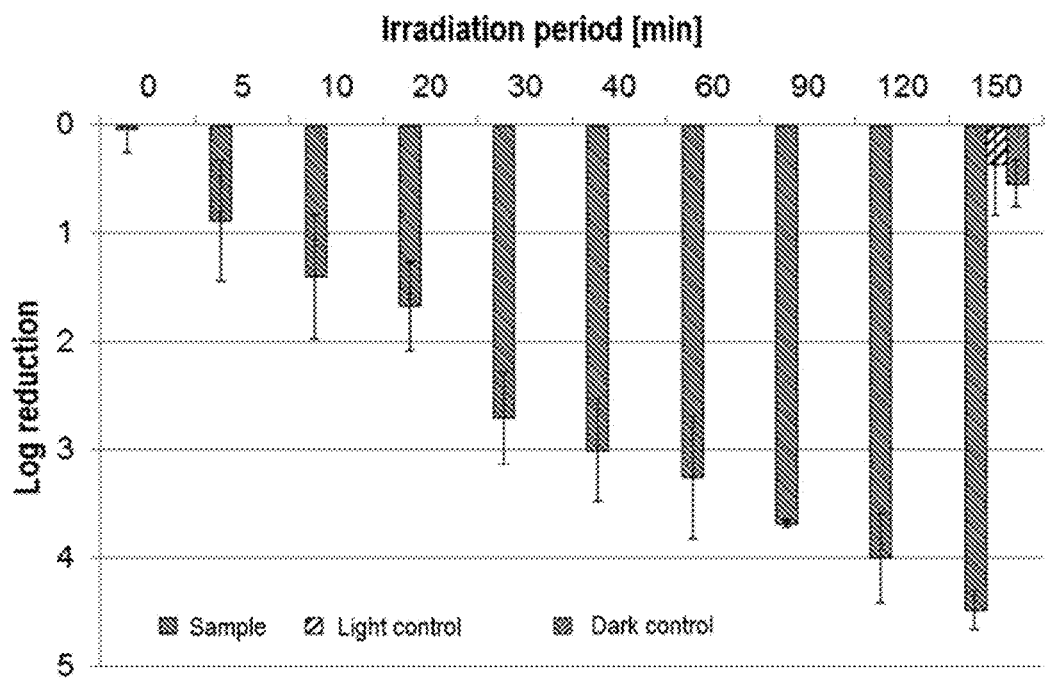
FIG. 1B shows the results of the log reduction of the *S. aureus* count in Example 3.2.

FIG. 1B respectively shows the mean values for the reduction of *S. aureus* on the 2-C paint surface (colourless solvent-based 2-C paint on transparent PMMA sample support) from two independent tests.

The irradiation was carried out using 0.7 mW/cm$^2$ for up to 150 minutes (corresponds to an energy density of up to 6.3 J/cm$^2$). The mean value for the reference control (no light, no catalyst) was 3.2×10$^4$ bacteria per mL. The light and dark controls were only measured at 150 minutes.

The reduction in the colony forming units with respect to a non-irradiated sample (0 min) was measured at intervals, wherein after the times shown in FIG. 1b (5 min, 10 min, 20 min, 30 min, 40 min, 60 min, 90 min, 120 min and 150 min), respectively 2 coated sample supports were taken out of the irradiation. The results from two independent tests are shown in FIG. 1B.

The mean value for the reference control (no light, no catalyst) was 3.2×10$^4$ bacteria per mL. The light and dark controls were only measured at 150 minutes.

FIG. 1B shows that after just 20 minutes, the 2-C paint system reached an eradication of S. aureus of 1.9 log$_{10}$ units.

When irradiated with an artificial light source, the 2-C paint system exhibited a biological activity against S. aureus, both at high intensities and low irradiation times (FIG. 1A), and also at low intensities and longer irradiation times (FIG. 1B).

4.2.) 1-C Polyurethane Paint, Water-Based, from Example 2.2

A first test with a high intensify (10 mW/cm$^2$) and a long irradiation period (10 minutes) demonstrated the activity of the 1-C paint system.

Figure 2:
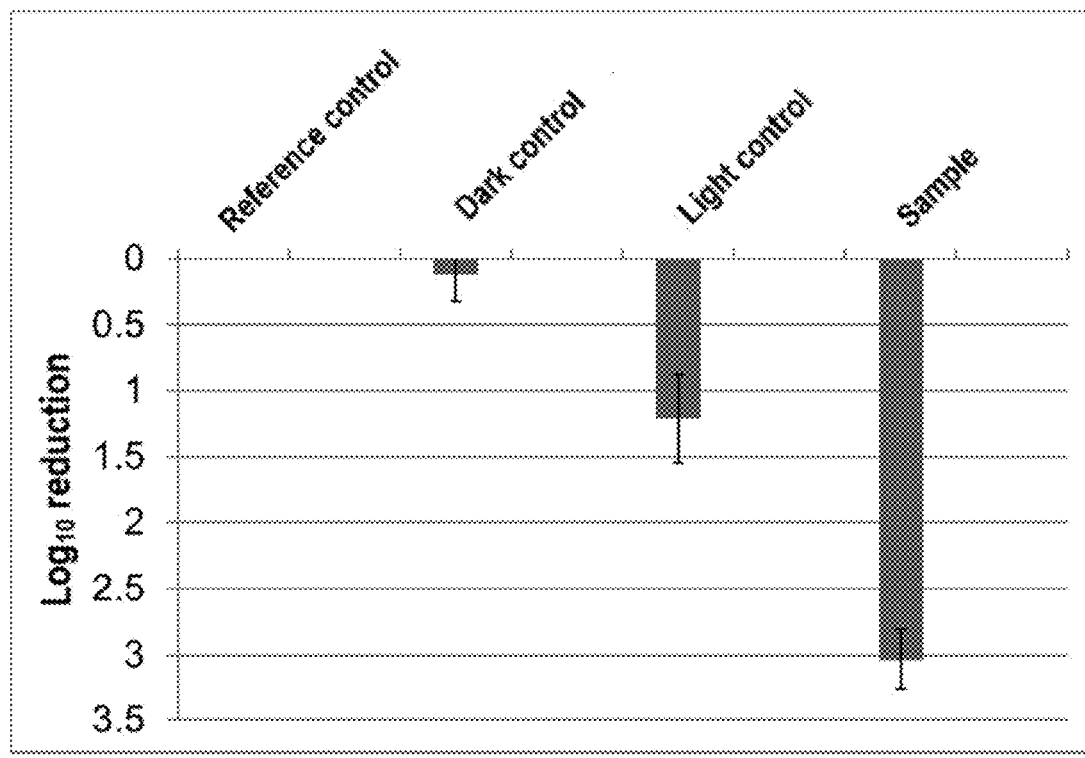
FIG. 2 shows the results of the log reduction of the *S. aureus* count in Example 3.3.

The results are shown in FIG. 2.

FIG. 2 shows the mean values for the reduction of S. aureus on the 1-C paint surface from three independent tests. The irradiation was carried out using 10 mW/cm$^2$ and 10 minutes (corresponds to an energy density of 6 J/cm$^2$).

The experiments with the 1-C paint system clearly show that only an interaction of light and the photodynamic catalyst brings about an effective eradication of S. aureus on the coated surface. Three independent tests exhibited a mean eradication of 3.0 log$_{10}$ units for an energy density of 6 J/cm$^2$.

The light control in the experiments exhibited a mean reduction of 1.2 log$_{10}$ units, which presumably is due to the dark sample support.

3.3) Room Temperature-Vulcanizing 2-Component (RTV-2) Silicone from Example 2.5

A first test with a high intensify (10 mW/cm$^2$) and an irradiation period of 5 minutes or 10 minutes demonstrated the activity of the RTV-2 silicone system.

Figure 3:
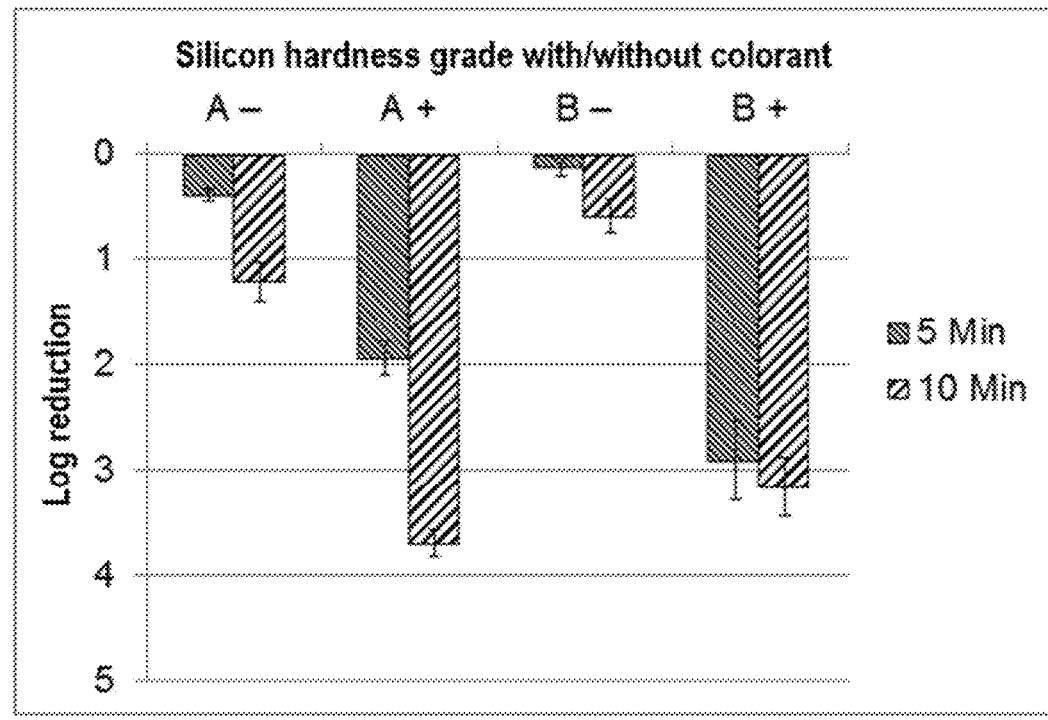
FIG. 3 shows the log reduction of *S. aureus* on the silicone surface (A− signifies 10 Shore without colorant, A+ signifies 10 Shore plus colorant, B− signifies 45 Shore without colorant, B+ signifies 45 Shore plus colorant).

The results are shown in FIG. 3, wherein in each case the mean value of 3 tests is shown.

FIG. 3 shows the log reduction of S. aureus on the silicone surface (A− signifies 10 Shore without colorant, A+ signifies 10 Shore plus colorant, B− signifies 45 Shore without colorant, B+ signifies 45 Shore plus colorant).

4.3) Summary

In the paint systems tested (2-C PUR paint system; 1-C PUR paint system, RTV-2 silicone), the photosensitizer SAPN-19c which was used exhibited a biological activity against S. aureus on the painted surface coating.

Higher light intensities and/or longer irradiation periods produced more singlet oxygen, which resulted in a faster and more effective eradication of microorganisms on the surface.

The concentration of 200 μM (61.55 mg/L) used in both paint systems was not visible on coloured surfaces. Furthermore, at a light intensity of 6 J/cm$^2$, the coating achieved a reduction of 3 log$_{10}$ units (=99.9%) of the bacteria involved.

Example 4. Testing the Phototoxic Effect of a Coated Surface in Office Lighting (Neon Tubes)

In a subsequent test, the 2-C paint system was irradiated with room lighting. In this regard, the photoactive surfaces produced in Example 2.1 with the photosensitizers SAPN-19c and SAPN-19 were additionally stored exposed in areas with normal office lighting (standard fluorescent lights, Osram Cool White, 840) and the phototoxic action on S. aureus with the same pathogen counts as in Example 3 was analysed after specific periods. In this regard, the photoactive layers were distanced from the light source by approximately 40 cm. It was shown that for the photosensitizer SAPN-19c, after storage for 24 h under standard office lighting conditions with an illumination period of 12 h, that ail pathogens on the surface had been completely eradicated (approximately 5.5 log$_{10}$ units, corresponding to >99.999% reduction).

Example 5: Long-Term Test of Photoactive Stability

In order to test the stability of the lacks produced, a long term test was carried out.

The test surfaces were pre-irradiated for different time periods (5, 25, 50, 75 h) at an output of 5 mW cm$^{-2}$ in order to establish whether the respective photosensitizer in PUR was affected in a manner such that the phototoxic activity of the surface was reduced:

| Applied energy [J cm$^{-2}$] | 5 mW cm$^{-2}$ | 0.7 mW cm$^{-2}$ | "Irradiation days" |
|---|---|---|---|
| 90 | 5 h | 35.70 h | 7 days (d) |
| 450 | 25 h | 178.5 h | 36 d |
| 900 | 50 h | 357.0 h | 71 d |
| 1350 | 75 h | 535.5 h | 107 d |

Following the pre-irradiation, the surfaces as described above were contaminated with S. aureus then irradiated for 2 h (corresponds to 5 mW cm$^{-2}$) and the phototoxic efficiency was measured.

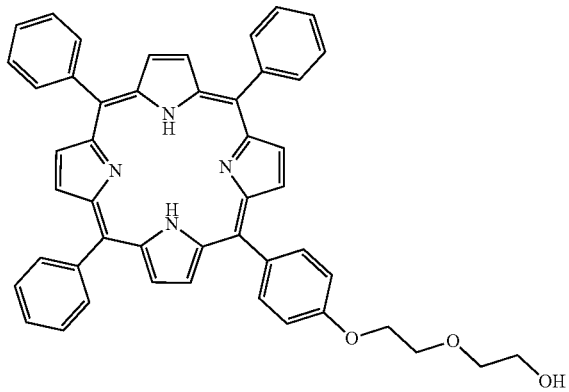

Molecular Weight = 718.86
Molecular Formula = C48H38N4O3

TPP sensitizer WBII/2
Quantity used: 5 10$^{-4}$ mol/L

-continued

SAPN-19c

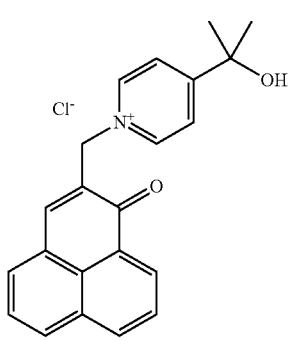

Quantity used: 5 10⁻⁴ mol/L

The TPP sensitizer WBII/2 was produced using the method described in Felgenträger A., Maisch T., Späth A., Schroder J. A., Bäumler W., "Singlet oxygen generation in porphyrin-doped polymeric surface coating enables antimicrobial effects on *Staphylococcus aureus*.", (Phys Chem Chem Phys. 2014 Oct. 14; 16(38):20598-607. doi: 10.1039/c4cp02439g.).

For the porphyrin-doped surfaces tested (TPP sensitizer WBII/2), there was a noticeable reduction in the phototoxic efficiency. In this regard, after one month, the test surfaces had discoloured significantly and they lost phototoxic activity.

This may be because the ring of the colorant breaks under the influence of the active oxygen, whereupon bilirubin analogues are formed:

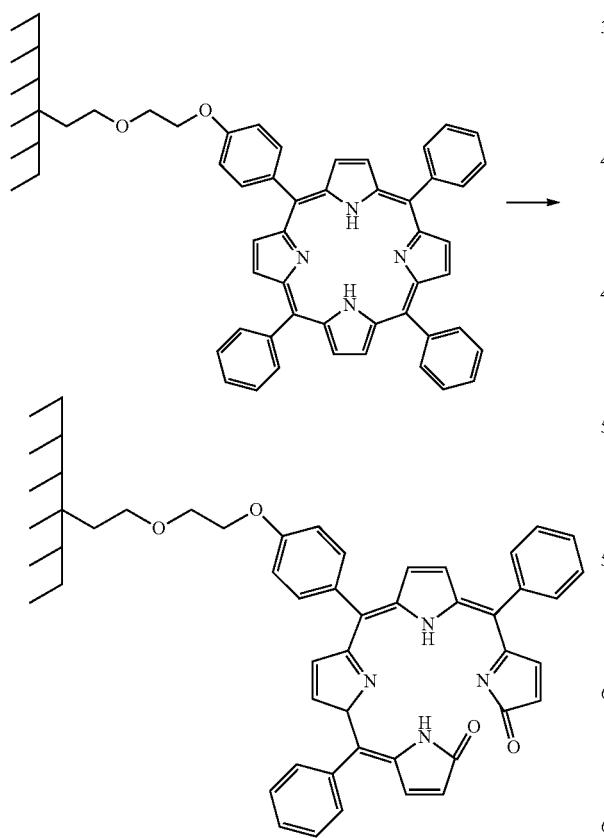

For SAPN-19c, there was no difference as regards phototoxic efficiency up to a pre-irradiation of 75 h with 5 mW cm⁻².

This corresponds to an extrapolated 312 days of irradiation (d), assuming that office lighting tubes with a power of 100 μW cm⁻² (at the office workspace) are continuously illuminated for 12 hours per day.

What is claimed is:

1. A phenalen-1-one compound with the general formula (1a):

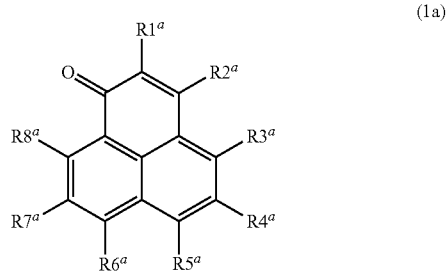

(1a)

wherein the residues $R1^a$ to $R8^a$, which respectively independently of one another may be identical to or different from each other, respectively represent hydrogen, halogen, alkyl containing 1 to 12 C atoms, alkylaryl containing 5 to 20 C atoms, aryl containing 5 to 20 C atoms, *—O-alkyl containing 1 to 12 C atoms, *—O-alkylaryl containing 5 to 20 C atoms, *—O-aryl containing 5 to 20 C atoms, ether containing 2 to 12 C atoms, a residue with the formula *—O—C(=O)—R$^{(Ia)}$, a residue with the formula *—C(=O)—R$^{(Ib)}$, or an organic residue W1a which contains at least one reactive functional group, with the proviso that at least one of the residues $R1^a$ or $R2^a$ is an organic residue W1a, wherein the organic residue W1a respectively independently of each other represents a residue with the general formula (2a) to (6a):

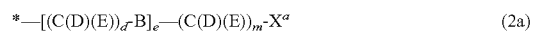 (2a)

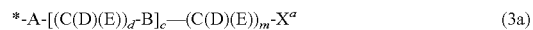 (3a)

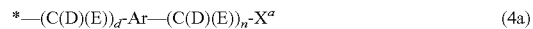 (4a)

 (5a)

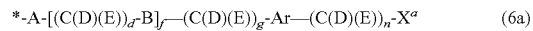 (6a)

wherein the residue A respectively independently of each other represents sulphur or a residue with the general formula (10a) to (11a):

 (10a)

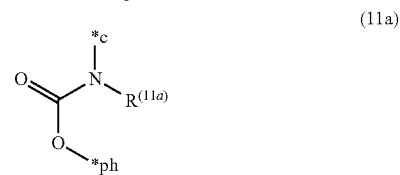 (11a)

wherein *$^{ph}$ respectively denotes a linkage from the residue with the general formula (10a) to (11a) to a C atom of the phenalene ring and *$^c$ respectively denotes a linkage from the residue with the general formula (10a) to (11 a) to a C atom of the residue (C(D)(E)), wherein the residue B respectively independently of each other represents oxygen, sulphur or a residue with the general formula (10) to (12):

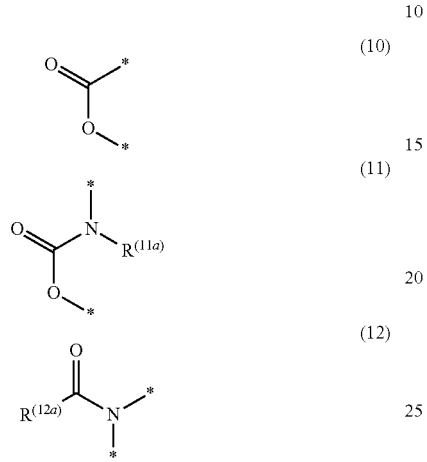

and wherein the residues R$^{(Ia)}$, R$^{(Ib)}$, R$^{(11a)}$ and R$^{(12a)}$ respectively independently of each other represent methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, and wherein the residues D and E respectively independently of each other represent hydrogen, halogen, hydroxyl, alkyl which may be linear or branched, containing 1 to 5 carbon atoms, hydroxyalkyl which may be linear or branched, containing 1 to 5 carbon atoms and 1 to 5 OH groups, phenyl, benzyl, a residue with the formula *-L-R$^{(II)}$, a residue with the formula *-L-C(=L)-R$^{(III)}$, a residue with the formula *—(CH$_2$)$_q$—X$^a$, a residue with the formula *-L-(CH$_2$)$_q$—X$^a$, or a residue with the formula *—(CH$_2$)$_s$-L-(CH$_2$)$_t$—X$^a$, wherein the residue L respectively independently of each other represents oxygen or sulphur, wherein the residues R$^{(II)}$ and R$^{(III)}$ respectively independently of each other, represent hydrogen, methyl, ethyl, n-propyl, iso-propyl, n-butyl, sec-butyl, iso-butyl, n-pentyl, phenyl or benzyl, and wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, the indices q, s and t respectively independently of each other representing a whole number from 1 to 5, wherein the indices c, g, f and n respectively independently of each other represent a whole number from 0 to 5, and wherein the indices b, d, e and m respectively independently of each other represent a whole number from 1 to 5, wherein the residue Ar respectively independently of each other represents a substituted or unsubstituted aromatic residue or a substituted or unsubstituted heteroaromatic residue which contains no N atoms, and wherein the residue X$^a$ respectively independently of each other represents a reactive functional group *—OH, *—SH, *—NCO, *—NCS, *—Si(R$^{(VIII)}$)(R$^{(IX)}$)—[O—Si(R$^{(X)}$)(R$^{(XI)}$)]$_p$—Z, or a residue with the general formula (20) to (24):

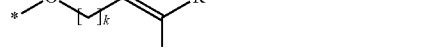

wherein the residues R$^{(20a)}$, R$^{(20b)}$, R$^{(20c)}$, R$^{(21a)}$, R$^{(22a)}$, R$^{(22b)}$, R$^{(22c)}$, R$^{(23a)}$, R$^{(24a)}$, R$^{(24b)}$, and R$^{(24c)}$ respectively independently of each other, represent hydrogen, methyl, ethyl, n-propyl, iso-propyl, n-butyl, sec-butyl, iso-butyl, or n-pentyl, and wherein the indices l and k respectively independently of each other represent a whole number from 0 to 4, wherein the residues R$^{(VIII)}$, R$^{(IX)}$, R$^{(X)}$ and R$^{(XI)}$ respectively independently of each other represent hydrogen, alkyl which may be linear or branched, containing 1 to 5 carbon atoms, —O-alkyl which may be linear or branched, containing 1 to 5 carbon atoms, phenyl or benzyl, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof, wherein the residue Z respectively independently of each other represents halogen, hydroxyl, alkoxyl containing 1 to 4 carbon atoms or alkylcarboxyl containing 1 to 4 carbon atoms, and wherein the index p respectively independently of each other represents a whole number from 0 to 4.

2. The phenalen-1-one compound as claimed in claim 1, wherein the residue Ar respectively independently of each other represents an unsubstituted or substituted phenyl residue, an unsubstituted or substituted biphenyl residue, an unsubstituted or substituted diphenylpropyl residue or an unsubstituted or substituted bisphenylsulphonyl residue.

3. The phenalen-1-one compound as claimed in claim 2, wherein the residue Ar respectively independently of each other represents a residue with the general formula (25a) to (25c), (29a) to (29c), (30) or (31):

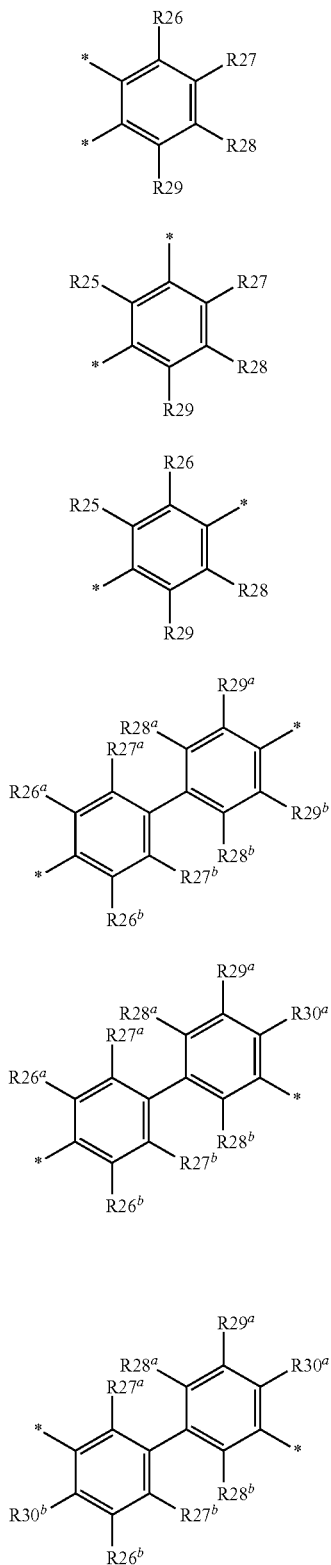

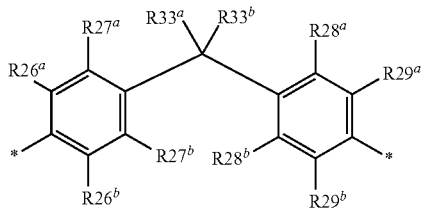

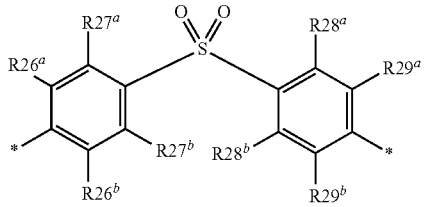

wherein the residues R25, R26, R27, R28, R29, $R26^a$, $R26^b$, $R27^a$, $R27^b$, $R28^a$, $R28^b$, $R29^a$, $R29^b$, $R30^a$ and $R30^b$ respectively independently of each other represent hydrogen, hydroxy, alkyl which may be linear or branched, containing 1 to 5 carbon atoms, perfluoralkyl which may be linear or branched, containing 1 to 5 carbon atoms, *—O-alkyl which may be linear or branched, containing 1 to 5 carbon atoms, phenyl or benzyl, and wherein the residues $R33^a$ and $R33^b$ respectively independently of each other represent hydrogen, hydroxy, alkyl which may be linear or branched, containing 1 to 5 carbon atoms, perfluoralkyl which may be linear or branched, containing 1 to 5 carbon atoms, *—O-alkyl which may be linear or branched, containing 1 to 5 carbon atoms, phenyl, benzyl or, when taken together, a cycloalkyl which may be linear or branched, containing 4 to 9 carbon atoms, or a 9H-fluoren-9-ylidene residue, wherein phenyl and benzyl respectively independently of each other may be unsubstituted or substituted with one or more residues selected from the group consisting of chlorine, bromine, fluorine, methyl, ethyl, n-propyl, iso-propyl, methoxy, ethoxy, and combinations thereof.

4. The phenalen-1-one compound as claimed in claim 1, wherein the at least one organic residue W1a respectively independently of each other represents a residue with the general formula (43) to (52), (54), (56), (58) to (67) or (98a) to (98e):

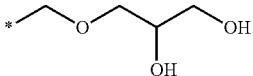

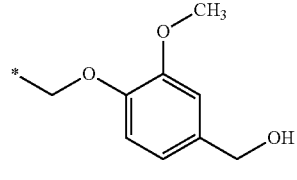

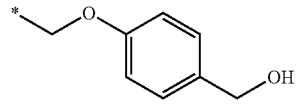

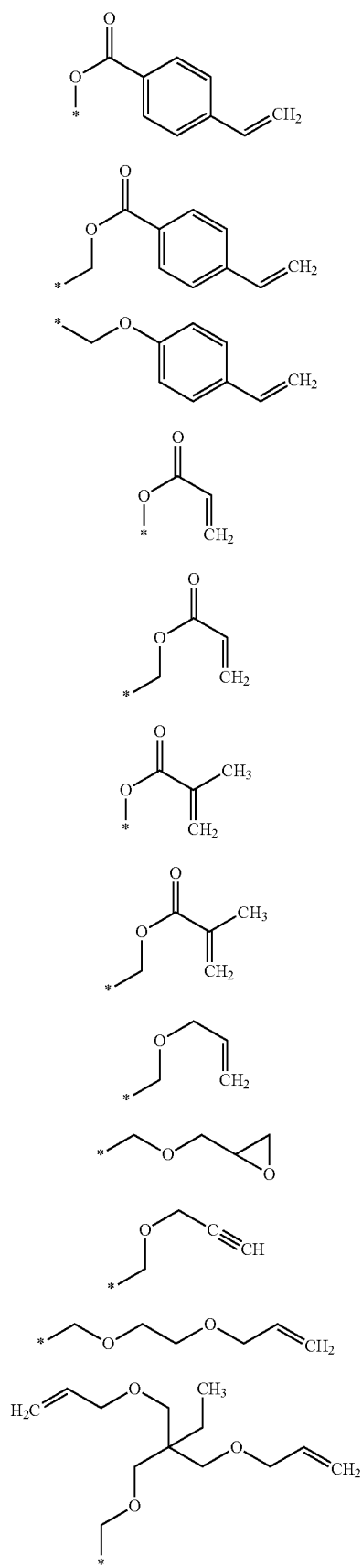
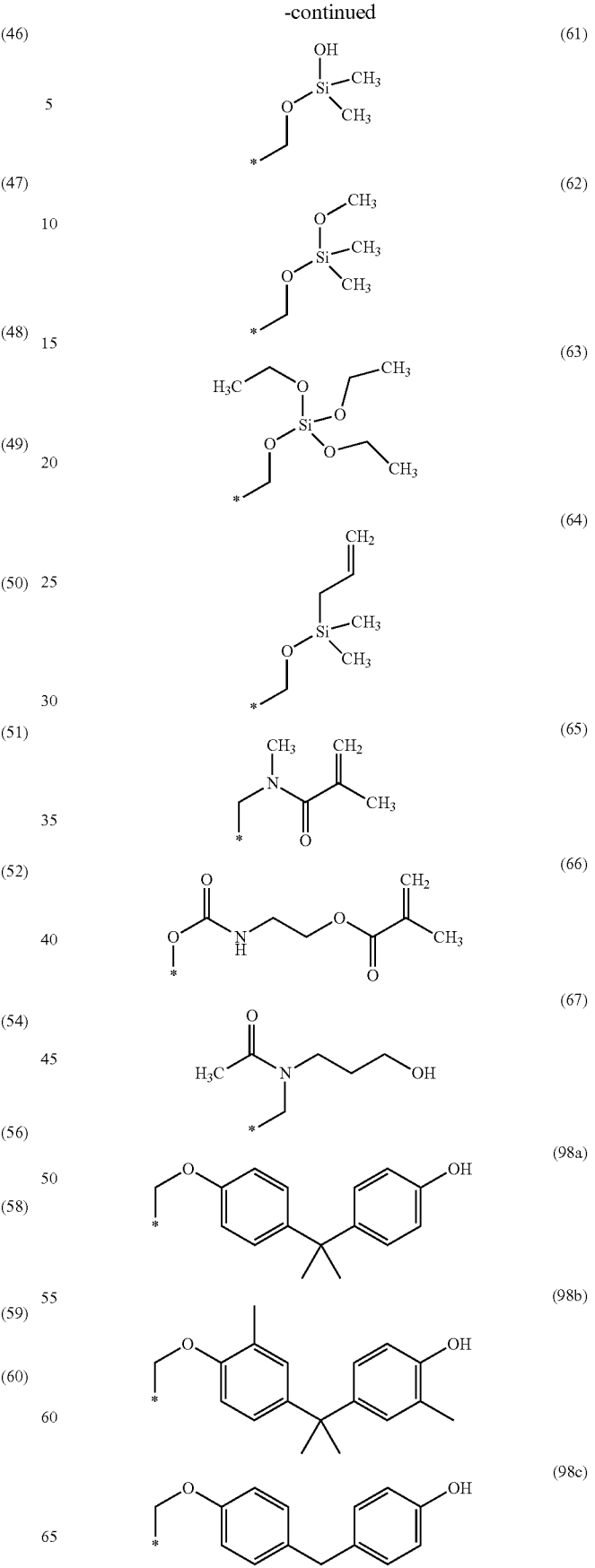

(98d) 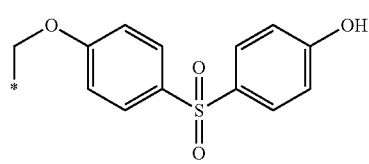
(98e) 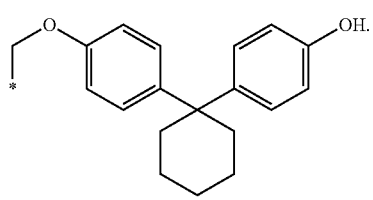
5. The phenalen-1-one compound as claimed in claim 1, wherein the at least one phenalen-1-one compound with the general formula (1a) is selected from the group which consists of compounds with formula (103) to (112), (114), (116), (118) to (127), (162) to (166) and combinations thereof:
(103) 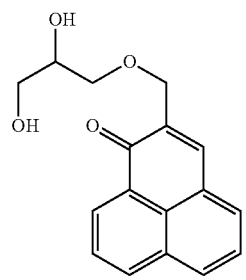
(104) 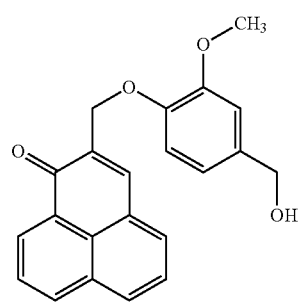
(105) 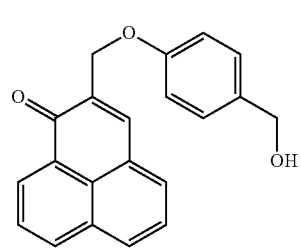
(106) 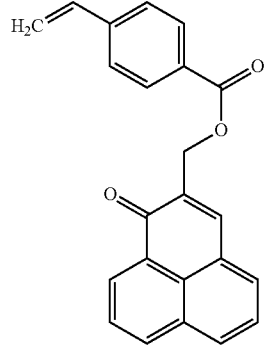
(107) 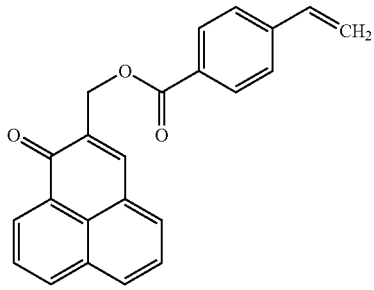
(108) 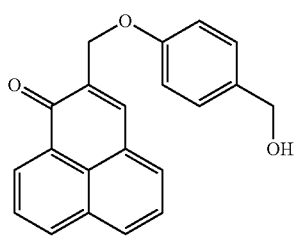
(109) 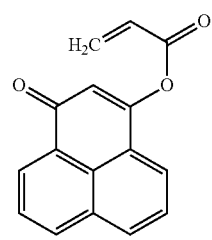
(110) 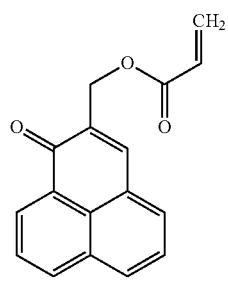

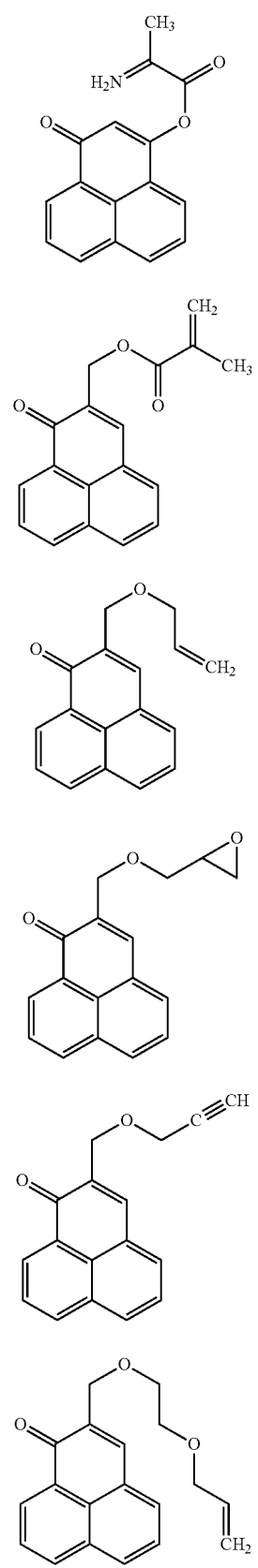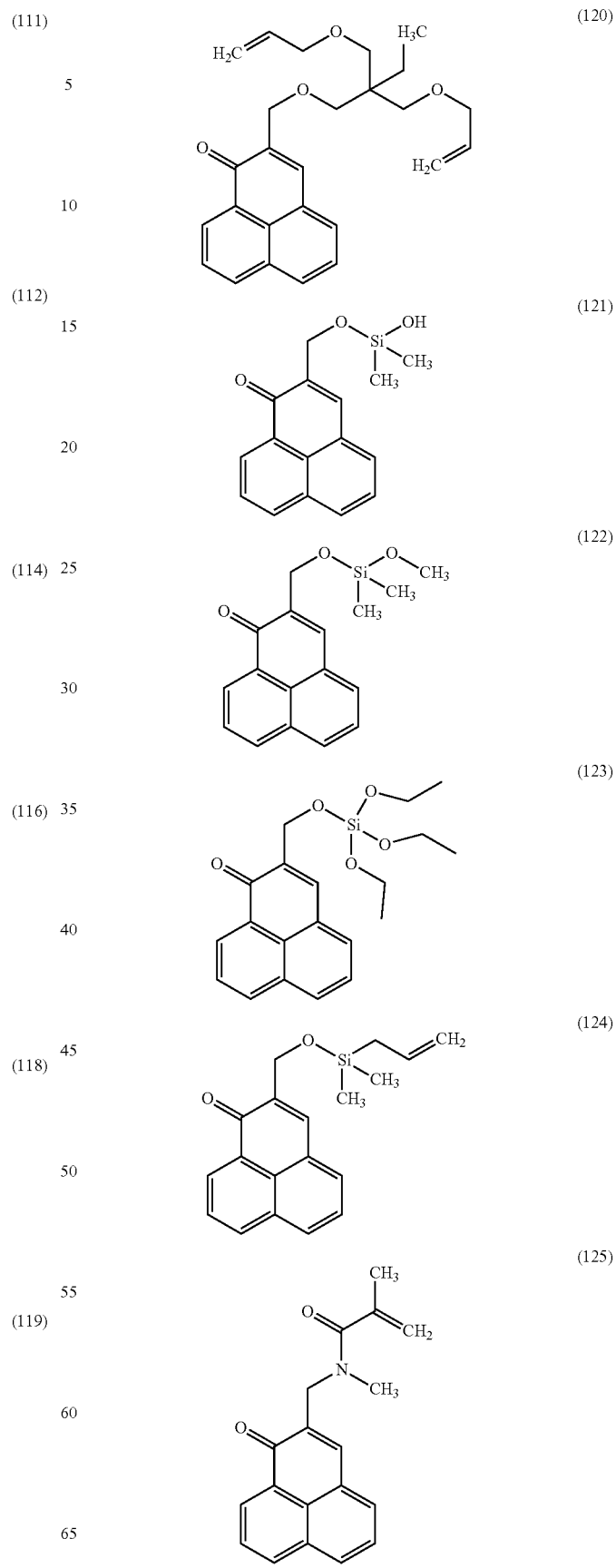

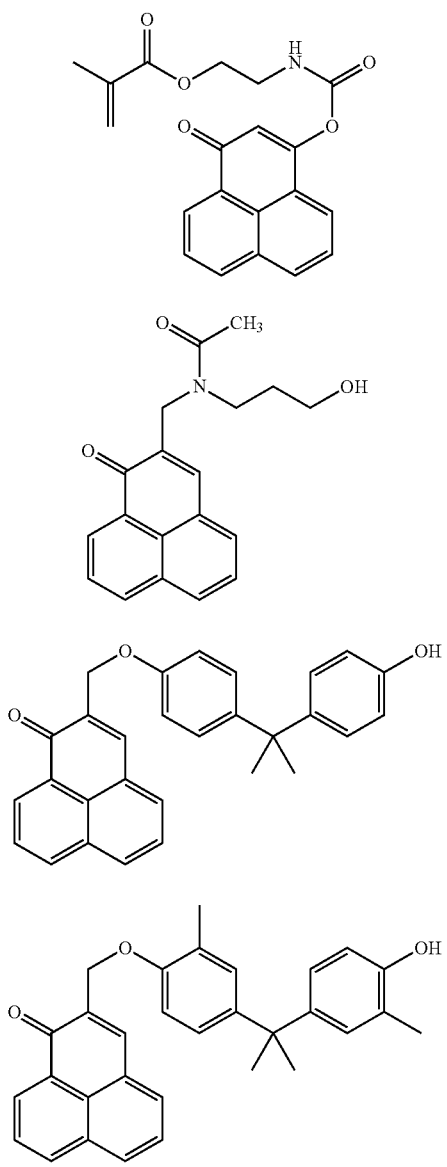
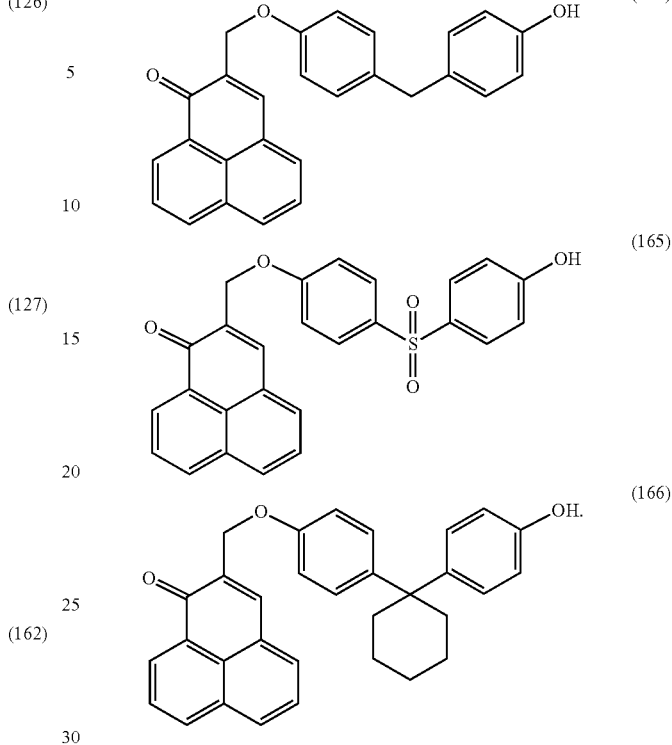

6. A method for inactivation of microorganisms selected from the group consisting of viruses, archaea, bacteria, bacterial spores, biofilms of bacteria, fungi, fungal spores, protozoa, algae and blood-borne parasites, and/or a biofilm thereof, said method comprising contacting at least one member of said group with a phenalen-1-one compound as claimed in claim 1.

7. A method for photodynamic surface cleaning and/or surface coating of an article or area by contacting said article or said area with a phenalen-1-one compound as claimed in claim 1 in order to inactivate microorganisms located on said article or said area.

8. The method as claimed in claim 7 wherein an article to be surface coated is selected from the group consisting of medical products, food packaging, packaging film, textiles, building materials, toys, electronic devices, furniture and hygiene articles.

* * * * *